United States Patent
Wang et al.

(10) Patent No.: US 9,810,670 B2
(45) Date of Patent: Nov. 7, 2017

(54) IONIC STRENGTH-MEDIATED PH GRADIENT ION EXCHANGE CHROMATOGRAPHY

(71) Applicant: Genentech, Inc., South San Francisco, CA (US)

(72) Inventors: Yajun Wang, Foster City, CA (US); George Tony Moreno, South San Francisco, CA (US); Boyan Zhang, South San Francisco, CA (US); Liangyi Zhang, South San Francisco, CA (US); Dell Farnan, South San Francisco, CA (US); Thomas Patapoff, South San Francisco, CA (US)

(73) Assignee: GENENTECH, INC., South San Francisco, CA (US)

( * ) Notice: Subject to any disclaimer, the term of this patent is extended or adjusted under 35 U.S.C. 154(b) by 0 days.

(21) Appl. No.: 14/443,329

(22) PCT Filed: Nov. 15, 2013

(86) PCT No.: PCT/US2013/070415
§ 371 (c)(1),
(2) Date: May 15, 2015

(87) PCT Pub. No.: WO2014/078729
PCT Pub. Date: May 22, 2014

(65) Prior Publication Data
US 2015/0285771 A1 Oct. 8, 2015

Related U.S. Application Data

(60) Provisional application No. 61/727,051, filed on Nov. 15, 2012, provisional application No. 61/780,707, filed on Mar. 13, 2013.

(51) Int. Cl.
*G01N 30/96* (2006.01)
*C07K 1/18* (2006.01)
*G01N 33/68* (2006.01)

(52) U.S. Cl.
CPC .............. *G01N 30/96* (2013.01); *C07K 1/18* (2013.01); *G01N 33/6803* (2013.01)

(58) Field of Classification Search
None
See application file for complete search history.

(56) References Cited

U.S. PATENT DOCUMENTS

| | | |
|---|---|---|
| 4,676,980 A | 6/1987 | Segal et al. |
| 4,816,567 A | 3/1989 | Cabilly et al. |
| 5,208,020 A | 5/1993 | Chari et al. |
| 5,229,275 A | 7/1993 | Goroff |
| 5,500,362 A | 3/1996 | Robinson et al. |
| 5,534,615 A | 7/1996 | Baker et al. |
| 5,545,807 A | 8/1996 | Surani et al. |
| 5,565,332 A | 10/1996 | Hoogenboom et al. |
| 5,567,610 A | 10/1996 | Borrebaeck et al. |
| 5,571,894 A | 11/1996 | Wels et al. |
| 5,573,905 A | 11/1996 | Lerner et al. |
| 5,587,458 A | 12/1996 | King et al. |
| 5,589,369 A | 12/1996 | Seidman et al. |
| 5,591,669 A | 1/1997 | Krimpenfort et al. |
| 5,591,828 A | 1/1997 | Bosslet et al. |
| 5,641,870 A | 6/1997 | Rinderknecht et al. |
| 5,693,780 A | 12/1997 | Newman et al. |
| 5,712,374 A | 1/1998 | Kuntsmann et al. |
| 5,731,168 A | 3/1998 | Carter et al. |
| 5,821,337 A | 10/1998 | Carter et al. |
| 7,521,541 B2 | 4/2009 | Eigenbrot et al. |
| 2006/0067930 A1 | 3/2006 | Adams et al. |
| 2006/0240564 A1 | 10/2006 | Shieh et al. |
| 2010/0234577 A1 | 9/2010 | Mazzola et al. |

FOREIGN PATENT DOCUMENTS

| | | |
|---|---|---|
| EP | 0 308 936 A2 | 3/1989 |
| EP | 0 404 097 B1 | 9/1996 |
| JP | 2008-511337 A | 4/2008 |
| JP | 2010-510963 A | 4/2010 |
| WO | WO-91/00360 A1 | 1/1991 |
| WO | WO-92/20373 A1 | 11/1992 |
| WO | WO-93/08829 A1 | 5/1993 |
| WO | WO-93/11161 A1 | 6/1993 |
| WO | WO-93/16185 A2 | 8/1993 |

(Continued)

OTHER PUBLICATIONS

Andersen et al. "Isoelectric Point Separation of Proteins by Capillary pH-gradient Ion-Exchange Chromatography," *Journal of Chromatography A* 1025(2):217-226, (Feb. 6, 2004).
Barlow et al. "The Distribution of Charged Groups in Proteins," *Biopolymers* 25:1717-1733, (1986).
Brennan et al. "Preparation of Bispecific Antibodies by Chemical Recombination of Monoclonal Immunoglobulin $G_1$ Fragments," *Science* 229:81-83, (Jul. 5, 1985).

(Continued)

*Primary Examiner* — Jacob Cheu
(74) *Attorney, Agent, or Firm* — Morrison & Foerster LLP

(57) ABSTRACT

The present invention provides methods for analyzing compositions of polypeptides such as antibodies by ionic strength-mediated pH gradient ion exchange chromatography. In some aspects, the methods use a combination of pH gradients and ionic strength gradients to separate the polypeptide from charge variants of the polypeptide. In some aspects, the methods use a stable ionic strength to optimize the pH gradient separation window to separate the polypeptide from charge variants. Such methods are useful for analyzing polypeptide, e.g. antibodies, with a pI greater than 9 or a pI less than 7. In some aspects, the invention provides a multiproduct method for the analysis of polypeptides of varying pI's.

46 Claims, 35 Drawing Sheets

(56) References Cited

FOREIGN PATENT DOCUMENTS

| WO | WO-93/16185 A3 | 8/1993 |
|---|---|---|
| WO | WO-94/04690 A1 | 3/1994 |
| WO | WO-94/04690 C1 | 3/1994 |
| WO | WO-94/11026 A2 | 5/1994 |
| WO | WO-94/11026 A3 | 5/1994 |
| WO | WO-00/29004 A1 | 5/2000 |
| WO | WO-00/55203 A1 | 9/2000 |
| WO | WO-02/051870 A2 | 7/2002 |
| WO | WO-02/051870 A3 | 7/2002 |
| WO | WO-03/035694 A2 | 5/2003 |
| WO | WO-03/035694 A3 | 5/2003 |
| WO | WO-2005/035572 A2 | 4/2005 |
| WO | WO-2005/035572 A3 | 4/2005 |
| WO | WO-2006/028936 A2 | 3/2006 |
| WO | WO-2007/075283 A2 | 7/2007 |
| WO | WO-2009/017491 A1 | 2/2009 |
| WO | WO-2011/009623 A1 | 1/2011 |
| WO | WO-2011/037983 A1 | 3/2011 |
| WO | WO-2012/084829 A1 | 6/2012 |

OTHER PUBLICATIONS

Brodeur et al. "Mouse-Human Myeloma Partners for the Production of Heterohybridomas," Chapter 4 in *Monoclonal Antibody Production Techniques and Application*, Marcel Dekker, Inc., New York, pp. 51-63, (1987).

Brüggemann et al. "Designer Mice: The Production of Human Antibody Repertoires in Transgenic Animals," *Year in Immunol.* 7:33-40, (1993).

Capel et al. "Heterogeneity of Human IgG Fc Receptors," *Immunomethods* 4:25-34 (1994).

Caron et al. "Engineering Humanized Dimeric Forms of IgG Are More Effective Antibodies," *J. Exp Med.* 176: 1191-1195, (Oct. 1, 1992).

Carter et al. "High Level *Escherichia coli* Expression and Production of a Bivalent Humanized Antibody Fragment," *Biotechnology* 10(2):163-167, (Feb. 1992).

Carter et al. "Humanization of an Anti-p185$^{HER2}$ Antibody for Human Cancer Therapy," *Proc. Natl. Acad. Sci. USA* 89:4285-4289, (May 1992).

Chothia et al. "Canonical Structures for the Hypervariable Regions of Immunoglobulins," *J. Mol. Biol.* 196:901-917, (1987).

Clackson et al. "Making Antibody Fragments Using Phage Display Libraries," *Nature* 352:624-628, (Aug. 15, 1991).

Clynes et al. "Fc Receptors are Required in Passive and Active Immunity to Melanoma," *Proc. Natl. Acad. Sci. USA* 95:652-656, (Jan. 1998).

Cunningham et al. "High-Resolution Epitope Mapping of hGH-Receptor Interactions by Alanine-Scanning Mutagenesis," *Science* 244:1081-1085, (Jun. 2, 1989).

Daëron. "Fc Receptor Biology," *Annu. Rev. Immunol.* 15:203-234, (1997).

Davies et al. "'Camelising' Human Antibody Fragments: NMR Studies on VH Domains," *Feb Lett.* 339:285-290, (Feb. 21, 1994).

De Haas et al. "Fcγ Receptors of Phagocytes," *J. Lab. Clin. Med.* 126:330-341, (1995).

Dick et al. "Identification and Measurement of Isoaspartic Acid Formation in the Complementarity Determining Region of a Fully Human Monoclonal Antibody," *J. Chromatogr. B* 877:3841-3849, (2009, e-pub. Sep. 25, 2009).

Dooley et al. "Antibody Repertoire Development in Cartilaginous Fish," *Dev. Comp. Immunol.* 30(1-2):43-56, (2006, e-pub. Jul. 22, 2005).

Farnan et al. "Multiproduct High-Resolution Monoclonal Antibody Charge Variant Separations by pH Gradient Ion-Exchange Chromatography," *Anal. Chem.* 81(21): 8846-8857, (Nov. 1, 2009).

Gazzano-Santoro et al. "A Non-Radioactive Complement-Dependent Cytotoxicity Assay for Anti-CD20 Monoclonal Antibody," *J. Immunol. Methods* 202:163-171, (1997).

Goding. "Production of Monoclonal Antibodies," Chapter 3 in *Monoclonal Antibodies: Principles and Practice*, pp. 56-103, Academic Press, (1983).

Griffiths et al. "Human Anti-Self Antibodies With High Specificity From Phage Display Libraries," *EMBO J.* 12(2):725-734, (1993).

Gruber et al. "Efficient Tumor Cell Lysis Mediated by a Bispecific Single Chain Antibody Expressed in *Escherichia coli*," *J. Immunol.* 152:5368-5374, (1994).

Guyer et al. "Immunoglobulin Binding by Mouse Intestinal Epithelial Cell Receptors," *J. Immunol.* 117(2):587-593, (Aug. 1976).

Holliger et al. "Diabodies: Small Bivalent and Bispecific Antibody Fragments," *Proc. Natl. Acad. Sci. USA*, 90:6444-6448, (Jul. 1993).

Holt et al. "Domain Antibodies: Proteins for Therapy," *Trends Biotechnol.* 21(11):484-490, (Nov. 2003).

Hwang et al., "Purification of Ascitic Fluid-Derived Murine Monoclonal Antibodies by Anion-Exchange and Size Exclusion High-Performance Liquid Chromatography," *Journal of Chromatography* 430:329-339, (1988).

Igawa et al. "Reduced Elimination of IgG Antibodies by Engineering the Variable Region," *Protein Eng. Des. Sel.* 23(5):385-392, (2010, e-pub. Feb. 15, 2010).

Jakobovits et al. "Analysis of Homozygous Mutant Chimeric Mice: Deletion of the Immunoglobulin Heavy-Chain Joining Region Blocks B-Cell Development and Antibody Production," *Proc. Natl. Acad. Sci. USA* 90:2551-2555, (Mar. 1993).

Jakobovits et al. "Germ-line Transmission and Expression of a Human-Derived Yeast Artificial Chromosome," *Nature* 362:255-258, (Mar. 18, 1993).

Johnson et al. "Human Antibody Engineering," *Current Opinion in Structural Biology* 3:564-571, (1993).

Jones et al. "Replacing the Complementarity Determining Regions in a Human Antibody With Those From a Mouse," *Nature* 321:522-525, (May 29, 1986).

Kaltenbrunner et al. "Isoprotein Analysis by Ion-Exchange Chromatography Using a Linear pH Gradient Combined With a Salt Gradient," *Journal of Chromatography A* 639:41-49.

Kim et al. "Localization of the Site of the Murine IgG1 Molecule That is Involved in Binding to the Murine Intestinal Fc Receptor," *Eur. J. Immunol.* 24:2429-2434, (1994).

Köhler et al. "Continuous Cultures of Fused Cells Secreting Antibody of Predefined Specificity," *Nature* 256:495-497, (Aug. 7, 1975).

Kostelny et al. "Formation of a Bispecific Antibody by the use of Leucine Zippers," *J. Immunol.* 148(5):1547-1553, (Mar. 1, 1992).

Kozbor et al. "A Human Hybrid Myeloma for Production of Human Monoclonal Antibodies," *J. Immunol.* 133(6):3001-3005, (Dec. 1984).

Lehninger. *Biochemistry*, second ed., Worth Publishers, New York, pp. 73-75, (1975).

Liu et al. "Glutamine Deamidation of a Recombinant Monoclonal Antibody," *Rapid Commun. Mass Spectrom.* 22:4081-4088, (2008).

Marks et al. "By-passing Immunization Human Antibodies from V-Gene Libraries Displayed on Phage," *J. Mol. Biol.* 222:581-597 (1991).

Marks et al. "By-Passing Immunization: Building High Affinity Human Antibodies by Chain Shuffling," *Bio/Technolgy* 10:779-783, (Jul. 1992).

McCafferty et al. "Phage Antibodies: Filamentous Phage Displaying Antibody Variable Domains," *Nature*: 348:552-554, (Dec. 6, 1990).

Miller et al. "Characterization of Site-Specific Glycation During Process Development of a Human Therapeutic Monoclonal Antibody," *J. Pharm. Sci.* 100(7):2543-2550, (Jul. 2011).

Milstein et al "Hybrid Hybridomas and Their Use in Immunohistochemistry," *Nature* 305:537-540, (Oct. 6, 1983).

Morimoto et al."Single-Step Purification of F(ab')$_2$ Fragments of Mouse Monoclonal Antibodies (Immunoglobulins G1) by Hydrophobic Interaction High Performance Liquid Chromatography Using TSKgel Phenyl-5PW," *Journal of Biochemical and Biophysical Methods* 24:107-117, (1992).

Morrison et al. "Chimeric Human Antibody Molecules: Mouse Antigen-Binding Domains With Human Constant Region Domains," *Proc. Natl. Acad. Sci. USA* 81:6851-6855, (Nov. 1984).

(56) References Cited

OTHER PUBLICATIONS

Munson et al. "Ligand: A Versatile Computerized Approach for Characterization of Ligand-Binding Systems," *Anal. Biochem.* 107:220-239, (1980).

Muyldermans et al. "Recognition of antigens by single-domain antibody fragments: the superfluous luxury of paired domains," *Trends Biochem. Sci.* 26(4):230-235, (Apr. 2001).

Plückthun. "Mono-and Bivalent Antibody Fragments Produced in *Escherichia coli*: Engineering, Folding and Antigen Binding," *Immunol. Reviews* 130:151-188, (1992).

Plückthun. "Antibodies from *Escherichia coli*," Chapter 11 in *The Pharmacology of Monoclonal Antibodies*, vol. 113, Rosenberg and Moore eds., Springer-Verlag, New York, pp. 269-315, (1994).

Podgornik et al. "Separation of Manganese Peroxidase Isoenzymes on Strong Anion-Exchange Monolithic Column Using pH-Salt Gradient," *Journal of Chromatography B* 799(2):343-347, (2004).

Presta. "Antibody Engineering," *Curr. Op. Struct. Biol.* 2:593-596, (1992).

Presta et al. "Humanization of an Antibody Directed Against IgE," *J. Immunol.* 151(5):2623-2632, (Sep. 1, 1993).

Ravetch et al. "Fc Receptors," *Annu. Rev. Immunol.* 9:457-492, (1991).

Rea et al. "Validation of a pH Gradient-Based Ion-Exchange Chromatography Method for High-Resolution Monoclonal Antibody Charge Variant Separations". *Journal of Pharmaceutical and Biomedical Analysis* 54(2):317-323, (2011, e-pub. Sep. 29, 2010).

Riechmann et al. "Reshaping Human Antibodies for Therapy," *Nature* 332:323-329, (Mar. 24, 1988).

Shopes. "A Genetically Engineered Human IgG Mutant With Enhanced Cytolytic Activity," *J. Immunol.* 148(9):2918-2922, (May 1, 1992).

Sims et al. "A Humanized CD18 Antibody Can Block Function Without Cell Destruction," *J. Immunol.* 151(4):2296-2308, (Aug. 15, 1993).

Skerra. "Bacterial Expression of Immunoglobulin Fragments," *Curr. Opinion in Immunol.* 5:256-262 (1993).

Sosic et al. "Application of Imaging Capillary IEF for Characterization and Quantitative Analysis of Recombinant Protein Charge Heterogeneity," *Electrophoresis* 29:4368-4376, (2008).

Stevenson et al "A Chimeric Antibody With Dual Fc Regions (bisFabFc) Prepared by Manipulations at the IgG Hinge," *Anti-Cancer Drug Design* 3:219-230, (1989).

Suresh et al. "Bispecific Monoclonal Antibodies From Hybrid Hybridomas," *Methods in Enzymology* 121:210-228, (1986).

Teshima et al. "Separation of Oxidized Variants of a Monoclonal Antibody by Anion-Exchange," *J. Chromatogr. A* 1218(15):2091-2097, (Apr. 15, 2011).

Traunecker et al. "Bispecific Single Chain Molecules (Janusins) Target Cytotoxic Lymphocytes on HIV Infected Cells," *EMBO J.* 10(12):3655-3659, (1991).

Tsonev et al. "Theory and Applications of a Novel Ion Exchange Chromatographic Technology Using Controlled pH Gradients for Separating Proteins on Anionic and Cationic Stationary Phases," *J. Chromatogr. A* 1200:166-182, (2008, e-pub. Jun. 12, 2008).

Tutt et al. "Trispecific $F(ab')_3$ Derivatives That Use Cooperative Signaling Via the TCR/CD3 Complex and CD2 to Activate and Redirect Resting Cytotoxic T Cells," *J. Immunol.* 147(1):60-69, (Jul. 1, 1991).

Verhoeyen et al. "Reshaping Human Antibodies: Grafting an Antilysozyme Activity," *Science* 239:1534-1536, (Mar. 25, 1988).

Vitetta et al. "Redesigning Nature's Poisons to Create Anti-Tumor Reagents," *Science* 238:1098-1104, (Nov. 20, 1987).

Vlasak et al. "Heterogeneity of Monoclonal Antibodies Revealed by Charge-Sensitive Methods," *Curr. Pharm. Biotechnol.* 9:468-481, (2008).

Wang et al "impact of Methionine Oxidation in Human IgG1 Fc on Serum Half-life of Monoclonal Antibodies," *Mol. Immunol.* 48:860-866, (2011, e-pub. Jan. 21, 2011).

Ward et al. "Binding Activities of a Repertoire of Single Immunoglobulin Variable Domains Secreted From *Escherichia coli*," *Nature* 341:544-546, (Oct. 12, 1989).

Waterhouse et al. "Combinatorial Infection and in vivo Recombination: A Strategy for Making Large Phage Antibody Repertoires," *Nuc. Acids. Res.* 21(9):2265-2266, (1993).

Winnik. "Continuous pH/Salt Gradient and Peptide Score for Strong Cation Exchange Chromatography in 2D-Nano-LC/MS/MS Peptide Identification for Proteomics," *Analytical Chemistry* 77(15):4991-4998, (Aug. 1, 2005).

Wolff et al. "Monoclonal Antibody Homodimers: Enhanced Antitumor Activity in Nude Mice," *Cancer Research* 53:2560-2565, (Jun. 1, 1993).

Yu et al. "Accurate Determination of Succinimide Degradation Products Using High Fidelity Trypsin Digestion Peptide Map Analysis," *Anal. Chem.* 83(15):5912-5919, (Jun. 21, 2011).

Zapata et al. "Engineering linear $F(ab')_2$ Fragments for Efficient Production in *Escherichia coli* and Enhanced Antiproliferative Activity," *Protein Eng.* 8(10):1057-1062, (1995).

Zhang et al. "Improving pH Gradient Cation-Exchange Chromatography of Monoclonal Antibodies by Controlling Ionic Strength", *Journal of Chromatography A* 1272:56-64, (2013, e-pub. Nov. 29, 2012.).

International Search Report dated Jan. 30, 2014, for PCT Application No. PCT/US2013/070415, filed on Nov. 15, 2013, 6 pages.

Written Opinion dated Jan. 30, 2014, for PCT Application No. PCT/US2013/070415, filed on Nov. 15, 2013, 8 pages.

Ahamed et al. "Selection of pH-related Parameters in Ion-Exchange Chromatography Using pH-Gradient Operations," *Journal of Chromatography A* 1194(1):22-29, (2008, e-pub. Dec. 8, 2007).

Anderson et al. "Gradient Chromatofocusing Iconic Strength Effects," *Clin. Chem.* 47(6):A39, Abstract No. 128, (2001).

He et al. "Analysis of Charge Heterogeneities in mAbs Using Imaged CE," *Electrophoresis* 30:714-722, (2009).

Jiang et al. "Purification Process Development of a Recombinant Monoclonal Antibody Expressed in Glycoengineered *Pichia pastoris*," *Protein Expression and Purification* 76(1):7-14 (2011, e-pub. Nov. 11, 2010).

Kim et al. "Characterization of a unique IgG1 mAb CEX profile by limited Lys-C proteolysis/CEX separation coupled with mass spectrometry and structural analysis," *J. Chromatogr.* B 878:1973-1981, (Jul. 15, 2010).

Nordborg et al. "Characterization of Monoclonal Antibodies Using Polymeric Cation Exchange Monoliths in Combination With Salt and pH Gradients," *J. Sep.Sci.* 32:2668-2673, (2009).

Rea et al. "Monoclonal Antibody Development and Physicochemical Characterization by High Performance Ion Exchange Chromatography," Chapter 19 in *Innovations in Biotechnology*, Agbo, E.C., Intech Europe, pp. 339-464, (Feb. 2012, e-pub. Feb. 17, 2012).

Rozhkova. "Quantitative Analysis of Monoclonal Antibodies by Cation-Exchange Chromatofocusing," *J. Chromatogr. A* 1216:5989-5994, (Aug. 7, 2009).

Shan et al. "Effect of Buffer Concentration on Gradient Chromatofocusing Performance Separating Proteins on a High-Performance DEAE Column," *J. Chromatogr. A* 909(2)191-205, (Feb. 16, 2001).

Shan et al. "Gradient Chromatofocusing. Versatile pH Gradient Separation of Proteins in Ion-Exchange HPLC: Characterization Studies," *Anal. Chem.* 74(21):5641-5649, (2002, e-pub. Oct. 8, 2002).

Staahlberg. "Electrostatic Retention Model for Ion-Exchange Chromatography," *Anal. Chem.* 66(4):440-449, (1994).

Ståhlberg. (1999) "Retention Models for Ions in Chromatography," *J. Chromatogr. A* 855(1):3-55, (Sep. 3, 1999).

Wang et al. "Improved Ion-Exchanged HPLC Method in mAb Using pH Gradient and its Comparison with cIEF," *Journal of liquid Chromatography and related Technologies* 35(9):1259-1269, (2012).

Wu et al. "Peak Identification in Capillary Isoelectric Focusing Using the Concept of Relative Peak Position as Determined by Two Isoelectric Point Markers," *Electrophoresis* 27:3584-3590, (2006).

Extended European Search Report for EP Application No. 13855528.9, filed on Nov. 15, 2013, dated Dec. 7, 2016, 18 pages.

(56) References Cited

OTHER PUBLICATIONS

Sober et al. "Chromatography of Proteins. II. Fractionation of Serum Protein on Anion-Exchange Cellulose," *Journal of the American Chemical Society* 78(4):756-763, (Feb. 20, 1956).

A. before optimization

B. before optimization

C. after optimization

D. after optimization

IONIC STRENGTH-MEDIATED PH GRADIENT ION EXCHANGE CHROMATOGRAPHY

CROSS-REFERENCE TO RELATED APPLICATIONS

This application is submitted under 35 U.S.C. §371 as a U.S. national stage application of International Application No. PCT/US2013/070415, having an International Filing Date of Nov. 15, 2013, and which claims priority to U.S. Provisional Patent Application No. 61/727,051, filed Nov. 15, 2012 and U.S. Provisional Patent Application No. 61/780,707, filed Mar. 13, 2013, the disclosure of each is hereby incorporated herein by reference in its entirety.

FIELD OF THE INVENTION

The present invention provides methods for analyzing preparations of polypeptides using ionic strength-mediated pH gradient ion exchange chromatography.

BACKGROUND OF THE INVENTION

Proteins like monoclonal antibodies (mAbs) have mostly charged and polar amino acids at the surface in an aqueous environment (Barlow, D J and Thornton, J M (1986) *Biopolymers* 25:1717). Because of molecular interaction with the solution components, the surface residues can undergo multiple chemical and enzymatic modifications, leading to a heterogeneous mixture of protein variants with slight differences on their electrostatic surface (Dick, L W et al., (2009) *J. Chromatogr.* B 877:3841; Liu, H W et al., (2008) *Rapid Commun. Mass Spectrom.* 22:4081; Miller, A K, et al., (2011) *J. Pharm. Sci.* 100:2543; Wang, W R et al., (2011) *Mol. Immunol.* 48:860). Cation-exchange chromatography (CEC) is considered to be the gold standard to profile the charge heterogeneity of protein therapeutics according to a recent review by Vlasak, J and Ionescu, R (2008 *Curr. Pharm. Biotechnol.* 9:468). The charge sensitive separation method is typically required by the regulatory agencies to ensure the production consistency during manufacturing and to monitor the degradation level of protein therapeutics (Miller, A K, et al., (2011) *J. Pharm. Sci.* 100:2543; He, X P Z (2009) *Electrophoresis* 30:714; Sosic, Z et al., (2008) *Electrophoresis* 29:4368; Kim, J et al., (2010) *J. Chromatogr.* B 878:1973: Teshima, G et al., (2010) *J. Chromatogr.* A 1218:2091).

Analytical ion exchange chromatography (IEC) methods using a pH gradient have emerged as alternative techniques to conventional salt gradient IEC for profiling the charge heterogeneity of therapeutic proteins (Farnan, D and Moreno, G T (2009) *Anal. Chem.* 81:8846; Tsonev, L I and Hirsh, A G (2008) *J. Chromatogr. A* 1200:166; Nordborg, A et al., (2009) *J. Sep. Sci.* 32:2668; Rozhkova, A (2009) *J. Chromatogr. A* 1216:5989; Rea, J C et al. (2010) *J. Pharm. Biomed. Anal.* 54:317). In this technique, proteins that are typically loaded on a cation-exchange stationary phase are eluted by increasing the pH of the mobile phase. It has recently been demonstrated that a pH gradient IEC (pH-IEC) method with a relatively broad pH window from 6.0 to 9.5 not only provided better resolution than traditional salt-gradient IEC, but also offered multi-product capability through the analysis of 12 monoclonal antibodies (mAbs) with pI from 7.3 to 9.0 (Farnan, D and Moreno, G T (2009) *Anal. Chem.* 81:8846). That pH-IEC method is also highly tolerant to sample matrix with varied ionic strengths (0 to 250 mM NaCl) and pH values (5.0 to 8.5) (Farnan, D and Moreno, G T (2009) *Anal. Chem.* 81:8846). Furthermore, the reported pH-IEC method is not evidently impacted by the column length and chemistry and fast separation with a shorter column can be achieved to improve the throughput of protein variant analysis. According to a recent validation report (Rea, J C et al. (2010) *J. Pharm. Biomed. Anal.* 54:317), the developed pH-IEC method has shown excellent precision at different chromatography conditions and good linearity at different column loads. Thus the reported pH-IEC method is suitable for routine testing in the biotechnology industry.

Despite the many advantages, the reported pH-IEC method was intended primarily for the mAbs with pI values in the studied range of 7.3 to 9.0. The fact that the elution profile of a mAb can vary with different buffer compositions and concentration, and the pH values at which the mAbs elutes indicates that pH-gradient IEC involves a combined ionic-strength and pH-gradient elution mechanism (Farnan, D and Moreno, G T (2009) *Anal. Chem.* 81:8846). This is also consistent with Anderson and coworkers' report on pH-gradient anion-exchange chromatography (pH-AIEC) (Anderson, D J and Shan, L (2001) *Clin. Chem.* 47:128; Shan, L and Anderson, D J (2001) *J. Chromatogr. A* 909:191; Shan, L and Anderson, D J (2002) *Anal. Chem.* 74:5641). With an increasing number of mAbs in the development phase in the biotechnology industry, especially more low-pI mAbs that show potentially longer half-life based on the animal studies (Igawa, T. (2010) *Protein Eng. Des. Sel.* 23:385) there is a need to expand the applicability of pH-IEC methods to a broader range of therapeutic mAbs.

All references cited herein, including patent applications and publications, are incorporated by reference in their entirety.

BRIEF SUMMARY

The invention provides a method for analyzing a composition comprising the polypeptide and one or more contaminants, the method comprising a) binding the polypeptide and one of more contaminants to an ion-exchange chromatography material using a loading buffer, wherein the loading buffer is at a first pH and comprises a first ionic strength; b) eluting the polypeptide and one or more contaminants from the ion-exchange chromatography material using an elution buffer wherein the pH of the elution buffer is altered in a pH gradient and the ionic strength of the elution buffer is altered in an ionic strength gradient, wherein the polypeptide and the one or more contaminants are separated by the combination of pH gradient and ionic strength gradient; c) detecting the polypeptide and the one or more contaminants. In some embodiments of the invention, polypeptides with pI's ranging from 6.0 to 9.5 can be analyzed using the same methods.

In some embodiments, the polypeptide is an antibody or immunoadhesin or fragment thereof. In further embodiments, the polypeptide is a monoclonal antibody or fragment thereof. In yet further embodiments, the antibody is a human antibody. In other embodiments, the antibody is a humanized antibody. In other embodiments, the antibody is a chimeric antibody. In some embodiments, the antibody is an antibody fragment.

In some embodiments of the above embodiments, the contaminant is a variant of the polypeptide. In further embodiments, the contaminant is a degradation product of the polypeptide.

In some embodiments, the polypeptide has a pI greater than about 9.0. In further embodiments, the chromatography material is a cation exchange chromatography material. In yet further embodiments, the cation exchange chromatography material is a sulfonated chromatography material or a carboxylated chromatography material.

In further embodiments of any of the above embodiments, the pH gradient is a linear gradient. In other embodiments of any one of the above embodiments, the pH gradient is a step gradient. In further embodiments, the pH gradient comprises an increase from about pH 5 to about pH 11. In some embodiments of the above embodiments, the pH gradient is generated using one or more buffers. In further embodiments, the one or more buffers is piperazine, imidazole, tris, phosphate, or CAPS.

In some embodiments of any one of embodiments, the ionic strength gradient is a linear gradient. In other embodiments, the ionic strength gradient is a step gradient. In some embodiments, the ionic strength gradient comprises an increase in salt concentration from about 0 mM to about 200 mM. In further embodiments, the ionic strength gradient is an NaCl gradient, a KCl gradient, or an $Na_2SO_4$ gradient.

In some embodiments of the above embodiments, the polypeptide has a pI less than about 7.0. In further embodiments, the chromatography material is an anion exchange chromatography material. In yet further embodiments, the anion exchange chromatography material is a quarternary amine chromatography material or a tertiary amine chromatography material. In some embodiments, the pH gradient is a linear gradient. In other embodiments, the pH gradient is a step gradient. In some embodiments, the pH gradient comprises a decrease from about pH 8 to about pH 5. In some embodiments, the pH gradient is generated using one or more buffers. In yet further embodiments, the one or more buffers is piperazine, imidazole or Tris. In some embodiments, the ionic strength gradient is a linear gradient. In other embodiments, the ionic strength gradient is a step gradient. In yet further embodiments, the ionic strength gradient comprises an increase in salt concentration from about 0 mM to about 200 mM. In some embodiments, the ionic strength gradient is a NaCl gradient, a KCl gradient, or a $Na_2SO_4$ gradient.

In some aspects, the invention provides a method for analyzing a composition comprising the polypeptide and one or more contaminants, the method comprising a) binding the polypeptide and one of more contaminants to an ion-exchange chromatography material using a loading buffer, wherein the loading buffer is at an initial pH and comprises an initial ionic strength; b) eluting the polypeptide and one or more contaminants from the ion-exchange chromatography material using an elution buffer wherein the pH of the elution buffer is altered in a pH gradient and wherein the ionic strength of the elution buffer is essentially the same as the initial ionic strength of the loading buffer, wherein the polypeptide and the one or more contaminants are separated by pH gradient at about the initial ionic strength; c) detecting the polypeptide and the one or more contaminants. In some embodiments of the invention, polypeptides with pI's ranging from 6.0 to 9.5 can be analyzed using essentially the same methods.

In some embodiments of the above aspect, the polypeptide is an antibody or immunoadhesin or fragment thereof. In further embodiments, the polypeptide is a monoclonal antibody or fragment thereof. In further embodiments of embodiments, the antibody is a human antibody. In other embodiments, the antibody is a humanized antibody. In yet other embodiments, the antibody is a chimeric antibody. In some embodiments, the antibody is an antibody fragment.

In some embodiments of the above aspect, the contaminant is a variant of the polypeptide. In some embodiments, the contaminant is a degradation product of the polypeptide.

In some embodiments of the above aspect, the polypeptide has a pI greater than about 9.0. In further embodiments, the chromatography material is a cation exchange chromatography material. In yet further embodiments, the cation exchange chromatography material is a sulfonated chromatography material or a carboxylated chromatography material.

In some embodiments of the above aspect, the pH gradient is a linear gradient. In other embodiments, the pH gradient is a step gradient. In some embodiments, the pH gradient comprises an increase from about pH 5 to about pH 11. In some embodiments, the pH gradient is generated using one or more buffers. In further embodiments, the one or more buffers is piperazine, imidazole, tris, phosphate, or CAPS.

In some embodiments the above embodiments, the ionic strength of the elution buffer is from about 0 mM to about 100 mM. In further embodiments, the elution buffer comprise about 0 mM NaCl to about 100 mM NaCl, about 0 mM KCl to about 100 mM KCl, or about 0 mM $Na_2SO_4$ to about 100 mM $Na_2SO_4$.

In some embodiments of the above aspect, the polypeptide has a pI less than about 7.0. In further embodiments, the chromatography material is an anion exchange chromatography material. In yet further embodiments, the anion exchange chromatography material is a quarternary amine chromatography material or a tertiary amine chromatography material. In some embodiments of the above embodiments, the pH gradient is a linear gradient. In other embodiments, the pH gradient is a step gradient. In some embodiments of the above embodiments, the pH gradient comprises a decrease from about pH 8 to about pH 5. In some embodiments, the pH gradient is generated using one or more buffers. In further embodiments, the one or more buffers is piperazine, imidazole or Tris. In some embodiments, the ionic strength of the elution buffer is from about 0 mM to about 100 mM. In further embodiments, the elution buffer comprises about 10 mM NaCl to about 100 mM NaCl.

In some embodiments of any one of the above embodiments, the analysis is by high performance liquid chromatography.

In some aspects, the invention provides a method of determining the purity of a polypeptide in a composition comprising analyzing the composition according to any one of the methods of the above embodiments and determining the ratio of polypeptide to contaminants in the composition.

In some aspects, the invention provides a method of determining the stability of a polypeptide in a composition comprising the polypeptide, the method comprising, a) incubating the composition comprising the polypeptide at 0° C. to 40° C. for one to six weeks, b) analyzing the composition of step a) by any of the methods of embodiments 1 to 63, and c) determining the ratio of variants to polypeptide in the composition, wherein an increase in the ratio of variants to polypeptide in the composition compared to a composition that was not incubated indicates the degradation of the polypeptide in the composition.

DETAILED DESCRIPTION OF THE INVENTION

Figure 1:
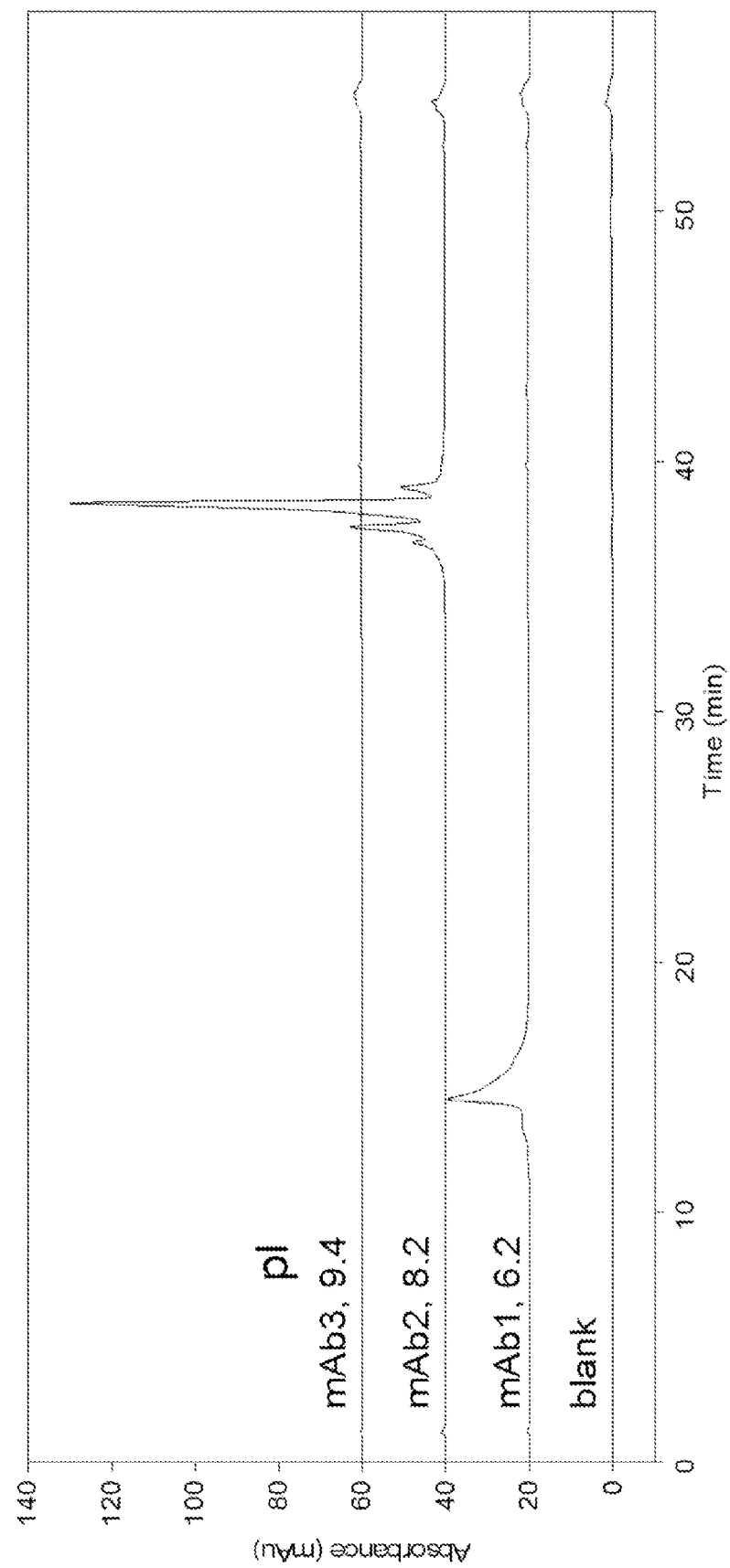
FIG. 1 shows the charge heterogeneity profiles on three monoclonal antibodies with different pIs (mAb1, mAb2 and mAb3) obtained with a pH-gradient ion exchange chromatography (IEC) method.

The invention provides methods of analyzing a composition comprising a polypeptide and one or more contaminants, e.g. polypeptide variants, comprising binding the polypeptide and one or more contaminants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is altered by an ionic strength gradient such that the polypeptides and the one or more contaminants elute from the chromatography material as distinct separate entities. The methods of the invention can be used to analyze polypeptides with isoelectric points that are not in the neutral pH range. In some embodiments, the methods may be used to effectively separate polypeptides with a pI greater than 9 from contaminants. In other embodiments, the methods may be used to effectively separation polypeptides with a pI less than 7 from contaminants. In some embodiments, the method effectively separates one or more contaminants from the polypeptide, wherein the polypeptide has a pI ranging from about 7.0 to about 12. In some embodiments, the method can be used to effectively separate one or more contaminants from the polypeptide, wherein the polypeptide has a pI ranging from about 7.0 to about 12. Examples of polypeptides include, but are not limited to, antibodies and antibody fragments. Examples of contaminants include, but are not limited to, antibody variants such as antibody charge variants.

In other aspects, the invention provides methods of analyzing a composition comprising a polypeptide and one or more contaminants, e.g. polypeptide variants, comprising binding the polypeptide and one or more contaminants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength essentially remains the same such that the polypeptides and the one or more contaminants elute from the chromatography material as distinct separate entities. The methods of the invention can be used to analyze polypeptides with isoelectric points that are not in the neutral pH range. In some embodiments, the methods may be used to effectively separate polypeptides with a pI greater than 9 from contaminants. In other embodiments, the methods may be used to effectively separate polypeptides with a pI less than 7 from contaminants. Examples of polypeptides include, but are not limited to, antibodies and antibody fragments. Examples of contaminants include, but are not limited to, antibody variants such as antibody charge variants.

In some aspects, the invention provides methods of analyzing compositions comprising a polypeptide and one or more contaminants, e.g. polypeptide variants, comprising binding the polypeptide and one or more contaminants to a ion exchange chromatography material using a loading buffer with an initial pH and an initial ionic strength such that the charge state of the polypeptide in the solution falls within an optimal pH gradient ion exchange separation window. The polypeptide and the one or more contaminants are then eluted from the chromatography material as distinct separate entities.

In some embodiments of the invention, the contaminants are polypeptide charge variants including acidic variants, i.e. variants with a retention time less than that of the main peak in the cation exchange mode. Examples of acidic variants include but are not limited to polypeptides where one or more glutamine and/or asparagine residues have been deamidated. In some embodiments of the invention, the contaminants are polypeptide charge variants including basic variants, i.e. variants with a retention time greater than that of the main peak in the cation exchange mode. Examples include but are not limited to variants where an aspartic acid residue has undergone modification to a succinimide moiety.

In some embodiments, the invention provides methods of analyzing a composition comprising a polypeptide and one or more contaminants, wherein essentially the same methods can be used to analyze polypeptides with different pI. For example, the method may be used to analyze polypeptides with pI's ranging from 6.0 to 9.5. In some embodiments, the polypeptides are antibodies, or fragments thereof. In some embodiments, the contaminants are antibody variants or variants of antibody fragments. In some embodiments, the contaminants are antibody charge variants or charge variants of antibody fragments. In some embodiments, the invention provides a method to analyze compositions of antibodies or antibody fragments for the presence of charge variants (e.g. acidic variants and/or basic variants) wherein the method can be used to analyze different compositions comprising an antibody wherein the antibody has a pI ranging from 6.0 to 9.5.

I. Definitions

The term "polypeptide" or "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. The terms "polypeptide" and "protein" as used herein specifically encompass antibodies.

The term "polypeptide charge variant" as used herein refers to polypeptide that has been modified from its native state such that the charge of the polypeptide is altered. In some examples, charge variants are more acidic than the parent polypeptide; i.e. have a lower pI than the parent polypeptide. In other examples, charge variants are more basic than the parent polypeptide; i.e. have a higher pI than the parent polypeptide. Such modifications may be engineered or the result of natural processes such as oxidation, deamidation, C-terminal processing of lysine residues, N-terminal pyroglutamate formation, and glycation. In some examples, a polypeptide charge variant is a glycoprotein where the glycan attached to the protein is modified such that the charge of the glycoprotein is altered compared to parent glycoprotein, for example, by addition of sialic acid or its derivatives. An "antibody charge variant" as used herein is an antibody or fragment thereof wherein the antibody or fragment thereof has been modified from its native state such that the charge of the antibody or fragment thereof is altered.

"Purified" polypeptide (e.g., antibody or immunoadhesin) means that the polypeptide has been increased in purity, such that it exists in a form that is more pure than it exists in its natural environment and/or when initially synthesized and/or amplified under laboratory conditions. Purity is a relative term and does not necessarily mean absolute purity.

The term "antagonist" is used in the broadest sense, and includes any molecule that partially or fully blocks, inhibits, or neutralizes a biological activity of a native polypeptide. In a similar manner, the term "agonist" is used in the broadest sense and includes any molecule that mimics a biological activity of a native polypeptide. Suitable agonist or antagonist molecules specifically include agonist or antagonist antibodies or antibody fragments, fragments or amino acid sequence variants of native polypeptides, etc. Methods for identifying agonists or antagonists of a polypeptide may comprise contacting a polypeptide with a candidate agonist or antagonist molecule and measuring a detectable change in one or more biological activities normally associated with the polypeptide.

A polypeptide "which binds" an antigen of interest, e.g. a tumor-associated polypeptide antigen target, is one that binds the antigen with sufficient affinity such that the polypeptide is useful as a diagnostic and/or therapeutic agent in targeting a cell or tissue expressing the antigen, and does not significantly cross-react with other polypeptides. In such embodiments, the extent of binding of the polypeptide to a "non-target" polypeptide will be less than about 10% of the binding of the polypeptide to its particular target polypeptide as determined by fluorescence activated cell sorting (FACS) analysis or radioimmunoprecipitation (RIA).

With regard to the binding of a polypeptide to a target molecule, the term "specific binding" or "specifically binds to" or is "specific for" a particular polypeptide or an epitope on a particular polypeptide target means binding that is measurably different from a non-specific interaction. Specific binding can be measured, for example, by determining binding of a molecule compared to binding of a control molecule, which generally is a molecule of similar structure that does not have binding activity. For example, specific binding can be determined by competition with a control molecule that is similar to the target, for example, an excess of non-labeled target. In this case, specific binding is indicated if the binding of the labeled target to a probe is competitively inhibited by excess unlabeled target.

The term "antibody" herein is used in the broadest sense and specifically covers monoclonal antibodies, polyclonal antibodies, multispecific antibodies (e.g. bispecific antibodies) formed from at least two intact antibodies, and antibody fragments so long as they exhibit the desired biological activity. The term "immunoglobulin" (Ig) is used interchangeable with antibody herein.

Antibodies are naturally occurring immunoglobulin molecules which have varying structures, all based upon the immunoglobulin fold. For example, IgG antibodies have two "heavy" chains and two "light" chains that are disulphide-bonded to form a functional antibody. Each heavy and light chain itself comprises a "constant" (C) and a "variable" (V) region. The V regions determine the antigen binding specificity of the antibody, whilst the C regions provide structural support and function in non-antigen-specific interactions with immune effectors. The antigen binding specificity of an antibody or antigen-binding fragment of an antibody is the ability of an antibody to specifically bind to a particular antigen.

The antigen binding specificity of an antibody is determined by the structural characteristics of the V region. The variability is not evenly distributed across the 110-amino acid span of the variable domains. Instead, the V regions consist of relatively invariant stretches called framework regions (FRs) of 15-30 amino acids separated by shorter regions of extreme variability called "hypervariable regions" that are each 9-12 amino acids long. The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

Each V region typically comprises three complementarity determining regions ("CDRs", each of which contains a "hypervariable loop"), and four framework regions. An antibody binding site, the minimal structural unit required to bind with substantial affinity to a particular desired antigen, will therefore typically include the three CDRs, and at least three, preferably four, framework regions interspersed there between to hold and present the CDRs in the appropriate conformation. Classical four chain antibodies have antigen binding sites which are defined by $V_H$ and $V_L$ domains in cooperation. Certain antibodies, such as camel and shark antibodies, lack light chains and rely on binding sites formed by heavy chains only. Single domain engineered immunoglobulins can be prepared in which the binding sites are formed by heavy chains or light chains alone, in absence of cooperation between $V_H$ and $V_L$.

The term "variable" refers to the fact that certain portions of the variable domains differ extensively in sequence among antibodies and are used in the binding and specificity of each particular antibody for its particular antigen. However, the variability is not evenly distributed throughout the variable domains of antibodies. It is concentrated in three segments called hypervariable regions both in the light chain and the heavy chain variable domains. The more highly conserved portions of variable domains are called the framework regions (FRs). The variable domains of native heavy and light chains each comprise four FRs, largely adopting a β-sheet configuration, connected by three hypervariable regions, which form loops connecting, and in some cases forming part of, the β-sheet structure. The hypervariable regions in each chain are held together in close proximity by the FRs and, with the hypervariable regions from the other chain, contribute to the formation of the antigen-binding site of antibodies (see Kabat et al., *Sequences of Proteins of Immunological Interest*, 5th Ed. Public Health Service, National Institutes of Health, Bethesda, Md. (1991)). The constant domains are not involved directly in binding an antibody to an antigen, but exhibit various effector functions, such as participation of the antibody in antibody dependent cellular cytotoxicity (ADCC).

The term "hypervariable region" when used herein refers to the amino acid residues of an antibody that are responsible for antigen binding. The hypervariable region may comprise amino acid residues from a "complementarity determining region" or "CDR" (e.g., around about residues 24-34 (L1), 50-56 (L2) and 89-97 (L3) in the $V_L$, and around about 31-35B (H1), 50-65 (H2) and 95-102 (H3) in the $V_H$ (Kabat et al., *Sequences of Proteins of Immunological Interest*, 5th Ed. Public Health Service, National Institutes of Health, Bethesda, Md. (1991)) and/or those residues from a "hypervariable loop" (e.g. residues 26-32 (L1), 50-52 (L2) and 91-96 (L3) in the $V_L$, and 26-32 (H1), 52A-55 (H2) and 96-101 (H3) in the $V_H$ (Chothia and Lesk *J. Mol. Biol.* 196:901-917 (1987)).

"Framework" or "FR" residues are those variable domain residues other than the hypervariable region residues as herein defined.

"Antibody fragments" comprise a portion of an intact antibody, preferably comprising the antigen binding region thereof. Examples of antibody fragments include Fab, Fab', F(ab')$_2$, and Fv fragments; diabodies; tandem diabodies (taDb), linear antibodies (e.g., U.S. Pat. No. 5,641,870, Example 2; Zapata et al., *Protein Eng.* 8(10):1057-1062 (1995)); one-armed antibodies, single variable domain antibodies, minibodies, single-chain antibody molecules; multispecific antibodies formed from antibody fragments (e.g., including but not limited to, Db-Fc, taDb-Fc, taDb-CH3, (scFV)4-Fc, di-scFv, bi-scFv, or tandem (di,tri)-scFv); and Bi-specific T-cell engagers (BiTEs).

Papain digestion of antibodies produces two identical antigen-binding fragments, called "Fab" fragments, each with a single antigen-binding site, and a residual "Fc" fragment, whose name reflects its ability to crystallize readily. Pepsin treatment yields an F(ab')$_2$ fragment that has two antigen-binding sites and is still capable of cross-linking antigen.

"Fv" is the minimum antibody fragment that contains a complete antigen-recognition and antigen-binding site. This region consists of a dimer of one heavy chain and one light chain variable domain in tight, non-covalent association. It is in this configuration that the three hypervariable regions of each variable domain interact to define an antigen-binding site on the surface of the $V_H$-$V_L$ dimer. Collectively, the six hypervariable regions confer antigen-binding specificity to the antibody. However, even a single variable domain (or half of an Fv comprising only three hypervariable regions specific for an antigen) has the ability to recognize and bind antigen, although at a lower affinity than the entire binding site.

The Fab fragment also contains the constant domain of the light chain and the first constant domain (CH1) of the heavy chain. Fab' fragments differ from Fab fragments by the addition of a few residues at the carboxy terminus of the heavy chain CH1 domain including one or more cysteines from the antibody hinge region. Fab'-SH is the designation herein for Fab' in which the cysteine residue(s) of the constant domains bear at least one free thiol group. F(ab')$_2$ antibody fragments originally were produced as pairs of Fab' fragments that have hinge cysteines between them. Other chemical couplings of antibody fragments are also known.

The "light chains" of antibodies (immunoglobulins) from any vertebrate species can be assigned to one of two clearly distinct types, called kappa ($\kappa$) and lambda ($\lambda$), based on the amino acid sequences of their constant domains.

Depending on the amino acid sequence of the constant domain of their heavy chains, antibodies can be assigned to different classes. There are five major classes of intact antibodies: IgA, IgD, IgE, IgG, and IgM, and several of these may be further divided into subclasses (isotypes), e.g., IgG1, IgG2, IgG3, IgG4, IgA, and IgA2. The heavy chain constant domains that correspond to the different classes of antibodies are called $\alpha$, $\delta$, $\epsilon$, $\gamma$, and $\mu$, respectively. The subunit structures and three-dimensional configurations of different classes of immunoglobulins are well known.

"Single-chain Fv" or "scFv" antibody fragments comprise the $V_H$ and $V_L$ domains of antibody, wherein these domains are present in a single polypeptide chain. In some embodiments, the Fv polypeptide further comprises a polypeptide linker between the $V_H$ and $V_L$ domains that enables the scFv to form the desired structure for antigen binding. For a review of scFv see Plückthun in *The Pharmacology of Monoclonal Antibodies*, vol. 113, Rosenburg and Moore eds., Springer-Verlag, New York, pp. 269-315 (1994).

The term "diabodies" refers to small antibody fragments with two antigen-binding sites, which fragments comprise a heavy chain variable domain ($V_H$) connected to a light chain variable domain ($V_L$) in the same polypeptide chain ($V_H$-$V_L$). By using a linker that is too short to allow pairing between the two domains on the same chain, the domains are forced to pair with the complementary domains of another chain and create two antigen-binding sites. Diabodies are described more fully in, for example, EP 404,097; WO 93/11161; and Hollinger et al., *Proc. Natl. Acad. Sci. USA*, 90:6444-6448 (1993).

The term "multispecific antibody" is used in the broadest sense and specifically covers an antibody that has polyepitopic specificity. Such multispecific antibodies include, but are not limited to, an antibody comprising a heavy chain variable domain ($V_H$) and a light chain variable domain ($V_L$), where the $V_H V_L$ unit has polyepitopic specificity, antibodies having two or more $V_L$ and $V_H$ domains with each $V_H V_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. "Polyepitopic specificity" refers to the ability to specifically bind to two or more different epitopes on the same or different target(s). "Mono specific" refers to the ability to bind only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

The expression "single domain antibodies" (sdAbs) or "single variable domain (SVD) antibodies" generally refers to antibodies in which a single variable domain (VH or VL) can confer antigen binding. In other words, the single variable domain does not need to interact with another variable domain in order to recognize the target antigen. Examples of single domain antibodies include those derived from camelids (lamas and camels) and cartilaginous fish (e.g., nurse sharks) and those derived from recombinant methods from humans and mouse antibodies (Nature (1989) 341:544-546; Dev Comp Immunol (2006) 30:43-56; Trend Biochem Sci (2001) 26:230-235; Trends Biotechnol (2003): 21:484-490; WO 2005/035572; WO 03/035694; Febs Lett (1994) 339:285-290; WO00/29004; WO 02/051870).

The term "monoclonal antibody" as used herein refers to an antibody obtained from a population of substantially homogeneous antibodies, i.e., the individual antibodies comprising the population are identical and/or bind the same epitope, except for possible variants that may arise during production of the monoclonal antibody, such variants generally being present in minor amounts. In contrast to polyclonal antibody preparations that typically include different antibodies directed against different determinants (epitopes), each monoclonal antibody is directed against a single determinant on the antigen. In addition to their specificity, the monoclonal antibodies are advantageous in that they are uncontaminated by other immunoglobulins. The modifier "monoclonal" indicates the character of the antibody as being obtained from a substantially homogeneous population of antibodies, and is not to be construed as requiring production of the antibody by any particular method. For example, the monoclonal antibodies to be used in accordance with the methods provided herein may be made by the hybridoma method first described by Kohler et al., *Nature* 256:495 (1975), or may be made by recombinant DNA methods (see, e.g., U.S. Pat. No. 4,816,567). The "monoclonal antibodies" may also be isolated from phage antibody libraries using the techniques described in Clackson et al., *Nature* 352:624-628 (1991) and Marks et al., *J. Mol. Biol.* 222:581-597 (1991), for example.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA* 81:6851-6855 (1984)). Chimeric antibodies of interest herein include "primatized" antibodies comprising variable domain antigen-binding sequences derived from a non-human primate (e.g. Old World Monkey, such as baboon, rhesus or cynomolgus monkey) and human constant region sequences (U.S. Pat. No. 5,693,780).

"Humanized" forms of non-human (e.g., murine) antibodies are chimeric antibodies that contain minimal sequence derived from non-human immunoglobulin. For the most part, humanized antibodies are human immunoglobulins (recipient antibody) in which residues from a hypervariable region of the recipient are replaced by residues from a hypervariable region of a non-human species (donor antibody) such as mouse, rat, rabbit or nonhuman primate having the desired specificity, affinity, and capacity. In some instances, framework region (FR) residues of the human immunoglobulin are replaced by corresponding non-human residues. Furthermore, humanized antibodies may comprise residues that are not found in the recipient antibody or in the donor antibody. These modifications are made to further refine antibody performance. In general, the humanized antibody will comprise substantially all of at least one, and typically two, variable domains, in which all or substantially all of the hypervariable loops correspond to those of a non-human immunoglobulin and all or substantially all of the FRs are those of a human immunoglobulin sequence, except for FR substitution(s) as noted above. The humanized antibody optionally also will comprise at least a portion of an immunoglobulin constant region, typically that of a human immunoglobulin. For further details, see Jones et al., *Nature* 321:522-525 (1986); Riechmann et al., *Nature* 332:323-329 (1988); and Presta, *Curr. Op. Struct. Biol.* 2:593-596 (1992).

For the purposes herein, an "intact antibody" is one comprising heavy and light variable domains as well as an Fc region. The constant domains may be native sequence constant domains (e.g. human native sequence constant domains) or amino acid sequence variant thereof. Preferably, the intact antibody has one or more effector functions.

"Native antibodies" are usually heterotetrameric glycoproteins of about 150,000 daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain ($V_H$) followed by a number of constant domains. Each light chain has a variable domain at one end ($V_L$) and a constant domain at its other end; the constant domain of the light chain is aligned with the first constant domain of the heavy chain, and the light chain variable domain is aligned with the variable domain of the heavy chain. Particular amino acid residues are believed to form an interface between the light chain and heavy chain variable domains.

A "naked antibody" is an antibody (as herein defined) that is not conjugated to a heterologous molecule, such as a cytotoxic moiety or radiolabel.

In some embodiments, antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors.

"Antibody-dependent cell-mediated cytotoxicity" and "ADCC" refer to a cell-mediated reaction in which nonspecific cytotoxic cells that express Fc receptors (FcRs) (e.g. Natural Killer (NK) cells, neutrophils, and macrophages) recognize bound antibody on a target cell and subsequently cause lysis of the target cell. The primary cells for mediating ADCC, NK cells, express FcγRIII only, whereas monocytes express FcγRI, FcγRII and FcγRIII. FcR expression on hematopoietic cells in summarized is Table 3 on page 464 of Ravetch and Kinet, *Annu. Rev. Immunol* 9:457-92 (1991). To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes et al., *Proc. Natl. Acad. Sci. (USA)* 95:652-656 (1998).

"Human effector cells" are leukocytes that express one or more FcRs and perform effector functions. In some embodiments, the cells express at least FcγRIII and carry out ADCC effector function. Examples of human leukocytes that mediate ADCC include peripheral blood mononuclear cells (PBMC), natural killer (NK) cells, monocytes, cytotoxic T cells and neutrophils; with PBMCs and NK cells being preferred.

"Complement dependent cytotoxicity" or "CDC" refers to the ability of a molecule to lyse a target in the presence of complement. The complement activation pathway is initiated by the binding of the first component of the complement system (C1q) to a molecule (e.g. polypeptide (e.g., an antibody)) complexed with a cognate antigen. To assess complement activation, a CDC assay, e.g. as described in Gazzano-Santoro et al., *J. Immunol. Methods* 202:163 (1996), may be performed.

The terms "Fc receptor" or "FcR" are used to describe a receptor that binds to the Fc region of an antibody. In some embodiments, the FcR is a native sequence human FcR. Moreover, a preferred FcR is one that binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain. (see Daëron, *Annu. Rev. Immunol.* 15:203-234 (1997)). FcRs are reviewed in Ravetch and Kinet, *Annu. Rev. Immunol* 9:457-92 (1991); Capel et al., *Immunomethods* 4:25-34 (1994); and de Haas et al., *J. Lab. Clin. Med.* 126:330-41 (1995). Other FcRs, including those to be identified in the future, are encompassed by the term "FcR" herein. The term also includes the neonatal receptor, FcRn, which is responsible for the transfer of maternal IgGs to the fetus (Guyer et al., *J. Immunol.* 117:587 (1976) and Kim et al., *J. Immunol.* 24:249 (1994)).

"Contaminants" refer to materials that are different from the desired polypeptide product. In some embodiments of the invention, contaminants include charge variants of the polypeptide. In some embodiments of the invention, contaminants include charge variants of an antibody or antibody fragment. In other embodiments of the invention, the contaminant includes, without limitation: host cell materials, such as CHOP; leached Protein A; nucleic acid; a variant, fragment, aggregate or derivative of the desired polypeptide; another polypeptide; endotoxin; viral contaminant; cell culture media component, etc. In some examples, the contaminant may be a host cell protein (HCP) from, for example but not limited to, a bacterial cell such as an *E. coli* cell, an insect cell, a prokaryotic cell, a eukaryotic cell, a yeast cell, a mammalian cell, an avian cell, a fungal cell.

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

As used herein "essentially the same" indicates that a value or parameter has not been altered by a significant effect. For example, an ionic strength of a chromatography mobile phase at column exit is essentially the same as the initial ionic strength of the mobile phase if the ionic strength has not changed significantly. For example, an ionic strength at column exit that is within 10%, 5% or 1% of the initial ionic strength is essentially the same as the initial ionic strength.

Reference to "about" a value or parameter herein includes (and describes) variations that are directed to that value or parameter per se. For example, description referring to "about X" includes description of "X".

As used herein and in the appended claims, the singular forms "a," "or," and "the" include plural referents unless the context clearly dictates otherwise. It is understood that aspects and variations of the invention described herein include "consisting" and/or "consisting essentially of" aspects and variations.

II. Methods of Chromatography

In some aspects, the invention provides methods of analyzing compositions comprising a polypeptide and one or more contaminants, e.g. polypeptide charge variants, comprising binding the polypeptide and one or more contaminants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is altered by an ionic strength gradient such that the polypeptides and the one or more contaminants elute from the chromatography material as distinct separate entities.

In other aspects, the invention provides methods of analyzing compositions comprising a polypeptide and one or more contaminants, e.g. polypeptide variants, comprising binding the polypeptide and one or more contaminants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is altered by an ionic strength gradient such that the polypeptides and the one or more contaminants elute from the chromatography material as distinct separate entities.

In some embodiments of any of the methods described herein, the chromatography material is a cation exchange material. In some embodiments, the cation exchange material is a solid phase that is negatively charged and has free cations for exchange with cations in an aqueous solution passed over or through the solid phase. In some embodiments of any of the methods described herein, the cation exchange material may be a membrane, a monolith, or resin. In some embodiments, the cation exchange material may be a resin. The cation exchange material may comprise a carboxylic acid functional group or a sulfonic acid functional group such as, but not limited to, sulfonate, carboxylic, carboxymethyl sulfonic acid, sulfoisobutyl, sulfoethyl, carboxyl, sulphopropyl, sulphonyl, sulphoxyethyl, or orthophosphate. In some embodiments of the above, the cation exchange chromatography material is a cation exchange chromatography column. In some embodiments, a cation exchange chromatography material is used for a polypeptide, e.g. and antibody or fragment thereof, with a pI greater than about 9. For example, the antibody or fragment thereof may have a pI of 9-10, 9-11, 10-11, 9-12, 10-12, or 11-12.

In some embodiments of any of the methods described herein, the chromatography material is an anion exchange material. In some embodiments, the anion exchange chromatography material is a solid phase that is positively charged and has free anions for exchange with anions in an aqueous solution passed over or through the solid phase. In some embodiments of any of the methods described herein, the anion exchange material may be a membrane, a monolith, or resin. In an embodiment, the anion exchange material may be a resin. In some embodiments, the anion exchange material may comprise a primary amine, a secondary amine, a tertiary amine or a quarternary ammonium ion functional group, a polyamine functional group, or a diethylaminoaethyl functional group. In some embodiments of the above, the anion exchange chromatography material is an anion exchange chromatography column. In some embodiments, an anion exchange chromatography material is used for a polypeptide, e.g. and antibody or fragment thereof, with a pI less than about 7. For example, the antibody or fragment thereof may have a pI of 6-7, 5-7, 5-6, 4-7, 4-6, or 4-5.

In some embodiments of any of the methods described herein, the ion exchange material may utilize a conventional chromatography material or a convective chromatography material. The conventional chromatography materials include, for example, perfusive materials (e.g., poly(styrene-divinylbenzene) resin) and diffusive materials (e.g., cross-linked agarose resin). In some embodiments, the poly(styrene-divinylbenzene) resin can be Poros resin. In some embodiments, the cross-linked agarose resin may be sulphopropyl-Sepharose Fast Flow ("SPSFF") resin. The convective chromatography material may be a membrane (e.g., polyethersulfone) or monolith material (e.g. cross-linked polymer). The polyethersulfone membrane may be Mustang. The cross-linked polymer monolith material may be cross-linked poly(glycidyl methacrylate-co-ethylene dimethacrylate).

In some embodiments of any of the methods of the invention, the chromatography material is in a chromatography column; for example a cation exchange chromatography column or an anion exchange chromatography column. In some embodiments, the chromatography column is used for liquid chromatography. In some embodiments, the chromatography column is used for high performance liquid chromatography (HPLC). In some embodiments, the chromatography column is an HPLC chromatography column; for example, a cation exchange HPLC column or an anion exchange HPLC column.

Examples of cation exchange materials are known in the art include, but are not limited to Mustang S, Sartobind S, SO3 Monolith, S Ceramic HyperD, Poros XS, Poros HS50, Poros HS20, SPSFF, SP-Sepharose XL (SPXL), CM Sepharose Fast Flow, Capto S, Fractogel Se HiCap, Fractogel SO3, or Fractogel COO. In some embodiments of any of the methods described herein, the cation exchange material is Poros HS50. In some embodiments, the Poros HS resin may be Poros HS 50 µm or Poros HS 20 µm particles. Examples of cation exchange chromatography columns for use in the methods of the invention include, but are not limited to ProPac WCX-10 and ProPac WCX-10HT.

Examples of anion exchange materials are known in the art and include, but are not limited to Poros HQ 50, Poros PI 50, Poros D, Mustang Q, Q Sepharose FF, and DEAE Sepharose. Examples of anion exchange chromatography columns for use in the methods of the invention include, but are not limited to Dionex ProPac 10 SAX and Tosoh GSKgel Q STAT 7 µM WAX.

An exemplary HPLC procedure that may used for the methods of the invention is as follows; however, the methods of the invention are not construed to be bound by these procedures. Samples are added to autosampler and are refrigerated (5±3° C.). Columns are placed in the column compartment and a temperature control feature may be employed to keep the compartment temperature within a narrow range (±1° C.) from the set point during analysis. Column effluent is monitored at 280 nm.

Samples are diluted with mobile phase to a target polypeptide concentration of approximately 1-2 mg/mL. In some embodiments, the polypeptide may be digested with carboxypeptidase B (CpB), added in a ratio of 1:100 (w/w) and incubated at 37° C. for 20 min. Samples may be stored at 5° C. until analysis.

The instrument may include a low-pressure quaternary gradient pump, a rapid separation auto-sampler with temperature control capability, a thermal-controlled column compartment and a diode array UV detector. At the outlet of the detector, a PCM-3000 pH and conductivity monitor may be connected to collect pH and conductivity data in real time. Instrument control, data acquisition, and data analysis can be performed; for example, by using Thermo Scientific Dionex Chromeleon software, version 6.8.

Non-limiting examples of mobile phase preparations are as follows. Individual stock buffer solutions of tris and imidazole are prepared at 1.0 M and a solution of CAPS is prepared at a concentration of 0.1 M, without adjusting the pH value and stored at room temperature. Individual components are diluted to a final concentration of 10 mM in approximately 90% of the target volume using deionized water and allowed to mix. Once the solution is quenched to the final volume, the mixture is divided into two equal aliquots.

The pH values of the buffers are adjusted by hydrochloric acid to 6.0 (Buffer A) and sodium hydroxide to 11.0 (Buffer B). Sodium chloride is prepared as a 0.1 M solution with deionized water (Buffer C). MilliQ water (18 MOhms) is dispensed into a separate container (Buffer D). All mobile phases are then individually filtered through a 0.2 µm nylon filter prior to use.

A non-limiting example of cation-exchange chromatography is as follows. Monoclonal antibody samples are diluted to 1 mg/mL with a 1:1 mixture of buffers A and D and are kept at 5±3° C. in the auto-sampler. A Propac WCX-10HT, 4×50 mm column is placed in the column compartment with the temperature setting at 40±1° C. For each chromatographic run, 20 µL of protein (20 µg) is injected. The mobile phase flow rate is 1.0 mL/min. Proteins are detected by ultraviolet (UV) absorbance at 280 nm.

In some examples, a hybrid pH gradient is established by using a quaternary gradient formed on the quaternary pump using buffers A, B, C and D. This arrangement offers the flexibility of adjusting 1) the starting and ending pH, using buffers A and B and 2) the amount of salt for each gradient, using buffers C and D. For example, a pH gradient from 6 to 10, with a constant salt concentration of 10 mM, is established by an increase of buffer B from 0 to 40%, while maintaining buffers C and D at 10% and 40%, respectively. Examples of hybrid gradients are provided in Table 2 in the examples below.

Various buffers which can be employed depending, for example, on the desired pH of the buffer, the desired conductivity of the buffer, the characteristics of the protein of interest, and the analytical method.

Elution, as used herein, is the removal of the product, e.g. polypeptide, and or contaminants from the chromatography material. Elution buffer is the buffer used to elute the polypeptide or other product of interest from a chromatography material. In some embodiments, the elution buffer is part to the mobile phase of the chromatography. In some embodiments, the composition comprising the polypeptide and the contaminants is applied to the chromatography material as part of the mobile phase. The mobile phase is then altered to allow for separation of the polypeptide from contaminants as the polypeptide and contaminants are eluted from the chromatography material. In many cases, an elution buffer has a different physical characteristic than the load buffer. For example, the elution buffer may have a different pH than load buffer and/or a different ionic strength than the load buffer. In some embodiments, the polypeptides and contaminants are eluted from the chromatography material by altering the pH and the ionic strength of the elution buffer. In some embodiments the pH of the elution buffer and the ionic strength of the elution buffer are increased over the course of the elution compared to the load buffer. In some embodiments the pH of the elution buffer is increased over the course of the elution compared to the load buffer and the ionic strength of the elution buffer remains essentially the same.

In some embodiments of the invention, a polypeptide with a pI>9 is applied to a cation exchange chromatography material and the polypeptide is eluted from the cation exchange chromatography material by increasing the pH and the ionic strength of the mobile phase of the chromatography. In some embodiments of the invention, a polypeptide with a pI>9 is applied to a cation exchange chromatography material and the polypeptide is eluted from the cation exchange chromatography material by increasing the pH of the mobile phase of the chromatography while maintaining the ionic strength of the mobile phase.

In some embodiments of the invention, a polypeptide with a pI<7 is applied to an anion exchange chromatography material and the polypeptide is eluted from the anion exchange chromatography material by decreasing the pH of the mobile phase of the chromatography and increasing the ionic strength of the mobile phase of the chromatography. In some embodiments of the invention, a polypeptide with a pI<7 is applied to an anion exchange chromatography material and the polypeptide is eluted from the anion exchange chromatography material by decreasing the pH of the mobile phase of the chromatography while maintaining the ionic strength of the mobile phase.

In some aspects of any of the above embodiments, the pH of the elution buffer changed from the load buffer by linear gradient or by step gradient.

In some embodiments of the invention, the polypeptide is eluted from the chromatography material by increasing the pH of the elution buffer in the mobile phase. In some embodiments, the pH of the elution buffer increases from about pH 5 to about pH 11. In some embodiments, the pH of the elution buffer increases from about pH 6 to about pH 9. In some embodiments, the pH of the elution buffer increases from about pH 6 to about pH 10. In some embodiments, the pH of the elution buffer increases from about pH 6 to about pH 11. In some embodiments, the pH of the elution buffer increases from about pH 7 to about pH 9. In some embodiments, the pH of the elution buffer increases from about pH 7 to about pH 10. In some embodiments, the pH of the elution buffer increases from about pH 7 to about pH 11. In some embodiments, the pH of the elution buffer increases from about pH 8 to about pH 9. In some embodiments, the pH of the elution buffer increases from about pH 8 to about pH 10. In some embodiments, the pH of the elution buffer increases from about pH 8 to about pH 11. In some embodiments, the pH of the elution buffer increases from about pH 9 to about pH 11. In any of the above embodiments, the increase in pH of the elution buffer is combined with an increase in the ionic strength of the elution buffer. In other embodiments of any of the above embodiments, the pH of the elution buffer is increased but the ionic strength of the elution buffer remains essentially the same. In any of the above embodiments, the pH gradient is established over more than any of about 10 min, 15 min, 20 min, 25 min, 30 min, 35 min, 40 min, 45 min, 50 min, 55 min, or 60 min. In any of the above embodiments, the chromatography material is a cation exchange chromatography material. In any of the above embodiments, the polypeptide has a pI>9. In any of the above embodiments, the polypeptide is an antibody or fragment thereof.

In some embodiments of the invention, the polypeptide is eluted from the chromatography material by decreasing the pH of the elution buffer in the mobile phase. In some embodiments, the pH of the elution buffer decreases from about pH 9 to about pH 5. In some embodiments, the pH of the elution buffer decreases from about pH 9 to about pH 6. In some embodiments, the pH of the elution buffer decreases from about pH 9 to about pH 7. In some embodiments, the pH of the elution buffer decreases from about pH 8 to about pH 5. In some embodiments, the pH of the elution buffer decreases from about pH 8 to about pH 6. In some embodiments, the pH of the elution buffer decreases from about pH 8 to about pH 7. In some embodiments, the pH of the elution buffer decreases from about pH 7 to about pH 5. In any of the above embodiments, the decrease in pH of the elution buffer is combined with an increase in the ionic strength of the elution buffer. In other embodiments of any of the above embodiments, the pH of the elution buffer is decreased but the ionic strength of the elution buffer remains essentially the same. In any of the above embodiments, the pH gradient is established over more than any of about 10 min, 15 min, 20 min, 25 min, 30 min, 35 min, 40 min, 45 min, 50 min, 55 min, or 60 min. In any of the above embodiments, the chromatography material is an anion exchange chromatography material. In any of the above embodiments, the polypeptide has a pI<7. In any of the above embodiments, the polypeptide is an antibody or fragment thereof.

An elution buffer can be prepared with a specific pH using buffers known in the art. Examples of buffers include but are not limited to piperazine, imidazole, Tris, phosphate, and N-cyclohexyl-3-aminopropanesulfonic acid (CAPS). In some embodiments, the pH of the buffer may be adjusted, for example, by adding HCl to make a buffer more acidic or adding NaOH to make a buffer more basic. In some embodiments, the elution buffer comprises a combination of buffers. In some embodiments, the elution buffer comprises a combination of piperazine, imidazole and Tris (e.g. a PIT buffer). In some embodiments, the elution buffer comprises 11.6 mM piperazine, 1.5 mM imidazole and 2.4 mM Tris. In some embodiments, the elution buffer comprises 4 mM piperazine, 4 mM imidazole and 4 mM Tris. In some embodiments of the invention, an elution buffer comprising a combination of piperazine, imidazole and Tris is used in the mobile phase of cation exchange chromatography of a polypeptide. In some embodiments of the invention, an elution buffer comprising a combination of piperazine, imidazole and Tris is used in the mobile phase of cation exchange chromatography of a polypeptide with a pI>9. In some embodiments of the invention, an elution buffer comprising a combination of piperazine, imidazole and Tris is used in the mobile phase of cation exchange chromatography of an antibody. In some embodiments of the invention, an elution buffer comprising a combination of piperazine, imidazole and Tris is used in the mobile phase of cation exchange chromatography of an antibody with a pI>9. In some embodiments of the invention, an elution buffer comprising a combination of piperazine, imidazole and Tris is used in the mobile phase of anion exchange chromatography of a polypeptide. In some embodiments of the invention, an elution buffer comprising a combination of piperazine, imidazole and Tris is used in the mobile phase of anion exchange chromatography of a polypeptide with a pI<7. In some embodiments of the invention, an elution buffer comprising a combination of piperazine, imidazole and Tris is used in the mobile phase of anion exchange chromatography of an antibody. In some embodiments of the invention, an elution buffer comprising a combination of piperazine, imidazole and Tris is used in the mobile phase of anion exchange chromatography of an antibody with a pI<7. In some embodiments, the elution buffer comprises a combination of Tris, piperazine and phosphate (e.g. a TPP buffer). In some embodiments, the elution buffer comprises 5 mM Tris, 5 mM piperazine and 5 mM phosphate. In some embodiments, the elution buffer comprises 10 mM Tris, 10 mM piperazine and 10 mM phosphate. In some embodiments of the invention, an elution buffer comprising a combination of Tris, piperazine and phosphate is used in the mobile phase of cation exchange chromatography of a polypeptide. In some embodiments of the invention, an elution buffer comprising a combination of Tris, piperazine and phosphate is used in the mobile phase of cation exchange chromatography of a polypeptide with a pI>9. In some embodiments of the invention, an elution buffer comprising a combination of Tris, piperazine and phosphate is used in the mobile phase of cation exchange chromatography of an antibody. In some embodiments of the invention, an elution buffer comprising a combination of Tris, piperazine and phosphate is used in the mobile phase of cation exchange chromatography of an antibody with a pI>9. In some embodiments, the elution buffer comprises a combination of Tris, imidazole and CAPS (e.g. a TIC buffer). In some embodiments, the elution buffer comprises 5 mM Tris, 5 mM imidazole and 5 mM CAPS. In some embodiments of the invention, an elution buffer comprising a combination of Tris, imidazole and CAPS is used in the mobile phase of cation exchange chromatography of a polypeptide. In some embodiments of the invention, an elution buffer comprising a combination of Tris, imidazole and CAPS is used in the mobile phase of cation exchange chromatography of a polypeptide with a pI>9. In some embodiments of the invention, an elution buffer comprising a combination of Tris, imidazole and CAPS is used in the mobile phase of cation exchange chromatography of an antibody. In some embodiments of the invention, an elution buffer comprising a combination of Tris, imidazole and CAPS is used in the mobile phase of cation exchange chromatography of an antibody with a pI>9.

In some embodiments of the invention, the polypeptide is eluted from the chromatography material by increasing the pH of the elution buffer as described above, and by increasing the ionic strength of the elution buffer in the mobile phase thereby forming a pH gradient and an ionic strength gradient. In some embodiments, the ionic strength of the elution buffer is increased by increasing the salt concentration of the mobile phase of the chromatography. In other embodiments of the invention, the polypeptide is eluted from the chromatography material by increasing the pH of the elution buffer where the ionic strength of the elution buffer remains essentially the same over the course of the elution by maintaining the salt concentration over the course of the elution. In some embodiments, the salt concentration is chosen such that the charge state of the polypeptide provides an optimal pH gradient ion exchange chromatography separation window. The charge state of the polypeptide can be determined by modeling procedures known in the art. Examples of salts include but are not limited to NaCl, KCl and $Na_2SO_4$.

In some embodiments, the ionic strength gradient is a salt gradient. In some embodiments the salt gradient is a gradient from about 0 mM salt to about 200 mM salt. In some embodiments, the salt gradient is any of from about 0 mM to about 100 mM, 0 mM to about 60 mM, 0 mM to about 50 mM, 0 mM to about 40 mM, 0 mM to about 30 mM, 0 mM to about 20 mM, 0 mM to about 10 mM, 10 mM to about 200 mM, 10 mM to about 100 mM, 10 mM to about 50 mM, 10 mM to about 40 mM, 10 mM to about 30 mM, 10 mM to about 20 mM, 20 mM to about 200 mM, 20 mM to about 100 mM, 20 mM to about 50 mM, 20 mM to about 30 mM, 30 mM to about 200 mM, 30 mM to about 100 mM, and 30 mM to about 50 mM.

In some embodiments of the above embodiments, the polypeptide and/or the one or more contaminants are eluted from the chromatography material by a combination of pH gradient and ionic strength gradient. In some embodiments, the pH gradient is from pH 5 to pH 10.8 and the ionic strength gradient is from 0 mM salt to 16 mM salt. In some embodiments, the pH gradient is from pH 6 to pH 11 and the ionic strength gradient is from 0 mM salt to 60 mM salt. In some embodiments, the pH gradient is from pH 5 to pH 9.5 and the ionic strength gradient is from 0 mM salt to 16 mM salt. In some embodiments, the pH gradient is from pH 5 to pH 9.5 and the ionic strength gradient is from 0 mM salt to 30 mM salt. In any of the above embodiments, the salt is NaCl, KCl or $Na_2SO_4$. In any of the above embodiments, the chromatography material is a cation exchange chromatography material. In any of the above embodiments, the polypeptide has a pI>9. In any of the above embodiments, the polypeptide is an antibody with a pI>9.

In some embodiments of the invention, a polypeptide and/or one or more contaminants are analyzed by ion exchange chromatography where the polypeptide and/or one or more contaminants is eluted from the chromatography material by a combination of pH gradient and ionic strength gradient. In some embodiments, the pH gradient is from pH 7 to pH 5 and the ionic strength gradient is from 0 mM salt to 25 mM salt. In some embodiments, the pH gradient is from pH 7 to pH 5 and the ionic strength gradient is from 0 mM salt to 100 mM salt. In some embodiments, the pH gradient is from pH 7 to pH 5 and the ionic strength gradient is from 0 mM salt to 200 mM salt. In some embodiments, the pH gradient is from pH 7 to pH 5 and the ionic strength gradient is from 0 mM salt to 300 mM salt. In any of the above embodiments, the salt is NaCl, KCl or $Na_2SO_4$. In any of the above embodiments, the chromatography material is an anion exchange chromatography material. In any of the above embodiments, the polypeptide has a pI<7. In any of the above embodiments, the polypeptide is an antibody with a pI<7.

In some embodiments of the invention, a polypeptide and/or one or more contaminants are analyzed by ion exchange chromatography where the polypeptide and/or one or more contaminants is eluted from the chromatography material by pH gradient where the ionic strength of the mobile phase remains essentially the same over the elution. In some embodiments, the pH gradient is from pH 6 to pH 11 and the ionic strength of the mobile phase is about 10 mM salt. In some embodiments, the pH gradient is from pH 6 to pH 11 and the ionic strength of the mobile phase is about 20 mM salt. In some embodiments, the pH gradient is from pH 6 to pH 11 and the ionic strength of the mobile phase is about 30 mM salt. In some embodiments, the pH gradient is from pH 6 to pH 11 and the ionic strength of the mobile phase is about 40 mM salt. In some embodiments, the pH gradient is from pH 6 to pH 11 and the ionic strength of the mobile phase is about 50 mM salt. In some embodiments, the pH gradient is from pH 6 to pH 10 and the ionic strength of the mobile phase is about 10 mM salt. In some embodiments, the pH gradient is from pH 6 to pH 10 and the ionic strength of the mobile phase is about 20 mM salt. In some embodiments, the pH gradient is from pH 6 to pH 10 and the ionic strength of the mobile phase is about 30 mM salt. In some embodiments, the pH gradient is from pH 6 to pH 10 and the ionic strength of the mobile phase is about 40 mM salt. In some embodiments, the pH gradient is from pH 6 to pH 10 and the ionic strength of the mobile phase is about 50 mM salt. In some embodiments, the pH gradient is from pH 6 to pH 9 and the ionic strength of the mobile phase is about 10 mM salt. In some embodiments, the pH gradient is from pH 6 to pH 9 and the ionic strength of the mobile phase is about 20 mM salt. In some embodiments, the pH gradient is from pH 6 to pH 9 and the ionic strength of the mobile phase is about 30 mM salt. In some embodiments, the pH gradient is from pH 6 to pH 9 and the ionic strength of the mobile phase is about 40 mM salt. In some embodiments, the pH gradient is from pH 6 to pH 9 and the ionic strength of the mobile phase is about 50 mM salt. In some embodiments, the pH gradient is from pH 7 to pH 11 and the ionic strength of the mobile phase is about 10 mM salt. In some embodiments, the pH gradient is from pH 7 to pH 11 and the ionic strength of the mobile phase is about 20 mM salt. In some embodiments, the pH gradient is from pH 7 to pH 11 and the ionic strength of the mobile phase is about 30 mM salt. In some embodiments, the pH gradient is from pH 7 to pH 11 and the ionic strength of the mobile phase is about 40 mM salt. In some embodiments, the pH gradient is from pH 7 to pH 11 and the ionic strength of the mobile phase is about 50 mM salt. In some embodiments, the pH gradient is from pH 7 to pH 10 and the ionic strength of the mobile phase is about 10 mM salt. In some embodiments, the pH gradient is from pH 7 to pH 10 and the ionic strength of the mobile phase is about 20 mM salt. In some embodiments, the pH gradient is from pH 7 to pH 10 and the ionic strength of the mobile phase is about 30 mM salt. In some embodiments, the pH gradient is from pH 7 to pH 10 and the ionic strength of the mobile phase is about 40 mM salt. In some embodiments, the pH gradient is from pH 7 to pH 10 and the ionic strength of the mobile phase is about 50 mM salt. In any of the above embodiments, the salt is NaCl, KCl or $Na_2SO_4$. In any of the above embodiments, the chromatography material is a cation exchange chromatography material. In any of the above embodiments, the polypeptide has a pI>9. In any of the above embodiments, the polypeptide is an antibody with a pI>9.

In some embodiments of the invention, a polypeptide and/or one or more contaminants are analyzed by ion exchange chromatography where the polypeptide and/or one or more contaminants is eluted from the chromatography material by a combination of pH gradient where the ionic strength of the mobile phase remains essentially the same over the elution. In some embodiments, the pH gradient is from pH 8 to pH 5 and the ionic strength of the mobile phase is about 10 mM salt. In some embodiments, the pH gradient is from pH 8 to pH 5 and the ionic strength of the mobile phase is about 20 mM salt. In some embodiments, the pH gradient is from pH 8 to pH 5 and the ionic strength of the mobile phase is about 30 mM salt. In some embodiments, the pH gradient is from pH 8 to pH 5 and the ionic strength of the mobile phase is about 40 mM salt. In some embodiments, the pH gradient is from pH 8 to pH 5 and the ionic strength of the mobile phase is about 50 mM salt. In some embodiments, the pH gradient is from pH 8 to pH 5 and the ionic strength of the mobile phase is about 100 mM salt. In some embodiments, the pH gradient is from pH 8 to pH 5 and the ionic strength of the mobile phase is about 200 mM salt. In some embodiments, the pH gradient is from pH 7 to pH 5 and the ionic strength of the mobile phase is about 10 mM salt. In some embodiments, the pH gradient is from pH 7 to pH 5 and the ionic strength of the mobile phase is about 20 mM salt. In some embodiments, the pH gradient is from pH 7 to pH 5 and the ionic strength of the mobile phase is about 30 mM salt. In some embodiments, the pH gradient is from pH 7 to pH 5 and the ionic strength of the mobile phase is about 40 mM salt. In some embodiments, the pH gradient is from pH 7 to pH 5 and the ionic strength of the mobile phase is about 50 mM salt. In some embodiments, the pH gradient is from pH 7 to pH 5 and the ionic strength of the mobile phase is about 100 mM salt. In some embodiments, the pH gradient is from pH 7 to pH 5 and the ionic strength of the mobile phase is about 200 mM salt. In any of the above embodiments, the salt is NaCl, KCl or $Na_2SO_4$. In any of the above embodiments, the chromatography material is an anion exchange chromatography material. In any of the above embodiments, the polypeptide has a pI<7. In any of the above embodiments, the polypeptide is an antibody with a pI<7.

In some embodiments of the invention, ionic strength of the mobile phase, e.g the elution buffer, is measured by conductivity of the mobile phase. Conductivity refers to the ability of an aqueous solution to conduct an electric current between two electrodes. In solution, the current flows by ion transport. Therefore, with an increasing amount of ions present in the aqueous solution, the solution will have a higher conductivity. The basic unit of measure for conductivity is the Siemen (or mho), mho (mS/cm), and can be measured using a conductivity meter, such as various models of Orion conductivity meters. Since electrolytic conductivity is the capacity of ions in a solution to carry electrical current, the conductivity of a solution may be altered by changing the concentration of ions therein. For example, the concentration of a buffering agent and/or the concentration of a salt (e.g. sodium chloride, sodium acetate, or potassium chloride) in the solution may be altered in order to achieve the desired conductivity. Preferably, the salt concentration of the various buffers is modified to achieve the desired conductivity.

In some embodiments, the mobile phase of the chromatography has an initial conductivity of more than about any of 0.0 mS/cm, 0.5 mS/cm, 1.0 mS/cm, 1.5 mS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, 10 mS/cm, 11 mS/cm, 12 mS/cm, 13 mS/cm, 14 mS/cm, 15 mS/cm, 16 mS/cm, 17.0 mS/cm, 18.0 mS/cm, 19.0 mS/cm, or 20.0 mS/cm. In some embodiments, the conductivity of the mobile phase is increased over the course of the chromatography, e.g. by an ionic strength gradient. In some embodiments, the conductivity of the mobile phase at the completion of elution is more than about any of 1.0 mS/cm, 1.5 mS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, 10 mS/cm, 11 mS/cm, 12 mS/cm, 13 mS/cm, 14 mS/cm, 15 mS/cm, 16 mS/cm, 17.0 mS/cm, 18.0 mS/cm, 19.0 mS/cm, or 20.0 mS/cm. In some embodiments, the conductivity of the mobile phase is increased by a linear gradient. In some embodiments, the conductivity of the mobile phase is increased by a step gradient comprising one of more steps.

In some embodiments, the initial conductivity of the mobile phase and the final conductivity of the mobile phase of the chromatography at elution of the polypeptide is essentially the same. In some embodiments, the conductivity of the mobile phase remains essentially at more than about any of 0.0 mS/cm, 0.5 mS/cm, 1.0 mS/cm, 1.5 mS/cm, 2.0 mS/cm, 2.5 mS/cm, 3.0 mS/cm, 3.5 mS/cm, 4.0 mS/cm, 4.5 mS/cm, 5.0 mS/cm, 5.5 mS/cm, 6.0 mS/cm, 6.5 mS/cm, 7.0 mS/cm, 7.5 mS/cm, 8.0 mS/cm, 8.5 mS/cm, 9.0 mS/cm, 9.5 mS/cm, 10 mS/cm, 11 mS/cm, 12 mS/cm, 13 mS/cm, 14 mS/cm, 15 mS/cm, 16 mS/cm, 17.0 mS/cm, 18.0 mS/cm, 19.0 mS/cm, or 20.0 mS/cm.

In some embodiments of any of the methods described herein, the composition comprising a polypeptide and one or more contaminants is loaded on the chromatography material at an amount of more than any one of about 1 µg, 2 µg, 3 µg, 4 µg, 5 µg, 6 µg, 7 µg, 8 µg, 9 µg, 10 µg, 15 µg, 20 µg, 25 µg, or 50 µg. In some embodiments, the composition is loaded onto the chromatography material at a concentration of more than any one of about 0.5 mg/mL, 1.0 mg/mL, 1.5 mg/mL, 2.0 mg/mL, 2.5 mg/mL, and 5.0 mg/mL. In some embodiments, the composition is diluted prior to loading onto the chromatography material; for example, diluted 1:1, 1:2, 1:5, 1:10 or greater than 1:10. In some embodiments, the composition is diluted into the mobile phase of the chromatography. In some embodiments, the composition is diluted into a loading buffer.

In some embodiments of any of the methods described herein, the flow rate is more than about any of 0.5 mL/min, 0.6 mL/min, 0.7 mL/min, 0.8 mL/min, 0.9 mL/min, 1.0 mL/min, 1.1 mL/min, 1.2 mL/min, 1.3 mL/min, 1.4 mL/min, 1.5 mL/min, 1.75 mL/min and 2.0 mL/min.

In some embodiments of the methods described herein, the chromatography material is in a column. In some embodiments the column is an HPLC column. In some embodiments the column has any one of the following dimensions: 4×50 mm, 4×100 mm, 4×150 mm, 4×200 mm, 4×250 mm, or 2×250 mm.

In some embodiments of the invention, the methods are robust; i.e. one or more of the running parameters can be perturbed without affecting the analytical results (e.g. relative percentages of the main peak and the contaminant peaks). In some embodiments, the concentration of the buffer in the loading buffer and/or the elution buffer varies from any one of about 10 mM to 50 mM, 10 mM to 40 mM, 10 mM to 30 mM, 10 mM to 20 mM, 20 mM to 50 mM, 20 mM to 40 mM, 20 mM to 30 mM, 30 mM to 50 mM, 30 mM to 40 mM, or 40 mM to 50 mM. In some embodiments, the concentration of the buffer in the loading buffer and/or the elution buffer varies from about 10 mM to about 20 mM. In some embodiments, the first pH varies from any one of about pH 5.0 to pH 7.0, pH 5.0 to pH 6.5, pH 5.0 to pH 6.0, pH 5.0 to pH 5.5, pH 5.5 to pH 7.0, pH 5.5 to pH 6.5, pH 5.5 to pH 6.0, pH 6.0 to pH 7.0, pH 6.0 to pH 6.5 or pH 6.5 to pH 7.0. In some embodiments, the first pH varies from about pH 5.7 to about pH 6.3. In some embodiments, the temperature of the chromatography material varies from any one of about 20° C. to 50° C., 25° C. to 50° C., 30° C. to 50° C., 35° C. to 50° C., 40° C. to 50° C., 45° C. to 50° C., 20° C. to 45° C., 25° C. to 45° C., 30° C. to 45° C., 35° C. to 45° C., 40° C. to 45° C., 20° C. to 40° C., 25° C. to 40° C., 30° C. to 40° C., 35° C. to 40° C., 20° C. to 35° C., 25° C. to 35° C., 30° C. to 35° C., 20° C. to 30° C., 25° C. to 30° C., or 20° C. to 25° C. In some embodiments, the temperature of the chromatography material varies from about 36° C. to about 44° C. In some embodiments, the loading and elution are conducted at a flow rate varying from any one of about 0.5 ml/min to 2.0 ml/min, 0.8 ml/min to 2.0 ml/min, 1.0 ml/min to 2.0 ml/min, 1.2 ml/min to 2.0 ml/min, 1.5 ml/min to 2.0 ml/min, 1.8 ml/min to 2.0 ml/min, 0.5 ml/min to 1.8 ml/min, 0.8 ml/min to 1.8 ml/min, 1.0 ml/min to 1.8 ml/min, 1.2 ml/min to 1.8 ml/min, 1.5 ml/min to 1.8 ml/min, 0.5 ml/min to 1.5 ml/min, 0.8 ml/min to 1.5 ml/min, 1.0 ml/min to 1.5 ml/min, 1.2 ml/min to 1.5 ml/min, 0.5 ml/min to 1.2 ml/min, 0.8 ml/min to 1.2 ml/min, 1.0 ml/min to 1.2 ml/min, 0.5 ml/min to 1.0 ml/min, 0.8 ml/min to 1.0 ml/min, or 0.5 ml/min to 0.8 ml/min. In some embodiments, the loading and elution are conducted at a flow rate varying from about 0.8 ml/min to about 1.2 ml/min. In some embodiments, the loading and elution are conducted at a flow rate varying from about 1.5 ml/min to about 2.0 ml/min. In further embodiments, any combination of buffer concentration, starting pH, temperature of chromatography material and/or flow rate can vary according to the above embodiments.

Detection of Charge Variants

In some aspects, the invention provides methods of detecting variants of a polypeptide in a composition comprising the polypeptide and one or more variants in the composition of the polypeptide. The method comprising binding the polypeptide and one or more variants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is altered by an ionic strength gradient such that the polypeptides and the one or more contaminants elute from the chromatography material as distinct separate entities. The eluents of the chromatography are then analyzed for the parent polypeptide and the presence of variants. Variants of the polypeptide may include acidic variants of the polypeptide and basic variants of the parent polypeptide. Examples of acidic variants, i.e. variants with a pI less than the pI of the parent polypeptide, include but are not limited to polypeptides where one or more glutamine and/or asparagine residues have been deamidated. Examples of basic polypeptide variants, i.e. variants with a pI greater than the pI of the parent polypeptide, include but are not limited to variants where an aspartic acid residue has undergone modification to a succinimide moiety. In some embodiments, the methods of the invention are used to detect variants of a polypeptide in a composition comprising a polypeptide with an isoelectric point that is not in the neutral pH range. In some embodiments, the methods may be used to effectively detect charge variants in a composition comprising a polypeptide with a pI greater than 9 from contaminants. In some embodiments, a cation exchange chromatography material is used to effectively detect charge variants in a composition comprising a polypeptide with a pI greater than 9. In other embodiments, the methods may be used to effectively detect charge variants in a composition comprising a polypeptide with a pI less than 7 from contaminants. In some embodiments, an anion exchange chromatography material is used to effectively detect charge variants in a composition comprising a polypeptide with a pI less than 7. Examples of polypeptides include, but are not limited to, antibodies and antibody fragments.

In some aspects, the invention provides methods of detecting variants of a polypeptide in a composition comprising the polypeptide and one or more variants of the polypeptide. The method comprising binding the polypeptide and one or more variants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer remains essentially the same as the initial ionic strength such that the polypeptides and the one or more contaminants elute from the chromatography material as distinct separate entities. The eluents of the chromatography are then analyzed for the presence of the parent polypeptide and the presence of the variants. Variants of the polypeptide may include acidic variants of the polypeptide and basic variants of the parent polypeptide. Examples of acidic variants, i.e. variants with a pI less than the pI of the parent polypeptide, include but are not limited to polypeptides where one or more glutamine and/or asparagine residues have been deamidated. Examples of basic polypeptide variants, i.e. variants with a pI greater than the pI of the parent polypeptide, include but are not limited to variants where an aspartic acid residue has undergone modification to a succinimide moiety. In some embodiments, the methods of the invention are used to detect variants of a polypeptide in a composition comprising a polypeptide with an isoelectric point that is not in the neutral pH range. In some embodiments, the methods may be used to effectively detect charge variants in a composition comprising a polypeptide with a pI greater than 9. In some embodiments, a cation exchange chromatography material is used to effectively detect charge variants in a composition comprising a polypeptide with a pI greater than 9. In other embodiments, the methods may be used to effectively detect charge variants in a composition comprising a polypeptide with a pI less than 7. In some embodiments, an anion exchange chromatography material is used to effectively detect charge variants in a composition comprising a polypeptide with a pI less than 7. Examples of polypeptides include, but are not limited to, antibodies and antibody fragments. Determining the purity of a polypeptide in a composition In some aspects, the invention provides methods of determining the purity of a polypeptide in a composition comprising the polypeptide. The method comprising binding the polypeptide and one or more contaminants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is altered by an ionic strength gradient such that the polypeptides and the one or more contaminants elute from the chromatography material as distinct separate entities. The purity of the polypeptide can be assessed by determining the ratio of the amount of polypeptide eluting from the chromatography material to the total amount of contaminants, e.g. charge variants, eluting from the chromatography material. In some embodiments, the methods of the invention are used to determine the purity of a polypeptide in a composition comprising a polypeptide with an isoelectric point that is not in the neutral pH range. In some embodiments, the methods may be used to effectively determine the purity of a polypeptide in a composition comprising a polypeptide with a pI greater than 9 from contaminants. In some embodiments, a cation exchange chromatography material is used to effectively determine the purity of a polypeptide in a composition comprising a polypeptide with a pI greater than 9. In other embodiments, the methods may be used to effectively determine the purity of a polypeptide in a composition comprising a polypeptide with a pI less than 7 from contaminants. In some embodiments, an anion exchange chromatography material is used to effectively determine the purity of a polypeptide in a composition comprising a polypeptide with a pI less than 7. Examples of polypeptides include, but are not limited to, antibodies and antibody fragments.

In some aspects, the invention provides methods of determining the purity of a polypeptide in a composition comprising the polypeptide. The method comprising binding the polypeptide and one or more contaminants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer remains essentially the same as the initial ionic strength such that the polypeptides and the one or more contaminants elute from the chromatography material as distinct separate entities. The purity of the polypeptide can be assessed by determining the ratio of the amount of polypeptide eluting from the chromatography material to the total amount of contaminants, e.g. charge variants, eluting from the chromatography material. In some embodiments, the methods of the invention are used to determine the purity of a polypeptide in a composition comprising a polypeptide with an isoelectric point that is not in the neutral pH range. In some embodiments, the methods may be used to effectively determine the purity of a polypeptide in a composition comprising a polypeptide with a pI greater than 9 from contaminants. In some embodiments, a cation exchange chromatography material is used to effectively determine the purity of a polypeptide in a composition comprising a polypeptide with a pI greater than 9. In other embodiments, the methods may be used to effectively determine the purity of a polypeptide in a composition comprising a polypeptide with a pI less than 7 from contaminants. In some embodiments, an anion exchange chromatography material is used to effectively determine the purity of a polypeptide in a composition comprising a polypeptide with a pI less than 7. Examples of polypeptides include, but are not limited to, antibodies and antibody fragments. Determining the stability of a polypeptide in a composition In some aspects, the invention provides methods for determining the stability of a polypeptide in a composition comprising the polypeptide. In some embodiments, samples of the composition comprising the polypeptide are analyzed over time. In some embodiments, the composition is incubated at various times before analysis. In some embodiments, the composition is incubated at more than any one of about 0° C., 20° C., 37° C. or 40° C. prior to analysis. In some embodiments, the composition is incubated for one or more of 1 day, 2 days, 3 days, 5 days, 1 week, 2 weeks, 3 weeks, 4 weeks, 6 weeks, 2 months, 3 months, 6 months, 1 year prior to analysis. The composition is then analyzed by binding the polypeptide and one or more contaminants in the composition to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is altered by an ionic strength gradient such that the polypeptides and the one or more contaminants elute from the chromatography material as distinct separate entities. In other embodiments, the composition is analyzed by binding the polypeptide and one or more contaminants in the composition to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer remains essentially the same as the initial ionic strength such that the polypeptides and the one or more contaminants elute from the chromatography material as distinct separate entities. For either of the above embodiments, the change in the ratio of polypeptide to contaminants indicates the stability of the polypeptide in the composition. For example, if the ratio of polypeptide to contaminants does not change over time, the polypeptide may be considered stable whereas the rapid accumulation of contaminants with a concomitant decrease in the amount of protein in the composition indicates the polypeptide in the composition is less stable. In some embodiments, the methods of the invention are used to determine the stability of a polypeptide in a composition comprising a polypeptide with an isoelectric point that is not in the neutral pH range. In some embodiments, the methods may be used to effectively determine the stability of a polypeptide in a composition comprising a polypeptide with a pI greater than 9 from contaminants. In some embodiments, a cation exchange chromatography material is used to determine the stability of a polypeptide in a composition comprising a polypeptide with a pI greater than 9. In other embodiments, the methods may be used to determine the stability of a polypeptide in a composition comprising a polypeptide with a pI less than 7 from contaminants. In some embodiments, an anion exchange chromatography material is used to determine the stability of a polypeptide in a composition comprising a polypeptide with a pI less than 7. Examples of polypeptides include, but are not limited to, antibodies and antibody fragments.

Purification of Polypeptides

In some aspects, the invention provides methods of purifying a polypeptide from a composition comprising the polypeptide and one or more variants of the polypeptide. The method comprising binding the polypeptide and one or more variants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is altered by an ionic strength gradient such that the polypeptides and the one or more contaminants elute from the chromatography material as distinct separate entities. Fractions are collected during the elution phase of the chromatography and fractions that contain polypeptide with no or minimal contaminants are pooled for further processing or for pharmaceutical formulation. In some embodiments, the methods of the invention are used purify a polypeptide in a composition comprising a polypeptide with an isoelectric point that is not in the neutral pH range. In some embodiments, the methods may be used to purify a polypeptide with a pI greater than 9. In some embodiments, a cation exchange chromatography material is used to purify a polypeptide with a pI greater than 9. In other embodiments, the methods may be used to purify a polypeptide with a pI less than 7 from contaminants. In some embodiments, an anion exchange chromatography material is used to purify a polypeptide with a pI less than 7. Examples of polypeptides include, but are not limited to, antibodies and antibody fragments.

In some aspects, the invention provides methods of purifying a polypeptide from a composition comprising the polypeptide and one or more variants of the polypeptide. The method comprising binding the polypeptide and one or more variants to a ion exchange chromatography material using a loading buffer with an initial pH and an initial ionic strength, eluting the polypeptide and one or more contaminants from the ion-exchange column using an elution buffer wherein the pH of the elution buffer is altered by a pH gradient and the ionic strength of the elution buffer is essentially the same as the initial ionic strength such that the polypeptides and the one or more contaminants elute from the chromatography material as distinct separate entities. Fractions are collected during the elution phase of the chromatography and fractions that contain polypeptide but not the contaminants are pooled for further processing or for pharmaceutical formulation. In some embodiments, the methods of the invention are used purify a polypeptide in a composition comprising a polypeptide with an isoelectric point that is not in the neutral pH range. In some embodiments, the methods may be used to purify a polypeptide with a pI greater than 9. In some embodiments, a cation exchange chromatography material is used to purify a polypeptide with a pI greater than 9. In other embodiments, the methods may be used to purify a polypeptide with a pI less than 7 from contaminants. In some embodiments, an anion exchange chromatography material is used to purify a polypeptide with a pI less than 7. Examples of polypeptides include, but are not limited to, antibodies and antibody fragments.

III. Polypeptides

Polypeptides are provided for use in any of the methods of ionic-strength-mediated pH gradient ion exchange chromatography described herein. In some embodiments of the invention, compositions of a polypeptide are analyzed by ionic strength mediated pH gradient ion exchange chromatography. Such methods are useful in identifying charge variants of the polypeptide within the composition. In some embodiments, the polypeptide is an antibody or fragment thereof.

In some embodiments, the polypeptide is a therapeutic polypeptide. The therapeutic polypeptide may inhibit the growth of tumor cells, induce apoptosis, and/or induce cell death. In some embodiments, the polypeptide is an antagonist. In some embodiments, the polypeptide is an agonist. In some embodiments, the polypeptide is an antibody. In some embodiments, the polypeptide is an immunoadhesin.

In some embodiments, the polypeptide has a molecular weight of greater than about any of 5,000 Daltons, 10,000 Daltons, 15,000 Daltons, 25,000 Daltons, 50,000 Daltons, 75,000 Daltons, 100,000 Dalton, 125,000 Daltons, or 150,000 Daltons. The polypeptide may have a molecular weight between about any of 50,000 Daltons to 200,000 Daltons or 100,000 Daltons to 200,000 Daltons. Alternatively, the polypeptide for use herein may have a molecular weight of about 120,000 Daltons or about 25,000 Daltons.

pI is the isoelectric point and is the pH at which a particular molecule or surface carries no net electrical charge. In some embodiments of any of the methods described herein, the pI of the polypeptide, e.g. an antibody, may be greater that about 9. In some embodiments, the polypeptide has a pI of about any of 9, 9.5, 10, 10.5, 11, 11.5, or 12. In some embodiments, the polypeptide has a pI between about 9 and 12. In some embodiments, the polypeptide has a pI between about 9 and 11. In some embodiments, the polypeptide has a pI between about 9 and 10. In some embodiments, the polypeptide has a pI between about 10 and 12. In some embodiments, the polypeptide has a pI between about 10 and 11. In some embodiments, the polypeptide has a pI between about 11 and 12.

In some embodiments of any of the methods described herein, the pI of the polypeptide, e.g. an antibody, may be less that about 7. In some embodiments, the polypeptide has a pI of about any of 7, 6.5, 6, 5.5, 5, 4.5, or 4. In some embodiments, the polypeptide has a pI between about 4 and 7. In some embodiments, the polypeptide has a pI between about 4 and 6. In some embodiments, the polypeptide has a pI between about 4 and 5. In some embodiments, the polypeptide has a pI between about 5 and 7. In some embodiments, the polypeptide has a pI between about 5 and 6.

In embodiments of any of the methods described herein, the one or more contaminants in a composition comprising a polypeptide and one or more contaminants are polypeptide charge variants. In some embodiments, the polypeptide charge variant is a polypeptide that has been modified from its native state such that the charge of the polypeptide is altered. In some embodiments, the charge variants are more acidic than the parent polypeptide; i.e. have a lower pI than the parent polypeptide. In other embodiments, the charge variants are more basic than the parent polypeptide; i.e. have a higher pI than the parent polypeptide. In some embodiments, the polypeptide charge variants are engineered. In some embodiments, the polypeptide charge variant is the result of natural processes; for example, oxidation, deamidation, C-terminal processing of lysine residues, N-terminal pyroglutamate formation, and glycation. In some embodiments, the polypeptide charge variant is a glycoprotein where the glycan attached to the protein is modified such that the charge of the glycoprotein is altered compared to parent glycoprotein; for example, by addition of sialic acid or its derivatives. In some embodiments, the polypeptide charge variant is an antibody charge variant.

The polypeptides to be analyzed using the methods described herein is generally produced using recombinant techniques. Methods for producing recombinant proteins are described, e.g., in U.S. Pat. Nos. 5,534,615 and 4,816,567, specifically incorporated herein by reference. In some embodiments, the protein of interest is produced in a CHO cell (see, e.g. WO 94/11026). When using recombinant techniques, the polypeptides can be produced intracellularly, in the periplasmic space, or directly secreted into the medium.

The polypeptides may be recovered from culture medium or from host cell lysates. Cells employed in expression of the polypeptides can be disrupted by various physical or chemical means, such as freeze-thaw cycling, sonication, mechanical disruption, or cell lysing agents. If the polypeptide is produced intracellularly, as a first step, the particulate debris, either host cells or lysed fragments, are removed, for example, by centrifugation or ultrafiltration. Carter et al., *Bio/Technology* 10: 163-167 (1992) describe a procedure for isolating polypeptides which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the polypeptide is secreted into the medium, supernatants from such expression systems are generally first concentrated using a commercially available polypeptide concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

In some embodiments, the polypeptide in the composition comprising the polypeptide and one or more contaminants has been purified or partially purified prior to analysis by the methods of the invention. For example, the polypeptide of the methods is in an eluent from an affinity chromatography, a cation exchange chromatography, an anion exchange chromatography, a mixed mode chromatography and a hydrophobic interaction chromatography. In some embodiments, the polypeptide is in an eluent from a Protein A chromatography.

Examples of polypeptides that may be analyzed by the methods of the invention include but are not limited to immunoglobulins, immunoadhesins, antibodies, enzymes, hormones, fusion proteins, Fc-containing proteins, immunoconjugates, cytokines and interleukins.

In some embodiments, the polypeptide is in a pharmaceutical composition. In some embodiments the polypeptide is an antibody, or antigen binding fragment thereof, in a pharmaceutical composition. In some embodiments, the pharmaceutical composition comprises the polypeptide and a pharmaceutically acceptable carrier including, but not limited to, a buffer, excipient, stabilizer, or preservative. In some embodiments, the pharmaceutical composition comprises an antibody, or antigen binding fragment thereof, and a pharmaceutically acceptable carrier including, but not limited to, a buffer, excipient, stabilizer, or preservative.

(A) Antibodies

In some embodiments of any of the methods described herein, the polypeptide for use in any of the methods of analyzing polypeptides and formulations comprising the polypeptides by the methods described herein is an antibody.

Molecular targets for antibodies include CD proteins and their ligands, such as, but not limited to: (i) CD3, CD4, CD8, CD19, CD11a, CD20, CD22, CD34, CD40, CD79α (CD79a), and CD79β (CD79b); (ii) members of the ErbB receptor family such as the EGF receptor, HER2, HER3 or HER4 receptor; (iii) cell adhesion molecules such as LFA-1, Mac1, p150, 95, VLA-4, ICAM-1, VCAM and αv/β3 integrin, including either alpha or beta subunits thereof (e.g., anti-CD11a, anti-CD18 or anti-CD11b antibodies); (iv) growth factors such as VEGF; IgE; blood group antigens; flk2/flt3 receptor; obesity (OB) receptor; mpl receptor; CTLA-4; protein C, BR3, c-met, tissue factor, β7 etc; and (v) cell surface and transmembrane tumor-associated antigens (TAA), such as those described in U.S. Pat. No. 7,521,541.

Other exemplary antibodies include those selected from, and without limitation, anti-estrogen receptor antibody, anti-progesterone receptor antibody, anti-p53 antibody, anti-HER-2/neu antibody, anti-EGFR antibody, anti-cathepsin D antibody, anti-Bcl-2 antibody, anti-E-cadherin antibody, anti-CA125 antibody, anti-CA15-3 antibody, anti-CA19-9 antibody, anti-c-erbB-2 antibody, anti-P-glycoprotein antibody, anti-CEA antibody, anti-retinoblastoma protein antibody, anti-ras oncoprotein antibody, anti-Lewis X antibody, anti-Ki-67 antibody, anti-PCNA antibody, anti-CD3 antibody, anti-CD4 antibody, anti-CD5 antibody, anti-CD7 antibody, anti-CD8 antibody, anti-CD9/p24 antibody, anti-CD10 antibody, anti-CD11a antibody, anti-CD11c antibody, anti-CD13 antibody, anti-CD14 antibody, anti-CD15 antibody, anti-CD19 antibody, anti-CD20 antibody, anti-CD22 antibody, anti-CD23 antibody, anti-CD30 antibody, anti-CD31 antibody, anti-CD33 antibody, anti-CD34 antibody, anti-CD35 antibody, anti-CD38 antibody, anti-CD41 antibody, anti-LCA/CD45 antibody, anti-CD45RO antibody, anti-CD45RA antibody, anti-CD39 antibody, anti-CD100 antibody, anti-CD95/Fas antibody, anti-CD99 antibody, anti-CD106 antibody, anti-ubiquitin antibody, anti-CD71 antibody, anti-c-myc antibody, anti-cytokeratins antibody, anti-vimentins antibody, anti-HPV proteins antibody, anti-kappa light chains antibody, anti-lambda light chains antibody, anti-melanosomes antibody, anti-prostate specific antigen antibody, anti-S-100 antibody, anti-tau antigen antibody, anti-fibrin antibody, anti-keratins antibody and anti-Tn-antigen antibody.

(i) Monoclonal Antibodies

In some embodiments, the antibodies are monoclonal antibodies. Monoclonal antibodies are obtained from a population of substantially homogeneous antibodies, i.e., the individual antibodies comprising the population are identical and/or bind the same epitope except for possible variants that arise during production of the monoclonal antibody, such variants generally being present in minor amounts. Thus, the modifier "monoclonal" indicates the character of the antibody as not being a mixture of discrete or polyclonal antibodies.

For example, the monoclonal antibodies may be made using the hybridoma method first described by Kohler et al., Nature 256:495 (1975), or may be made by recombinant DNA methods (U.S. Pat. No. 4,816,567).

In the hybridoma method, a mouse or other appropriate host animal, such as a hamster, is immunized as herein described to elicit lymphocytes that produce or are capable of producing antibodies that will specifically bind to the polypeptide used for immunization. Alternatively, lymphocytes may be immunized in vitro. Lymphocytes then are fused with myeloma cells using a suitable fusing agent, such as polyethylene glycol, to form a hybridoma cell (Goding, Monoclonal Antibodies: Principles and Practice, pp. 59-103 (Academic Press, 1986)).

The hybridoma cells thus prepared are seeded and grown in a suitable culture medium that preferably contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

In some embodiments, the myeloma cells are those that fuse efficiently, support stable high-level production of antibody by the selected antibody-producing cells, and are sensitive to a medium such as HAT medium. Among these, in some embodiments, the myeloma cell lines are murine myeloma lines, such as those derived from MOPC-21 and MPC-11 mouse tumors available from the Salk Institute Cell Distribution Center, San Diego, Calif. USA, and SP-2 or X63-Ag8-653 cells available from the American Type Culture Collection, Rockville, Md. USA. Human myeloma and mouse-human heteromyeloma cell lines also have been described for the production of human monoclonal antibodies (Kozbor, J. Immunol. 133:3001 (1984); Brodeur et al., Monoclonal Antibody Production Techniques and Applications pp. 51-63 (Marcel Dekker, Inc., New York, 1987)).

Culture medium in which hybridoma cells are growing is assayed for production of monoclonal antibodies directed against the antigen. In some embodiments, the binding specificity of monoclonal antibodies produced by hybridoma cells is determined by immunoprecipitation or by an in vitro binding assay, such as radioimmunoassay (RIA) or enzyme-linked immunoabsorbent assay (ELISA).

The binding affinity of the monoclonal antibody can, for example, be determined by the Scatchard analysis of Munson et al., Anal. Biochem. 107:220 (1980).

After hybridoma cells are identified that produce antibodies of the desired specificity, affinity, and/or activity, the clones may be subcloned by limiting dilution procedures and grown by standard methods (Goding, Monoclonal Antibodies: Principles and Practice pp. 59-103 (Academic Press, 1986)). Suitable culture media for this purpose include, for example, D-MEM or RPMI-1640 medium. In addition, the hybridoma cells may be grown in vivo as ascites tumors in an animal.

The monoclonal antibodies secreted by the subclones are suitably separated from the culture medium, ascites fluid, or serum by conventional immunoglobulin purification procedures such as, for example, polypeptide A-Sepharose, hydroxylapatite chromatography, gel electrophoresis, dialysis, or affinity chromatography.

DNA encoding the monoclonal antibodies is readily isolated and sequenced using conventional procedures (e.g., by using oligonucleotide probes that are capable of binding specifically to genes encoding the heavy and light chains of murine antibodies). In some embodiments, the hybridoma cells serve as a source of such DNA. Once isolated, the DNA may be placed into expression vectors, which are then transfected into host cells such as E. coli cells, simian COS cells, Chinese Hamster Ovary (CHO) cells, or myeloma cells that do not otherwise produce immunoglobulin polypeptide, to obtain the synthesis of monoclonal antibodies in the recombinant host cells. Review articles on recombinant expression in bacteria of DNA encoding the antibody include Skerra et al., Curr. Opinion in Immunol. 5:256-262 (1993) and Plückthun, Immunol. Revs., 130:151-188 (1992).

In a further embodiment, antibodies or antibody fragments can be isolated from antibody phage libraries generated using the techniques described in McCafferty et al., Nature 348:552-554 (1990). Clackson et al., Nature 352: 624-628 (1991) and Marks et al., J. Mol. Biol. 222:581-597 (1991) describe the isolation of murine and human antibodies, respectively, using phage libraries. Subsequent publications describe the production of high affinity (nM range) human antibodies by chain shuffling (Marks et al., Bio/Technology 10:779-783 (1992)), as well as combinatorial infection and in vivo recombination as a strategy for constructing very large phage libraries (Waterhouse et al., Nuc. Acids. Res. 21:2265-2266 (1993)). Thus, these techniques are viable alternatives to traditional monoclonal antibody hybridoma techniques for isolation of monoclonal antibodies.

The DNA also may be modified, for example, by substituting the coding sequence for human heavy- and light chain constant domains in place of the homologous murine sequences (U.S. Pat. No. 4,816,567; Morrison et al., Proc. Natl Acad. Sci. USA 81:6851 (1984)), or by covalently joining to the immunoglobulin coding sequence all or part of the coding sequence for a non-immunoglobulin polypeptide.

Typically such non-immunoglobulin polypeptides are substituted for the constant domains of an antibody, or they are substituted for the variable domains of one antigen-combining site of an antibody to create a chimeric bivalent antibody comprising one antigen-combining site having specificity for an antigen and another antigen-combining site having specificity for a different antigen.

In some embodiments of any of the methods described herein, the antibody is IgA, IgD, IgE, IgG, or IgM. In some embodiments, the antibody is an IgG monoclonal antibody.

(ii) Humanized Antibodies

In some embodiments, the antibody is a humanized antibody. Methods for humanizing non-human antibodies have been described in the art. In some embodiments, a humanized antibody has one or more amino acid residues introduced into it from a source that is non-human. These non-human amino acid residues are often referred to as "import" residues, which are typically taken from an "import" variable domain. Humanization can be essentially performed following the method of Winter and co-workers (Jones et al., Nature 321:522-525 (1986); Riechmann et al., Nature 332:323-327 (1988); Verhoeyen et al., Science 239: 1534-1536 (1988)), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies is very important to reduce antigenicity. According to the so-called "best-fit" method, the sequence of the variable domain of a rodent antibody is screened against the entire library of known human variable-domain sequences. The human sequence that is closest to that of the rodent is then accepted as the human framework region (FR) for the humanized antibody (Sims et al., *J. Immunol.* 151:2296 (1993); Chothia et al., *J. Mol. Biol.* 196:901 (1987)). Another method uses a particular framework region derived from the consensus sequence of all human antibodies of a particular subgroup of light or heavy chain variable regions. The same framework may be used for several different humanized antibodies (Carter et al., *Proc. Natl. Acad. Sci. USA* 89:4285 (1992); Presta et al., *J. Immunol.* 151:2623 (1993)).

It is further important that antibodies be humanized with retention of high affinity for the antigen and other favorable biological properties. To achieve this goal, in some embodiments of the methods, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available that illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

(iii) Human Antibodies

In some embodiments, the antibody is a human antibody. As an alternative to humanization, human antibodies can be generated. For example, it is now possible to produce transgenic animals (e.g., mice) that are capable, upon immunization, of producing a full repertoire of human antibodies in the absence of endogenous immunoglobulin production. For example, it has been described that the homozygous deletion of the antibody heavy chain joining region ($J_H$) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., *Proc. Natl. Acad. Sci. USA* 90:2551 (1993); Jakobovits et al., *Nature* 362:255-258 (1993); Bruggermann et al., *Year in Immuno.* 7:33 (1993); and U.S. Pat. Nos. 5,591,669; 5,589,369; and 5,545,807.

Alternatively, phage display technology (McCafferty et al., *Nature* 348:552-553 (1990)) can be used to produce human antibodies and antibody fragments in vitro, from immunoglobulin variable (V) domain gene repertoires from unimmunized donors. According to this technique, antibody V domain genes are cloned in-frame into either a major or minor coat polypeptide gene of a filamentous bacteriophage, such as M13 or fd, and displayed as functional antibody fragments on the surface of the phage particle. Because the filamentous particle contains a single-stranded DNA copy of the phage genome, selections based on the functional properties of the antibody also result in selection of the gene encoding the antibody exhibiting those properties. Thus, the phage mimics some of the properties of the B cell. Phage display can be performed in a variety of formats; for their review see, e.g., Johnson, Kevin S. and Chiswell, David J., *Current Opinion in Structural Biology* 3:564-571 (1993). Several sources of V-gene segments can be used for phage display. Clackson et al., *Nature* 352:624-628 (1991) isolated a diverse array of anti-oxazolone antibodies from a small random combinatorial library of V genes derived from the spleens of immunized mice. A repertoire of V genes from unimmunized human donors can be constructed and antibodies to a diverse array of antigens (including self-antigens) can be isolated essentially following the techniques described by Marks et al., *J. Mol. Biol.* 222:581-597 (1991), or Griffith et al., *EMBO J.* 12:725-734 (1993). See also, U.S. Pat. Nos. 5,565,332 and 5,573,905.

Human antibodies may also be generated by in vitro activated B cells (see U.S. Pat. Nos. 5,567,610 and 5,229, 275).

(iv) Antibody Fragments

In some embodiments, the antibody is an antibody fragment. Various techniques have been developed for the production of antibody fragments. Traditionally, these fragments were derived via proteolytic digestion of intact antibodies (see, e.g., Morimoto et al., *Journal of Biochemical and Biophysical Methods* 24:107-117 (1992) and Brennan et al., *Science* 229:81 (1985)). However, these fragments can now be produced directly by recombinant host cells. For example, the antibody fragments can be isolated from the antibody phage libraries discussed above. Alternatively, Fab'-SH fragments can be directly recovered from *E. coli* and chemically coupled to form $F(ab')_2$ fragments (Carter et al., *Bio/Technology* 10:163-167 (1992)). According to another approach, $F(ab')_2$ fragments can be isolated directly from recombinant host cell culture. Other techniques for the production of antibody fragments will be apparent to the skilled practitioner. In other embodiments, the antibody of choice is a single chain Fv fragment (scFv). See WO 93/16185; U.S. Pat. No. 5,571,894; and U.S. Pat. No. 5,587,458. The antibody fragment may also be a "linear antibody," e.g., as described in U.S. Pat. No. 5,641,870 for example. Such linear antibody fragments may be monospecific or bispecific.

In some embodiments, fragments of the antibodies described herein are provided. In some embodiments, the antibody fragment is an antigen binding fragment. In some embodiments, the antigen binding fragment is selected from the group consisting of a Fab fragment, a Fab' fragment, a $F(ab')_2$ fragment, a scFv, a Fv, and a diabody.

(v) Bispecific Antibodies

In some embodiments, the antibody is a bispecific antibody. Bispecific antibodies are antibodies that have binding specificities for at least two different epitopes. Exemplary bispecific antibodies may bind to two different epitopes. Alternatively, a bispecific antibody binding arm may be combined with an arm that binds to a triggering molecule on a leukocyte such as a T-cell receptor molecule (e.g. CD2 or CD3), or Fc receptors for IgG (FcγR), such as FcγRI (CD64), FcγRII (CD32) and FcγRIII (CD16) so as to focus cellular defense mechanisms to the cell. Bispecific antibodies can be prepared as full length antibodies or antibody fragments (e.g. F(ab')$_2$ bispecific antibodies).

Methods for making bispecific antibodies are known in the art. Traditional production of full length bispecific antibodies is based on the coexpression of two immunoglobulin heavy chain-light chain pairs, where the two chains have different specificities (Millstein et al., *Nature* 305:537-539 (1983)). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., *EMBO J.*, 10:3655-3659 (1991).

According to a different approach, antibody variable domains with the desired binding specificities (antibody-antigen combining sites) are fused to immunoglobulin constant domain sequences. In some embodiments, the fusion is with an immunoglobulin heavy chain constant domain, comprising at least part of the hinge, CH2, and CH3 regions. In some embodiments, the first heavy chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In some embodiments of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., *Methods in Enzymology* 121:210 (1986).

According to another approach described in U.S. Pat. No. 5,731,168, the interface between a pair of antibody molecules can be engineered to maximize the percentage of heterodimers that are recovered from recombinant cell culture. In some embodiments, the interface comprises at least a part of the C$_H$3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Techniques for generating bispecific antibodies from antibody fragments have also been described in the literature. For example, bispecific antibodies can be prepared using chemical linkage. Brennan et al., *Science* 229: 81 (1985) describe a procedure wherein intact antibodies are proteolytically cleaved to generate F(ab')$_2$ fragments. These fragments are reduced in the presence of the dithiol complexing agent sodium arsenite to stabilize vicinal dithiols and prevent intermolecular disulfide formation. The Fab' fragments generated are then converted to thionitrobenzoate (TNB) derivatives. One of the Fab'-TNB derivatives is then reconverted to the Fab'-thiol by reduction with mercaptoethylamine and is mixed with an equimolar amount of the other Fab'-TNB derivative to form the bispecific antibody. The bispecific antibodies produced can be used as agents for the selective immobilization of enzymes.

Various techniques for making and isolating bispecific antibody fragments directly from recombinant cell culture have also been described. For example, bispecific antibodies have been produced using leucine zippers. Kostelny et al., *J. Immunol.* 148(5):1547-1553 (1992). The leucine zipper peptides from the Fos and Jun proteins were linked to the Fab' portions of two different antibodies by gene fusion. The antibody homodimers were reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy chain variable domain (V$_H$) connected to a light chain variable domain (V$_L$) by a linker that is too short to allow pairing between the two domains on the same chain. Accordingly, the V$_H$ and V$_L$ domains of one fragment are forced to pair with the complementary V$_L$ and V$_H$ domains of another fragment, thereby forming two antigen-binding sites. Another strategy for making bispecific antibody fragments by the use of single-chain Fv (sFv) dimers has also been reported. See Gruber et al., *J. Immunol.* 152:5368 (1994).

Antibodies with more than two valencies are contemplated. For example, trispecific antibodies can be prepared. Tutt et al., *J. Immunol.* 147: 60 (1991).

(v) Multivalent Antibodies

In some embodiments, the antibodies are multivalent antibodies. A multivalent antibody may be internalized (and/or catabolized) faster than a bivalent antibody by a cell expressing an antigen to which the antibodies bind. The antibodies provided herein can be multivalent antibodies (which are other than of the IgM class) with three or more antigen binding sites (e.g., tetravalent antibodies), which can be readily produced by recombinant expression of nucleic acid encoding the polypeptide chains of the antibody. The multivalent antibody can comprise a dimerization domain and three or more antigen binding sites. The preferred dimerization domain comprises (or consists of) an Fc region or a hinge region. In this scenario, the antibody will comprise an Fc region and three or more antigen binding sites amino-terminal to the Fc region. The preferred multivalent antibody herein comprises (or consists of) three to about eight, but preferably four, antigen binding sites. The multivalent antibody comprises at least one polypeptide chain (and preferably two polypeptide chains), wherein the polypeptide chain(s) comprise two or more variable domains. For instance, the polypeptide chain(s) may comprise VD1-(X1)n-VD2-(X2) n-Fc, wherein VD1 is a first variable domain, VD2 is a second variable domain, Fc is one polypeptide chain of an Fc region, X1 and X2 represent an amino acid or polypeptide, and n is 0 or 1. For instance, the polypeptide chain(s) may comprise: VH-CH1-flexible linker-VH-CH1-Fc region chain; or VH-CH1-VH-CH1-Fc region chain. The multivalent antibody herein preferably further comprises at least two (and preferably four) light chain variable domain polypeptides. The multivalent antibody herein may, for instance, comprise from about two to about eight light chain variable domain polypeptides. The light chain variable domain polypeptides contemplated here comprise a light chain variable domain and, optionally, further comprise a CL domain.

In some embodiments, the antibody is a multispecific antibody. Example of multispecific antibodies include, but are not limited to, an antibody comprising a heavy chain variable domain ($V_H$) and a light chain variable domain ($V_L$), where the $V_HV_L$ unit has polyepitopic specificity, antibodies having two or more $V_L$ and $V_H$ domains with each $V_HV_L$ unit binding to a different epitope, antibodies having two or more single variable domains with each single variable domain binding to a different epitope, full length antibodies, antibody fragments such as Fab, Fv, dsFv, scFv, diabodies, bispecific diabodies, triabodies, tri-functional antibodies, antibody fragments that have been linked covalently or non-covalently. In some embodiment that antibody has polyepitopic specificity; for example, the ability to specifically bind to two or more different epitopes on the same or different target(s). In some embodiments, the antibodies are monospecific; for example, an antibody that binds only one epitope. According to one embodiment the multispecific antibody is an IgG antibody that binds to each epitope with an affinity of 5 µM to 0.001 pM, 3 µM to 0.001 pM, 1 µM to 0.001 pM, 0.5 µM to 0.001 pM, or 0.1 µM to 0.001 pM.

(vi) Other Antibody Modifications

It may be desirable to modify the antibody provided herein with respect to effector function, e.g., so as to enhance antigen-dependent cell-mediated cyotoxicity (ADCC) and/or complement dependent cytotoxicity (CDC) of the antibody. This may be achieved by introducing one or more amino acid substitutions in an Fc region of the antibody. Alternatively or additionally, cysteine residue(s) may be introduced in the Fc region, thereby allowing interchain disulfide bond formation in this region. The homodimeric antibody thus generated may have improved internalization capability and/or increased complement-mediated cell killing and antibody-dependent cellular cytotoxicity (ADCC). See Caron et al., *J. Exp Med.* 176:1191-1195 (1992) and Shopes, B. J., *Immunol.* 148:2918-2922 (1992). Homodimeric antibodies with enhanced anti-tumor activity may also be prepared using heterobifunctional cross-linkers as described in Wolff et al., *Cancer Research* 53:2560-2565 (1993). Alternatively, an antibody can be engineered which has dual Fc regions and may thereby have enhanced complement mediated lysis and ADCC capabilities. See Stevenson et al., *Anti-Cancer Drug Design* 3:219-230 (1989).

For increasing serum half the serum half life of the antibody, amino acid alterations can be made in the antibody as described in US 2006/0067930, which is hereby incorporated by reference in its entirety.

(B) Polypeptide Variants and Modifications

Amino acid sequence modification(s) of the polypeptides, including antibodies, described herein may be used in the methods of purifying polypeptides (e.g., antibodies) described herein.

(i) Variant Polypeptides

"Polypeptide variant" means a polypeptide, preferably an active polypeptide, as defined herein having at least about 80% amino acid sequence identity with a full-length native sequence of the polypeptide, a polypeptide sequence lacking the signal peptide, an extracellular domain of a polypeptide, with or without the signal peptide. Such polypeptide variants include, for instance, polypeptides wherein one or more amino acid residues are added, or deleted, at the N or C-terminus of the full-length native amino acid sequence. Ordinarily, a TAT polypeptide variant will have at least about 80% amino acid sequence identity, alternatively at least about any of 85%, 90%, 95%, 96%, 97%, 98%, or 99% amino acid sequence identity, to a full-length native sequence polypeptide sequence, a polypeptide sequence lacking the signal peptide, an extracellular domain of a polypeptide, with or without the signal peptide. Optionally, variant polypeptides will have no more than one conservative amino acid substitution as compared to the native polypeptide sequence, alternatively no more than about any of 2, 3, 4, 5, 6, 7, 8, 9, or 10 conservative amino acid substitution as compared to the native polypeptide sequence.

The variant polypeptide may be truncated at the N-terminus or C-terminus, or may lack internal residues, for example, when compared with a full length native polypeptide. Certain variant polypeptides may lack amino acid residues that are not essential for a desired biological activity. These variant polypeptides with truncations, deletions, and insertions may be prepared by any of a number of conventional techniques. Desired variant polypeptides may be chemically synthesized. Another suitable technique involves isolating and amplifying a nucleic acid fragment encoding a desired variant polypeptide, by polymerase chain reaction (PCR). Oligonucleotides that define the desired termini of the nucleic acid fragment are employed at the 5' and 3' primers in the PCR. Preferably, variant polypeptides share at least one biological and/or immunological activity with the native polypeptide disclosed herein.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to a cytotoxic polypeptide. Other insertional variants of the antibody molecule include the fusion to the N- or C-terminus of the antibody to an enzyme or a polypeptide which increases the serum half-life of the antibody.

For example, it may be desirable to improve the binding affinity and/or other biological properties of the polypeptide. Amino acid sequence variants of the polypeptide are prepared by introducing appropriate nucleotide changes into the antibody nucleic acid, or by peptide synthesis. Such modifications include, for example, deletions from, and/or insertions into and/or substitutions of, residues within the amino acid sequences of the polypeptide. Any combination of deletion, insertion, and substitution is made to arrive at the final construct, provided that the final construct possesses the desired characteristics. The amino acid changes also may alter post-translational processes of the polypeptide (e.g., antibody), such as changing the number or position of glycosylation sites.

Guidance in determining which amino acid residue may be inserted, substituted or deleted without adversely affecting the desired activity may be found by comparing the sequence of the polypeptide with that of homologous known polypeptide molecules and minimizing the number of amino acid sequence changes made in regions of high homology.

A useful method for identification of certain residues or regions of the polypeptide (e.g., antibody) that are preferred locations for mutagenesis is called "alanine scanning mutagenesis" as described by Cunningham and Wells, *Science* 244:1081-1085 (1989). Here, a residue or group of target residues are identified (e.g., charged residues such as Arg, Asp, His, Lys, and Glu) and replaced by a neutral or negatively charged amino acid (most preferably Alanine or Polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed antibody variants are screened for the desired activity.

Another type of variant is an amino acid substitution variant. These variants have at least one amino acid residue in the antibody molecule replaced by a different residue. The sites of greatest interest for substitutional mutagenesis include the hypervariable regions, but FR alterations are also contemplated. Conservative substitutions are shown in the Table 1 below under the heading of "preferred substitutions." If such substitutions result in a change in biological activity, then more substantial changes, denominated "exemplary substitutions" in the Table 1, or as further described below in reference to amino acid classes, may be introduced and the products screened.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the polypeptide are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Amino acids may be grouped according to similarities in the properties of their side chains (in A. L. Lehninger, *Biochemistry* second ed., pp. 73-75, Worth Publishers, New York (1975)):
(1) non-polar: Ala (A), Val (V), Leu (L), Ile (I), Pro (P), Phe (F), Trp (W), Met (M)
(2) uncharged polar: Gly (G), Ser (S), Thr (T), Cys (C), Tyr (Y), Asn (N), Gln (Q)
(3) acidic: Asp (D), Glu (E)
(4) basic: Lys (K), Arg (R), His (H)

Alternatively, naturally occurring residues may be divided into groups based on common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

Any cysteine residue not involved in maintaining the proper conformation of the antibody also may be substituted, generally with serine, to improve the oxidative stability of the molecule and prevent aberrant crosslinking. Conversely, cysteine bond(s) may be added to the polypeptide to improve its stability (particularly where the antibody is an antibody fragment such as an Fv fragment).

A particularly preferred type of substitutional variant involves substituting one or more hypervariable region residues of a parent antibody (e.g., a humanized antibody). Generally, the resulting variant(s) selected for further development will have improved biological properties relative to the parent antibody from which they are generated. A convenient way for generating such substitutional variants involves affinity maturation using phage display. Briefly, several hypervariable region sites (e.g., 6-7 sites) are mutated to generate all possible amino substitutions at each site. The antibody variants thus generated are displayed in a monovalent fashion from filamentous phage particles as fusions to the gene III product of M13 packaged within each particle. The phage-displayed variants are then screened for their biological activity (e.g., binding affinity) as herein disclosed. In order to identify candidate hypervariable region sites for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the antibody and target. Such contact residues and neighboring residues are candidates for substitution according to the techniques elaborated herein. Once such variants are generated, the panel of variants is subjected to screening as described herein and antibodies with superior properties in one or more relevant assays may be selected for further development.

Another type of amino acid variant of the polypeptide alters the original glycosylation pattern of the antibody. The polypeptide may comprise non-amino acid moieties. For example, the polypeptide may be glycosylated. Such glycosylation may occur naturally during expression of the polypeptide in the host cell or host organism, or may be a deliberate modification arising from human intervention. By altering is meant deleting one or more carbohydrate moieties found in the polypeptide, and/or adding one or more glycosylation sites that are not present in the polypeptide.

Glycosylation of polypeptide is typically either N-linked or O-linked. N-linked refers to the attachment of the carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition of glycosylation sites to the polypeptide is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

Removal of carbohydrate moieties present on the polypeptide may be accomplished chemically or enzymatically or by mutational substitution of codons encoding for amino acid residues that serve as targets for glycosylation. Enzymatic cleavage of carbohydrate moieties on polypeptides can be achieved by the use of a variety of endo- and exo-glycosidases.

Other modifications include deamidation of glutaminyl and asparaginyl residues to the corresponding glutamyl and aspartyl residues, respectively, hydroxylation of proline and lysine, phosphorylation of hydroxyl groups of seryl or threonyl residues, methylation of the α-amino groups of lysine, arginine, and histidine side chains, acetylation of the N-terminal amine, and amidation of any C-terminal carboxyl group.

(ii) Chimeric Polypeptides

The polypeptide described herein may be modified in a way to form chimeric molecules comprising the polypeptide fused to another, heterologous polypeptide or amino acid sequence. In some embodiments, a chimeric molecule comprises a fusion of the polypeptide with a tag polypeptide which provides an epitope to which an anti-tag antibody can selectively bind. The epitope tag is generally placed at the amino- or carboxyl-terminus of the polypeptide. The presence of such epitope-tagged forms of the polypeptide can be detected using an antibody against the tag polypeptide. Also, provision of the epitope tag enables the polypeptide to be readily purified by affinity purification using an anti-tag antibody or another type of affinity matrix that binds to the epitope tag.

In an alternative embodiment, the chimeric molecule may comprise a fusion of the polypeptide with an immunoglobulin or a particular region of an immunoglobulin. A bivalent form of the chimeric molecule is referred to as an "immunoadhesin."

As used herein, the term "immunoadhesin" designates antibody-like molecules which combine the binding specificity of a heterologous polypeptide with the effector functions of immunoglobulin constant domains. Structurally, the immunoadhesins comprise a fusion of an amino acid sequence with the desired binding specificity which is other than the antigen recognition and binding site of an antibody (i.e., is "heterologous"), and an immunoglobulin constant domain sequence. The adhesin part of an immunoadhesin molecule typically is a contiguous amino acid sequence comprising at least the binding site of a receptor or a ligand. The immunoglobulin constant domain sequence in the immunoadhesin may be obtained from any immunoglobulin, such as IgG-1, IgG-2, IgG-3, or IgG-4 subtypes, IgA (including IgA-1 and IgA-2), IgE, IgD or IgM.

The Ig fusions preferably include the substitution of a soluble (transmembrane domain deleted or inactivated) form of a polypeptide in place of at least one variable region within an Ig molecule. In a particularly preferred embodiment, the immunoglobulin fusion includes the hinge, $CH_2$ and $CH_3$, or the hinge, $CH_1$, $CH_2$ and $CH_3$ regions of an IgG1 molecule.

(iii) Polypeptide Conjugates

The polypeptide for use in polypeptide formulations may be conjugated to a cytotoxic agent such as a chemotherapeutic agent, a growth inhibitory agent, a toxin (e.g., an enzymatically active toxin of bacterial, fungal, plant, or animal origin, or fragments thereof), or a radioactive isotope (i.e., a radioconjugate).

Chemotherapeutic agents useful in the generation of such conjugates can be used. In addition, enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, Phytolaca americana proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated polypeptides. Examples include $^{212}Bi$, $^{131}I$, $^{131}In$, $^{90}Y$, and $^{186}Re$. Conjugates of the polypeptide and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., *Science* 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the polypeptide.

Conjugates of a polypeptide and one or more small molecule toxins, such as a calicheamicin, maytansinoids, a trichothene, and CC1065, and the derivatives of these toxins that have toxin activity, are also contemplated herein.

Maytansinoids are mitototic inhibitors which act by inhibiting tubulin polymerization. Maytansine was first isolated from the east African shrub *Maytenus serrata*. Subsequently, it was discovered that certain microbes also produce maytansinoids, such as maytansinol and C-3 maytansinol esters. Synthetic maytansinol and derivatives and analogues thereof are also contemplated. There are many linking groups known in the art for making polypeptide-maytansinoid conjugates, including, for example, those disclosed in U.S. Pat. No. 5,208,020. The linking groups include disulfide groups, thioether groups, acid labile groups, photolabile groups, peptidase labile groups, or esterase labile groups, as disclosed in the above-identified patents, disulfide and thioether groups being preferred.

The linker may be attached to the maytansinoid molecule at various positions, depending on the type of the link. For example, an ester linkage may be formed by reaction with a hydroxyl group using conventional coupling techniques. The reaction may occur at the C-3 position having a hydroxyl group, the C-14 position modified with hydroxymethyl, the C-15 position modified with a hydroxyl group, and the C-20 position having a hydroxyl group. In a preferred embodiment, the linkage is formed at the C-3 position of maytansinol or a maytansinol analogue.

Another conjugate of interest comprises a polypeptide conjugated to one or more calicheamicin molecules. The calicheamicin family of antibiotics are capable of producing double-stranded DNA breaks at sub-picomolar concentrations. For the preparation of conjugates of the calicheamicin family, see, e.g., U.S. Pat. No. 5,712,374. Structural analogues of calicheamicin which may be used include, but are not limited to, $\gamma_1^I$, $\alpha_2^I$, $\alpha_3^I$, N-acetyl-$\gamma_1^I$, PSAG and $\theta_1^I$. Another anti-tumor drug that the antibody can be conjugated is QFA which is an antifolate. Both calicheamicin and QFA have intracellular sites of action and do not readily cross the plasma membrane. Therefore, cellular uptake of these agents through polypeptide (e.g., antibody) mediated internalization greatly enhances their cytotoxic effects.

Other antitumor agents that can be conjugated to the polypeptides described herein include BCNU, streptozoicin, vincristine and 5-fluorouracil, the family of agents known collectively LL-E33288 complex, as well as esperamicins.

In some embodiments, the polypeptide may be a conjugate between a polypeptide and a compound with nucleolytic activity (e.g., a ribonuclease or a DNA endonuclease such as a deoxyribonuclease; DNase).

In yet another embodiment, the polypeptide (e.g., antibody) may be conjugated to a "receptor" (such streptavidin) for utilization in tumor pre-targeting wherein the polypeptide receptor conjugate is administered to the patient, followed by removal of unbound conjugate from the circulation using a clearing agent and then administration of a "ligand" (e.g., avidin) which is conjugated to a cytotoxic agent (e.g., a radionucleotide).

In some embodiments, the polypeptide may be conjugated to a prodrug-activating enzyme which converts a prodrug (e.g., a peptidyl chemotherapeutic agent) to an active anti-cancer drug. The enzyme component of the immunoconjugate includes any enzyme capable of acting on a prodrug in such a way so as to convert it into its more active, cytotoxic form.

Enzymes that are useful include, but are not limited to, alkaline phosphatase useful for converting phosphate-containing prodrugs into free drugs; arylsulfatase useful for converting sulfate-containing prodrugs into free drugs; cytosine deaminase useful for converting non-toxic 5-fluorocytosine into the anti-cancer drug, 5-fluorouracil; proteases, such as *serratia* protease, thermolysin, subtilisin, carboxypeptidases and cathepsins (such as cathepsins B and L), that are useful for converting peptide-containing prodrugs into free drugs; D-alanylcarboxypeptidases, useful for converting prodrugs that contain D-amino acid substituents; carbohydrate-cleaving enzymes such as β-galactosidase and neuraminidase useful for converting glycosylated prodrugs into free drugs; β-lactamase useful for converting drugs derivatized with β-lactams into free drugs; and penicillin amidases, such as penicillin V amidase or penicillin G amidase, useful for converting drugs derivatized at their amine nitrogens with phenoxyacetyl or phenylacetyl groups, respectively, into free drugs. Alternatively, antibodies with enzymatic activity, also known in the art as "abzymes", can be used to convert the prodrugs into free active drugs.

(iv) Other

Another type of covalent modification of the polypeptide comprises linking the polypeptide to one of a variety of nonproteinaceous polymers, e.g., polyethylene glycol, polypropylene glycol, polyoxyalkylenes, or copolymers of polyethylene glycol and polypropylene glycol. The polypeptide also may be entrapped in microcapsules prepared, for example, by coacervation techniques or by interfacial polymerization (for example, hydroxymethylcellulose or gelatin-microcapsules and poly-(methylmethacylate) microcapsules, respectively), in colloidal drug delivery systems (for example, liposomes, albumin microspheres, microemulsions, nano-particles and nanocapsules), or in macroemulsions. Such techniques are disclosed in Remington's Pharmaceutical *Sciences*, 18th edition, Gennaro, A. R., Ed., (1990).

IV. Obtaining Polypeptides for Use in the Formulations and Methods

The polypeptides used in the methods of analysis described herein may be obtained using methods well-known in the art, including the recombination methods. The following sections provide guidance regarding these methods.

(A) Polynucleotides

"Polynucleotide," or "nucleic acid," as used interchangeably herein, refer to polymers of nucleotides of any length, and include DNA and RNA.

Polynucleotides encoding polypeptides may be obtained from any source including, but not limited to, a cDNA library prepared from tissue believed to possess the polypeptide mRNA and to express it at a detectable level. Accordingly, polynucleotides encoding polypeptide can be conveniently obtained from a cDNA library prepared from human tissue. The polypeptide-encoding gene may also be obtained from a genomic library or by known synthetic procedures (e.g., automated nucleic acid synthesis).

For example, the polynucleotide may encode an entire immunoglobulin molecule chain, such as a light chain or a heavy chain. A complete heavy chain includes not only a heavy chain variable region ($V_H$) but also a heavy chain constant region ($C_H$), which typically will comprise three constant domains: $C_H1$, $C_H2$ and $C_H3$; and a "hinge" region. In some situations, the presence of a constant region is desirable.

Other polypeptides which may be encoded by the polynucleotide include antigen-binding antibody fragments such as single domain antibodies ("dAbs"), Fv, scFv, Fab' and F(ab')$_2$ and "minibodies." Minibodies are (typically) bivalent antibody fragments from which the $C_H1$ and $C_K$ or $C_L$ domain has been excised. As minibodies are smaller than conventional antibodies they should achieve better tissue penetration in clinical/diagnostic use, but being bivalent they should retain higher binding affinity than monovalent antibody fragments, such as dAbs. Accordingly, unless the context dictates otherwise, the term "antibody" as used herein encompasses not only whole antibody molecules but also antigen-binding antibody fragments of the type discussed above. Preferably each framework region present in the encoded polypeptide will comprise at least one amino acid substitution relative to the corresponding human acceptor framework. Thus, for example, the framework regions may comprise, in total, three, four, five, six, seven, eight, nine, ten, eleven, twelve, thirteen, fourteen, or fifteen amino acid substitutions relative to the acceptor framework regions.

VI. Exemplary Embodiments

1. In one embodiment, the invention provides a method for analyzing a composition comprising a polypeptide and one or more contaminants, the method comprising a) binding the polypeptide and one of more contaminants to an ion-exchange chromatography material using a loading buffer, wherein the loading buffer is at a first pH and comprises a first ionic strength; b) eluting the polypeptide and one or more contaminants from the ion-exchange chromatography material using an elution buffer wherein the pH of the elution buffer is altered in a pH gradient and the ionic strength of the elution buffer is altered in an ionic strength gradient, wherein the polypeptide and the one or more contaminants are separated by the combination of pH gradient and ionic strength gradient; c) detecting the polypeptide and the one or more contaminants. In some aspects of this embodiment, the invention provides methods for analyzing polypeptides in compositions comprising a polypeptide and one or more contaminants, wherein the method separates one or more contaminants from the polypeptide, the method comprising a) binding the polypeptide and one of more contaminants to an ion-exchange chromatography material using a loading buffer, wherein the loading buffer is at a first pH and comprises a first ionic strength; b) eluting the polypeptide and one or more contaminants from the ion-exchange chromatography material using an elution buffer wherein the pH of the elution buffer is altered in a pH gradient and the ionic strength of the elution buffer is altered in a ionic strength gradient, wherein the polypeptide and the one or more contaminants are separated by the combination of pH gradient and ionic strength gradient; c) detecting the polypeptide and the one or more contaminants, wherein the method is used to analyze polypeptides having a pI ranging from about 7.0 to about 9.5.

2. In a further embodiment of embodiment 1, the polypeptide is an antibody or immunoadhesin or fragment thereof.

3. In a further embodiment of embodiments 1 or 2, the polypeptide is a monoclonal antibody or fragment thereof.

4. In a further embodiment of embodiments 2 or 3, the antibody is a human antibody.

5. In a further embodiment of embodiments 2 or 3, the antibody is a humanized antibody.

6. In a further embodiment of embodiments 2 or 3, the antibody is a chimeric antibody.

7. In a further embodiment of any one of embodiments 2-6 the antibody is an antibody fragment.

8. In a further embodiment of any one of embodiments 1-7 the contaminant is a variant of the polypeptide.

9. In a further embodiment of any one of embodiments 1-7, the contaminant is a degradation product of the polypeptide. For example, a charge variant.

10. In a further embodiment of any one of embodiments 1-9 the polypeptide has a pI greater than about 9.0.

11. In a further embodiment of any one of embodiments 1-10, the chromatography material is a cation exchange chromatography material.

12. In a further embodiment of embodiment 11, the cation exchange chromatography material is a sulfonated chromatography material or a carboxylated chromatography material.

13. In a further embodiment of any one of embodiments 1-12, the pH gradient is a linear gradient.

14. In a further embodiment of any one of embodiments 1-12, the pH gradient is a step gradient.

15. In a further embodiment of embodiments 13 or 14, the pH gradient comprises an increase from about pH 5 to about pH 11.

16. In a further embodiment of any one of embodiments 1-15, the pH gradient is generated using one or more buffers.

17. In a further embodiment of embodiment 15, the one or more buffers selected from piperazine, imidazole, tris, phosphate, or CAPS.

18. In a further embodiment of any one of embodiments 1-17, the ionic strength gradient is a linear gradient.

19. In a further embodiment of any one of embodiments 1-17, the ionic strength gradient is a step gradient.

20. In a further embodiment of embodiments 18 or 19, the ionic strength gradient comprises an increase in salt concentration from about 0 mM to about 200 mM.

21. In a further embodiment of any one of embodiments 18-20, the ionic strength gradient is an NaCl gradient, a KCl gradient, or an $Na_2SO_4$ gradient.

22. In a further embodiment of any one of embodiments 1-9, the polypeptide has a pI less than about 7.0.

23. In a further embodiment of embodiment 22, the chromatography material is an anion exchange chromatography material.

24. In a further embodiment of embodiment 23, the anion exchange chromatography material is a quarternary amine chromatography material or a tertiary amine chromatography material.

25. In a further embodiment of any one of embodiments 22-24, the pH gradient is a linear gradient.

26. In a further embodiment of any one of embodiments 22-24, the pH gradient is a step gradient.

27. In a further embodiment of embodiments 25 or 26, the pH gradient comprises a decrease from about pH 8 to about pH 5.

28. In a further embodiment of any one of embodiments 22-27, the pH gradient is generated using one or more buffers.

29. In a further embodiment of embodiment 28, the one or more buffers selected from piperazine, imidazole or Tris.

30. In a further embodiment of any one of embodiments 22-29, the ionic strength gradient is a linear gradient.

31. In a further embodiment of any one of embodiments 22-29, the ionic strength gradient is a step gradient.

32. In a further embodiment of embodiment 30 or 31, the ionic strength gradient comprises an increase in salt concentration from about 0 mM to about 200 mM.

33. In a further embodiment of any one of embodiments 30-32, the ionic strength gradient is a NaCl gradient, a KCl gradient, or an $Na_2SO_4$ gradient.

34. In one embodiment, the invention provides a method for analyzing a composition comprising the polypeptide and one or more contaminants, the method comprising a) binding the polypeptide and one of more contaminants to an ion-exchange chromatography material using a loading buffer, wherein the loading buffer is at an initial pH and comprises an initial ionic strength; b) eluting the polypeptide and one or more contaminants from the ion-exchange chromatography material using an elution buffer wherein the pH of the elution buffer is altered in a pH gradient and wherein the ionic strength of the elution buffer is essentially the same as the initial ionic strength of the loading buffer, wherein the polypeptide and the one or more contaminants are separated by pH gradient at about the initial ionic strength; c) detecting the polypeptide and the one or more contaminants. In some aspects of this embodiment, the invention provides method for analyzing polypeptides in compositions comprising a polypeptide and one or more contaminants, the method comprising a) binding the polypeptide and one of more contaminants to an ion-exchange chromatography material using a loading buffer, wherein the loading buffer is at an initial pH and comprises an initial ionic strength; b) eluting the polypeptide and one or more contaminants from the ion-exchange chromatography material using an elution buffer wherein the pH of the elution buffer is altered in a pH gradient and wherein the ionic strength of the elution buffer is essentially the same as the initial ionic strength of the loading buffer, wherein the polypeptide and the one or more contaminants are separated by pH gradient at about the initial ionic strength; c) detecting the polypeptide and the one or more contaminants, wherein the method is used to analyze polypeptides having a pI ranging from about 7.0 to about 9.5.

35. In a further embodiment of embodiment 34, the polypeptide is an antibody or immunoadhesin or fragment thereof.

36. In a further embodiment of embodiments 34 or 35, the polypeptide is a monoclonal antibody or fragment thereof.

37. In a further embodiment of embodiments 35 or 36, the antibody is a human antibody.

38. In a further embodiment of embodiment 35 or 36, the antibody is a humanized antibody.

39. In a further embodiment of embodiments 35 or 36, the antibody is a chimeric antibody.

40. In a further embodiment of any one of embodiments 35-39, the antibody is an antibody fragment.

41. In a further embodiment of any one of embodiments 34-40, the contaminant is a variant of the polypeptide.

42. In a further embodiment of any one of embodiments 34-40, the contaminant is a degradation product of the polypeptide.

43. In a further embodiment of any one of embodiments 34-42, the polypeptide has a pI greater than about 9.0.

44. In a further embodiment of any one of embodiments 34-43, the chromatography material is a cation exchange chromatography material.

45. In a further embodiment of embodiment 44, the cation exchange chromatography material is a sulfonated chromatography material or a carboxylated chromatography material.

46. In a further embodiment of any one of embodiments 34-45, the pH gradient is a linear gradient.

47. In a further embodiment of any one of embodiments 34-45, the pH gradient is a step gradient.

48. In a further embodiment of embodiment 46 or 47, the pH gradient comprises an increase from about pH 5 to about pH 11.

49. In a further embodiment of any one of embodiments 34-48, the pH gradient is generated using one or more buffers.

50. In a further embodiment of embodiment 49, the one or more buffers selected from piperazine, imidazole, tris, phosphate, or CAPS.

51. In a further embodiment of any one of embodiments 34-50, the ionic strength of the elution buffer is from about 0 mM to about 100 mM.

52. In a further embodiment of embodiment 51, the elution buffer comprise about 0 mM NaCl to about 100 mM NaCl, about 0 mM KCl to about 100 mM KCl, or about 0 mM $Na_2SO_4$ to about 100 mM $Na_2SO_4$.

53. In a further embodiment of any one of embodiments 34-42, the polypeptide has a pI less than about 7.0.

54. In a further embodiment of embodiment 53, the chromatography material is an anion exchange chromatography material.

55. In a further embodiment of embodiment 54, the anion exchange chromatography material is a quarternary amine chromatography material or a tertiary amine chromatography material.

56. In a further embodiment of any one of embodiments 53-55, the pH gradient is a linear gradient.

57. In a further embodiment of any one of embodiments 53-55, the pH gradient is a step gradient.

58. In a further embodiment of embodiments 56 or 57, the pH gradient comprises a decrease from about pH 8 to about pH 5.

59. In a further embodiment of any one of embodiments 53-58, the pH gradient is generated using one or more buffers.

60. In a further embodiment of embodiment 59, the one or more buffers selected from piperazine, imidazole or Tris.

61. In a further embodiment of any one of embodiments 53-60, the ionic strength of the elution buffer is from about 0 mM to about 100 mM.

62. In a further embodiment of embodiment 61, the elution buffer comprise about 10 mM NaCl to about 100 mM NaCl.

63. In a further embodiment of any one of embodiments 1-62, the analysis is by high performance liquid chromatography.

64. In a further embodiment of any one of embodiments 1-63, the concentration of the buffer in the loading buffer and/or the elution buffer varies from 10 mM to about 50 mM.

65. In a further embodiment of any one of embodiments 1-64, the first pH varies from about pH 5.0 to about pH 7.0.

66. In a further embodiment of any one of embodiments 1-65, the temperature of the chromatography material varies from about 20° C. to about 50° C.

67. In a further embodiment of any one of embodiments 1-66, the loading and elution are conducted at a flow rate varying from about 0.5 ml/min to about 2.0 ml/min.

68. In another embodiment, the invention provides a method of determining the purity of a polypeptide in a composition comprising analyzing the composition according to any one of the methods of embodiments 1 to 67 and determining the ratio of polypeptide to contaminants in the composition.

69. In another embodiment, the invention provides a method of determining the stability of a polypeptide in a composition comprising the polypeptide, the method comprising,
   a) incubating the composition comprising the polypeptide at 0° C. to 40° C. for one to six weeks,
   b) analyzing the composition of step a) by any of the methods of embodiments 1 to 67, and c) determining the ratio of variants to polypeptide in the composition, wherein an increase in the ratio of variants to polypeptide in the composition compared to a composition that was not incubated indicates the degradation of the polypeptide in the composition.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

Further details of the invention are illustrated by the following non-limiting Examples. The disclosures of all references in the specification are expressly incorporated herein by reference.

EXAMPLES

The examples below are intended to be purely exemplary of the invention and should therefore not be considered to limit the invention in any way. The following examples and detailed description are offered by way of illustration and not by way of limitation.

Materials and Methods for Examples

The following materials and methods were used for the examples unless otherwise noted.

Materials

All mAbs were manufactured in-house at Genentech (South San Francisco, Calif.) using stable Chinese Hamster Ovary (CHO) cell lines. The pI values for the mAbs used were determined experimentally using an icIEF protocol from the instrument manufacturer (Wu, J and Huang, T (2006) *Electrophoresis* 27:3584) employing seven pI markers. Thermal stressed samples were obtained by incubating mAbs at 40° C. for 3 and 6 weeks, respectively. The stressed mAbs were stored at −80° C. before chromatographic analysis.

Propac WCX-10 columns were purchased from Dionex. Imidazole was obtained from EMD Biosciences or from Fluka. Piperazine (anhydrous) was acquired from Tokyo Chemical Industry Co. LTD. Trisma (Tris) were obtained from Mallinckrodt Baker Inc. or Sigma (St. Louis, Mo.)., Trizma base and CAPS was obtained from Sigma. Sodium chloride, sodium hydroxide (10 N) and hydrochloric acid (12 N) were obtained from Mallinckrodt Baker Inc. Phosphoric acid (85%) was obtained from EMD Millipore.

HPLC Set up

Cation-exchange chromatography experiments were primarily performed on a Waters 2796 BioAlliance liquid chromatography instrument or an UltiMate 3000 Quaternary Rapid Separation LC (Thermo Scientific Dionex). The instrument included a low-pressure quaternary gradient pump, an auto-sampler with temperature control capability, a thermal column compartment for precise temperature control, and a dual-wavelength diode array UV detector. At the outlet of the column, an in-line pH sensor (Model S450CD from Sensorex) and a conductivity sensor (Model 529 from Amber Science, Eugene, Oreg.) were connected in tandem. The pH sensor was controlled by a model Seven Multi pH meter from Mettler Toledo; the conductivity sensor was controlled by a model 1056 digital conductivity meter from Amber Science. The pH and conductivity readings from the two meters were collected into Chromeleon through a Dionex UCI 50 analog/digital convertor. Instrument control, data acquisition, and data analysis were performed with Dionex Chromeleon software, version 6.8.

Mobile Phase Preparation

Individual stock buffer solutions of tris and imidazole were prepared at 1.0 M and a solution of CAPS was prepared at a concentration of 0.1 M, without adjusting the pH value and stored at room temperature. A stock buffer solution containing 40 mM of piperazine, 40 mM imidazole, and 40 mM Tris (all free bases) was first prepared without adjusting the pH value and stored at room temperature. Prior to chromatographic experiments, a series of the mobile phase buffers containing equimolar concentration of piperazine, imidazole and Tris at 1, 2, 4 or 8 mM, were each made by diluting the buffer stock solution with deionized water. The pH values of the buffers were then adjusted using hydrochloric acid to 5.0 (Buffer A) and 10.8 (Buffer B), respectively. Sodium chloride solution of 0.5 M was prepared with deionized water (Salt Solution). The mobile phases were then individually filtered through a 0.2 µM nylon filter prior to use.

The mobile phase buffers with 11.6 mM piperazine, 1.5 mM imidazole and 2.4 mM Tris were prepared as reported in literature (Farnan, D and Moreno, G T (2009) *Anal. Chem.* 81:8846; Rea, J C et al. (2010) *J. Pharm. Biomed. Anal.* 54:317). A ten-fold concentrated stock solution containing 116 mM piperazine, 15 mM imidazole and 24 mM Tris was first prepared and stored at room temperature. Before each experiment, two aliquots of the stock solution were diluted 10-fold with deionized water and their pH values were subsequently adjusted using hydrochloric acid to 5.0 (Buffer C) and 9.5 (Buffer D). The mobile phases were then individually filtered through a 0.2 µM nylon filter prior to use.

Cation-Exchange Chromatography

Unless stated otherwise, the chromatographic conditions were as follows. mAb samples (control and stressed) were diluted to 2 mg/mL with deionized water and were kept at 5±3° C. in the auto-sampler. Alternatively, mAb samples were diluted to 1 mg/mL with a 1:1 mixture of buffers A and D and were kept at 5±3° C. in the auto-sampler. The Propac WCX-10HT, 4×50 mm column was placed in the column compartment with the temperature setting at 40±1° C. A 4×250 mm Dionex Propac WCX column was used for chromatographic separation and placed in the column compartment with the temperature setting at 40±1° C. For each chromatographic run, 10 µL of protein (20 µg) was injected.

The salt-mediated pH gradient was established by using a ternary gradient formed on the quaternary pump using buffer A, B and the Salt Solution (0.5 M NaCl). A linear gradient from 100% A to 96.8% B and 3.2% salt solution in 58 minutes was delivered to establish a pH gradient from 5.0 to 10.8 (0.1 pH unit/min) and a mediating salt gradient from 0 to 16 mM NaCl (0.28 mM/min). The final gradient (min, % B and C) was as follows: 0, 100% A; 2, 100% A; 60, 96.8% B and 3.2% C; 64, 96.8% B and 3.2% C; 65, 100% A; 75, 100% A. The mobile phase flow rate was 1.0 mL/min.

The reported pH gradient from 5.0 to 9.5 (Farnan, D and Moreno, G T (2009) *Anal. Chem.* 81:8846) was established by buffer C and D. A linear increase of buffer D from 0 to 100% in 45 minutes was delivered to establish a pH gradient from 5.0 to 9.5 (0.1 pH unit/min). The mobile phase flow rate was 1.0 mL/min. Proteins were detected by ultraviolet (UV) absorbance at 280 nm.

A hybrid pH gradient was established by using a quaternary gradient formed on the quaternary pump using buffers A, B, C and D. This arrangement offered the flexibility of adjusting 1) the starting and ending pH, using buffers A and B and 2) the amount of salt for each gradient, using buffers C and D. An example of the methods used in these experiments, a pH gradient from 6 to 10, with a constant salt concentration of 10 mM, was established by an increase of buffer B from 0 to 40%, while maintaining buffers C and D at 10% and 40%, respectively. The gradients used are listed in the Table 2.

Modeling of the pH-IEC

The pH of the linearly mixing gradient of two pH buffers was estimated using the Henderson-Hasselbalch (H-H) equation for each of the components based on ideal solution model. The number of available/dissociable protons was first determined for each starting buffer and subsequently for each pH value between the two buffers at a step of 0.1 pH unit. Based on the required number of protons, the molar ratio of the two buffers was derived. The percent of each buffer to attain a pH point in the gradient was obtained. At each pH point, ionic strength was calculated using the estimated ionic components.

Example 1

Assessment of a pH-IEC Method

The performance of a pH-IEC method was assessed. Although the reported pH-IEC method shows the capability of profiling the charge heterogeneity of multiple mAbs, it is intended primarily for mAbs with pI values from about 7 to 9. For mAbs beyond this range (pI<7 or pI>9, also referred to as extreme pI values), the pH-IEC method often yields unacceptable charge heterogeneity profiles. To assess the method, a pH gradient from 5.0 to 9.5 was produced following the procedure that was previously reported (Farnan, D and Moreno, G T (2009) *Anal. Chem.* 81:8846; Rea, J C et al. (2010) *J. Pharm. Biomed. Anal.* 54:317). The buffers were composed of 11.4 mM piperazine, 1.5 mM imidazole and 2.4 mM Tris and pH adjusted to 5.0 and 9.5, respectively. Three mAbs spanning a wide range of pI (6.2, 8.2 and 9.4) were analyzed and the resulting chromatograms are shown in FIG. 1. Of these mAbs, only mAb2 (pI 8.2) showed an acceptable charge heterogeneity profile characterized by a good separation of charge variants. The charge variants of the low pI mAb1 (pI=6.2) were not well separated; the high pI mAb3 (pI 9.4) did not elute during the pH gradient. Even though mAb3 was eluted when the pH gradient was extended to pH 10.8, the column back pressure was close to the upper pressure limit of the column and the chromatography profiles were inconsistent between different runs. This experiment clearly demonstrated that although the reported pH-IEC method worked well for mAbs with pI values between 7 and 9, it was not able to profile the charge heterogeneity of mAbs with the extreme pI values.

TABLE 2

Sample Gradients

For samples with pI values between 7.2-8.3

| pH 6-9, 10 mM NaCl; 22 min run | | | | | pH 6-9, 10 mM NaCl; 15 min run | | | | |
|---|---|---|---|---|---|---|---|---|---|
| Time, min | % B | % C | % D | curve | Time, min | % B | % C | % D | curve |
| 0.0 | 0.0 | 10 | 40 | 5 | 0.0 | 0.0 | 10 | 40 | 5 |
| 0.2 | 0.0 | 10 | 40 | 5 | 0.2 | 0.0 | 10 | 40 | 5 |
| 16.0 | 30.0 | 10 | 40 | 5 | 10.0 | 30.0 | 10 | 40 | 5 |
| 18.0 | 30.0 | 10 | 40 | 5 | 12.0 | 30.0 | 10 | 40 | 5 |
| 18.1 | 0.0 | 10 | 40 | 5 | 12.1 | 0.0 | 10 | 40 | 5 |
| 22.0 | 0.0 | 10 | 40 | 5 | 15.0 | 0.0 | 10 | 40 | 5 |

For samples with pI values between 8.3-9.0

| pH 6-10, 20 mM NaCl; 22 min run | | | | | pH 6-10, 20 mM NaCl; 15 min run | | | | |
|---|---|---|---|---|---|---|---|---|---|
| Time, min | % B | % C | % D | curve | Time, min | % B | % C | % D | curve |
| 0.0 | 0.0 | 20 | 30 | 5 | 0.0 | 0.0 | 20 | 30 | 5 |
| 0.2 | 0.0 | 20 | 30 | 5 | 0.2 | 0.0 | 20 | 30 | 5 |
| 16.0 | 40.0 | 20 | 30 | 5 | 10.0 | 40.0 | 20 | 30 | 5 |
| 18.0 | 40.0 | 20 | 30 | 5 | 12.0 | 40.0 | 20 | 30 | 5 |
| 18.1 | 0.0 | 20 | 30 | 5 | 12.1 | 0.0 | 20 | 30 | 5 |
| 22.0 | 0.0 | 20 | 30 | 5 | 15.0 | 0.0 | 20 | 30 | 5 |

TABLE 2-continued

Sample Gradients

For samples with pI values between 9.0-9.2

| pH 7-10, 50 mM NaCl; 22 min run | | | | | pH 7-10, 50 mM NaCl; 15 min run | | | | |
|---|---|---|---|---|---|---|---|---|---|
| Time, min | % B | % C | % D | curve | Time, min | % B | % C | % D | curve |
| 0.0 | 10.0 | 50 | 0 | 5 | 0.0 | 10.0 | 50 | 0 | 5 |
| 0.2 | 10.0 | 50 | 0 | 5 | 0.2 | 10.0 | 50 | 0 | 5 |
| 16.0 | 40.0 | 50 | 0 | 5 | 10.0 | 40.0 | 50 | 0 | 5 |
| 18.0 | 40.0 | 50 | 0 | 5 | 12.0 | 40.0 | 50 | 0 | 5 |
| 18.1 | 10.0 | 50 | 0 | 5 | 12.1 | 10.0 | 50 | 0 | 5 |
| 22.0 | 10.0 | 50 | 0 | 5 | 15.0 | 10.0 | 50 | 0 | 5 |

For samples with pI values between 9.3-9.4

| pH 9-11, 10 mM NaCl; 22 min run | | | | | pH 9-11, 10 mM NaCl; 15 min run | | | | |
|---|---|---|---|---|---|---|---|---|---|
| Time, min | % B | % C | % D | curve | Time, min | % B | % C | % D | curve |
| 0.0 | 30.0 | 10 | 40 | 5 | 0.0 | 30.0 | 10 | 40 | 5 |
| 0.2 | 30.0 | 10 | 40 | 5 | 0.2 | 30.0 | 10 | 40 | 5 |
| 16.0 | 50.0 | 10 | 40 | 5 | 10.0 | 50.0 | 10 | 40 | 5 |
| 18.0 | 50.0 | 10 | 40 | 5 | 12.0 | 50.0 | 10 | 40 | 5 |
| 18.1 | 30.0 | 10 | 40 | 5 | 12.1 | 30.0 | 10 | 40 | 5 |
| 22.0 | 30.0 | 10 | 40 | 5 | 15.0 | 30.0 | 10 | 40 | 5 | pH at the column exit increased from 5.0 to 9.5, the conductivity of the solvent decreased in a near-linear fashion from 2700 to 800 µS/m (note that the conductivity of 5 mM KCl is 720 µS/m while the conductivity of deionized water is 5.5 µS/m). The three pH buffer components are all amines with $pK_a$ over a broad range: piperazine with $pK_{a1}=5.68$ and $pK_{a2}=9.82$, imidazole with $pK_a=6.95$ and Tris with $pK_a=8.10$ (at room temperature). These compounds are protonated (or positively charged) when the solution pH is lower than its $pK_a$, but become neutral when the pH is above its $pK_a$. When the solvent pH increases, the buffer components gradually become neutral from protonated and thus the conductivity of the buffer decreases. It is noteworthy that the pH profile was concave at pH around 6 because the piperazine was the most abundant component in the buffer so that the pH curve was relatively flat around its two $pK_a$ of 5.68 and 9.82.

Figure 2A:
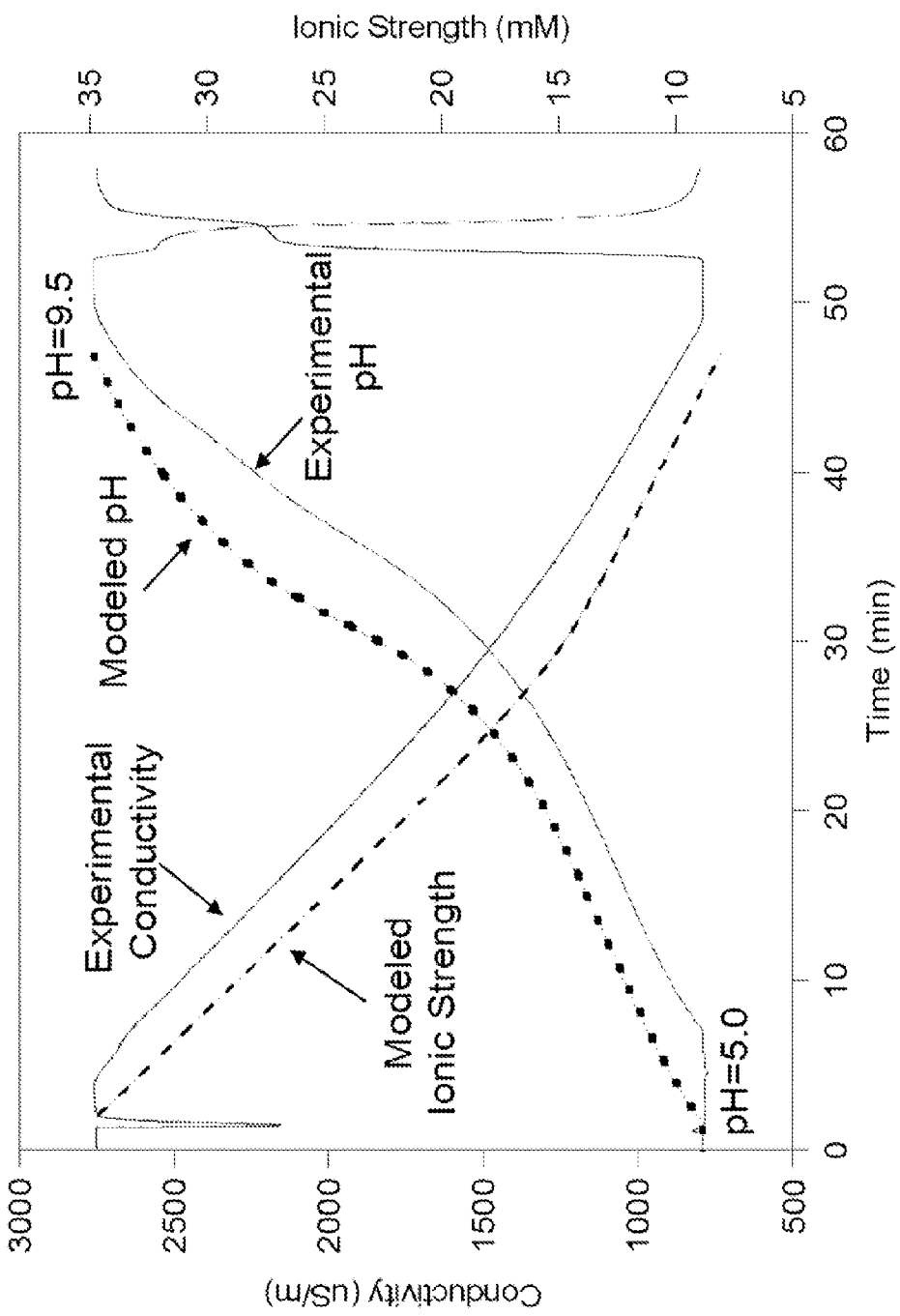
FIG. 2 shows the ionic strength and pH profiles at column exit (panel A) and the column back pressure in the pH gradient (panel B) before optimization and the ionic strength and pH profiles at column exit (panel C) and the column back pressure in the pH gradient (panel D) after optimization. Modeled and experimental pH profiles and conductivity profiles are shown in panels A and C.

The pH and ionic strength profiles of the pH gradient were also calculated based on an ideal solution model shown as dashed lines in FIG. 2A. The modeled pH curve is very similar to the experimental pH profile except for that the experimental profile was delayed by 5 minutes because of the system dwell volume and column volume. Likewise, the modeled ionic strength curve showed similar shape as the conductivity profile observed experimentally. The agreement between the modeling and experimental data suggests that the mixing of amine-based buffer components followed the ideal solution model. The established model can thus be used to estimate experimental pH and ionic strength profiles at other chromatography conditions.

Figure 2B:
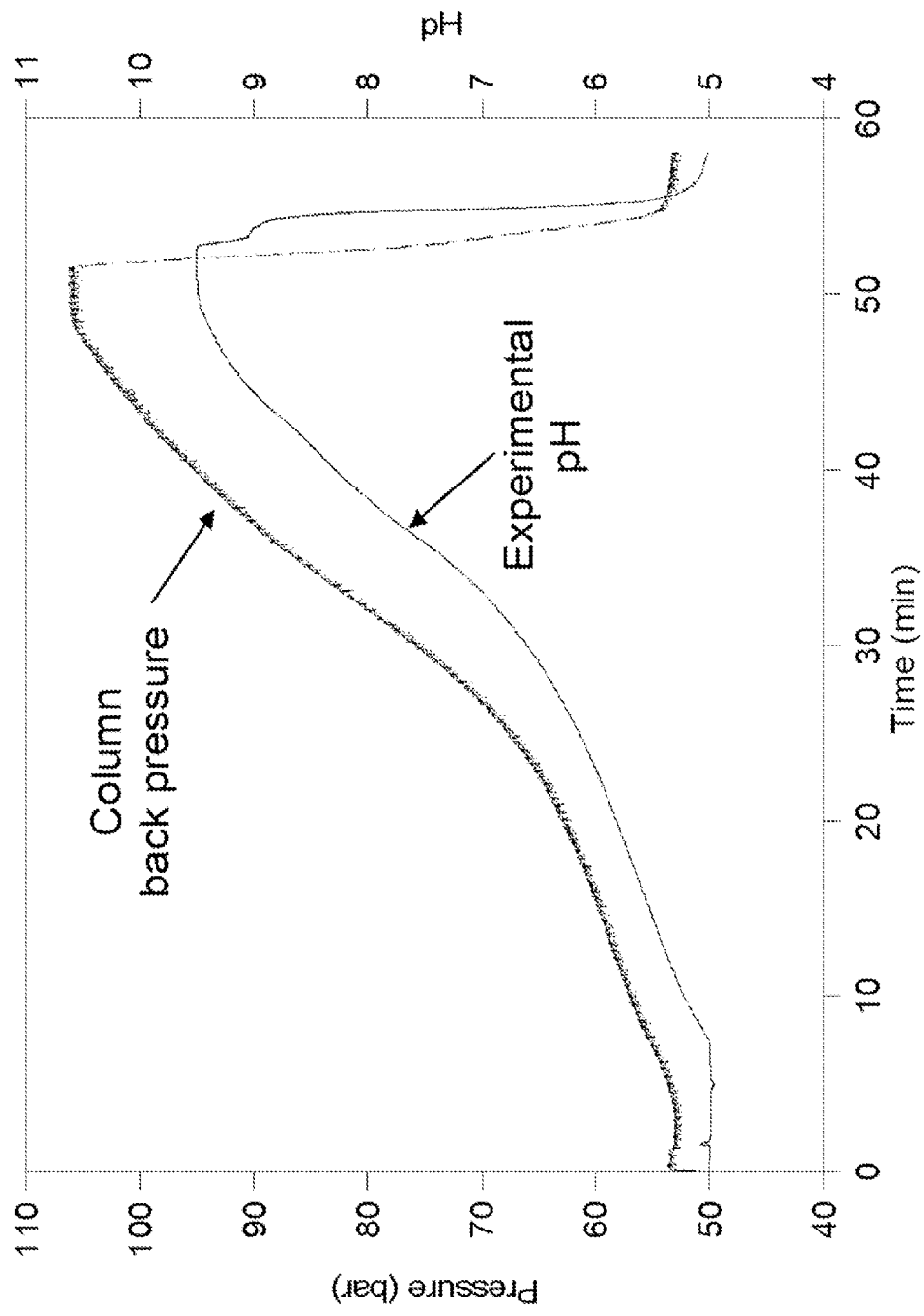
Figure 2:
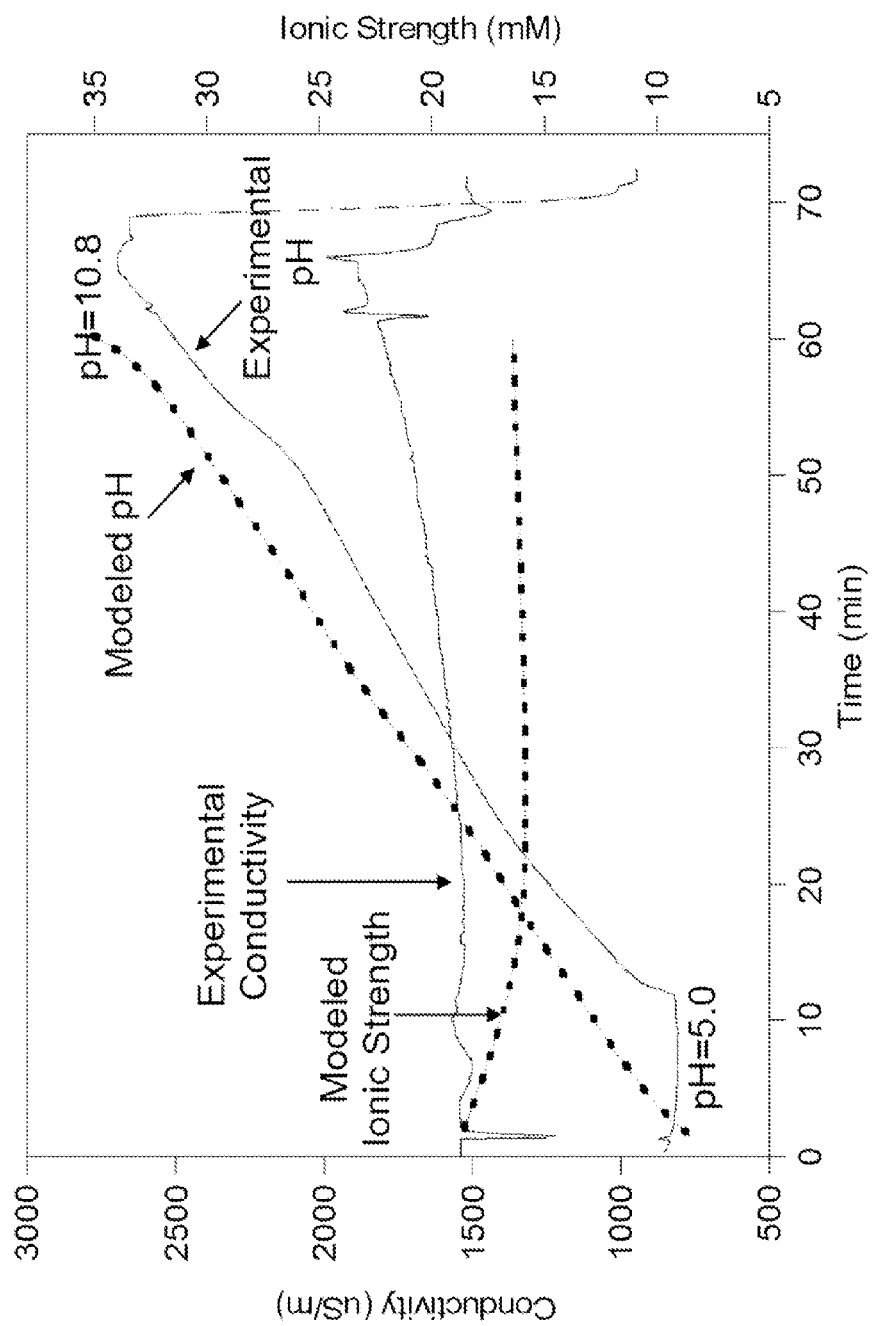
Figure 2:
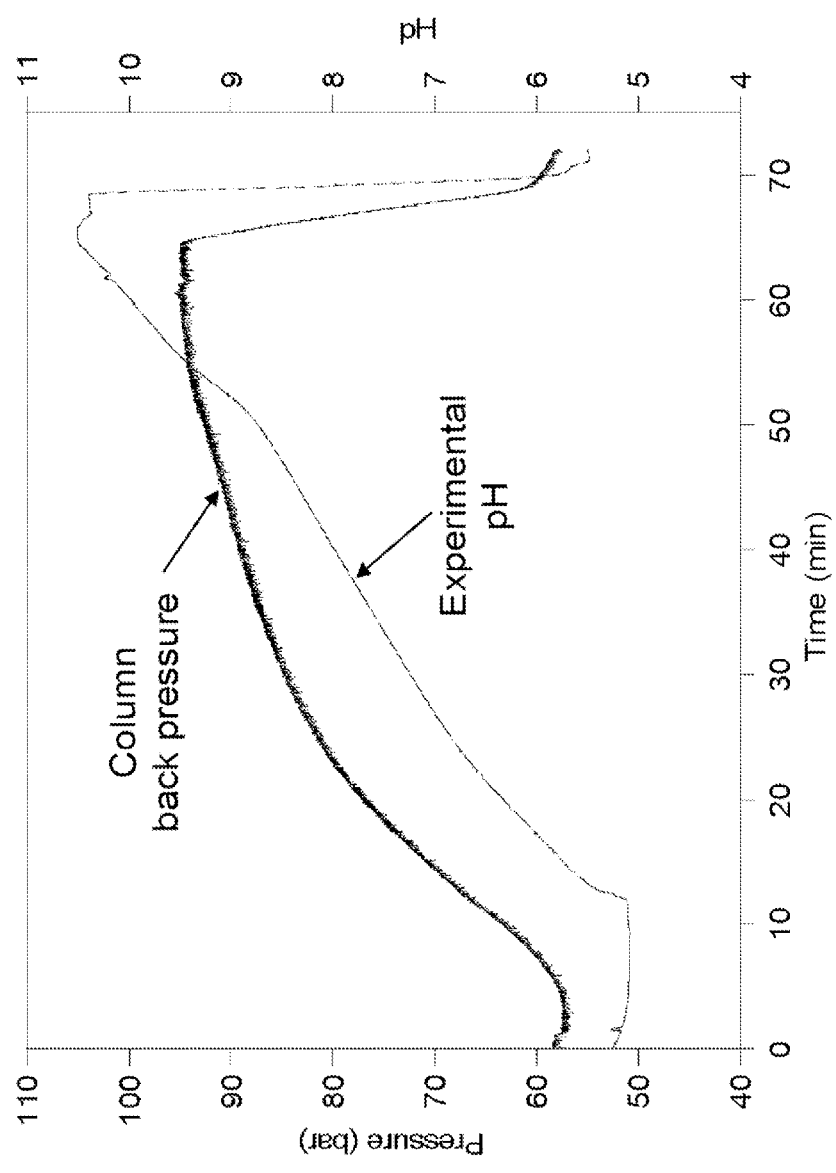

Furthermore, the column back pressure during pH-IEC significantly increased with the pH of mobile phase (FIG. 2B). This is attributed to the decrease of ionic strength, considering that the composition of mobile phase was constant during the pH gradient. When the ionic strength of mobile phase is low, the electrostatic potential on the stationary phase surface becomes high, according to the double layer model (Staahlberg, J (1994) *Anal. Chem.* 66:440; Stahlberg, J (1999) *J. Chromatogr.* A 855:3). The high electrostatic potential may change the conformation of the resin (e.g. swelling the resin to reduce the surface charge density), which likely increases the column back pressure (Product Manual for Propac WCX-10 and Propac SCX-10, 7th ed., Dionex Incorporation, Sunnyvale, Calif., 2007).

The experimental conductivity and the modeled ionic strength profiles can be used to explain the poor charge heterogeneity profiles for mAbs with extreme pI values. Low-pI mAbs elute in the low pH region where the buffer components are protonated and the mobile phase has a relatively high ionic strength. Since the pH gradient IEC separation appears to involve a combination of ionic strength-based and pH-based elution mechanisms (Anderson, D J and Shan, L (2001) *Clin. Chem.* 47:128; Shan, L and Anderson, D J (2001) *J. Chromatogr. A* 909:191; Shan, L and Anderson, D J (2002) *Anal. Chem.* 74:5641), the high ionic strength-based elution may convolute with the pH-based elution, leading to a poor resolution of these low-pI mAb charge variants. On the other hand, high-pI mAbs typically elute in the high pH region where the buffer components become neutral. Because of the low ionic strength in mobile phase, these high-pI mAb are difficult to elute from cation exchange columns. In order to confirm that the ionic strength significantly affects the pH-IEC separation and improve the pH-IEC method for mAbs with extreme pI values, the ionic strength of the pH buffer in the pH-gradient IEC method was modulated as described below.

Example 3

Improving the pH-Gradient IEC Method by Controlling Ionic Strength

The ionic strength during the course of a pH gradient was modulated in two ways. First, the ionic strength at the low pH region was controlled by using different concentrations of buffers. A series of buffer concentrations were tested to assess their impact on pH gradient IEC as discussed below. Second, the ionic strength at high pH region was modulated by adding a salt gradient to the pH gradient. The impact of the salt concentration was also investigated. The new method is thus referred to as an "ionic strength-mediated pH-IEC" method.

Buffer Concentration: In this method, an equimolar pH-gradient is used rather than a mixed ratio pH gradient used in the reported method (Farnan, D and Moreno, G T (2009) *Anal. Chem.* 81:8846) based on two considerations: First, a near-linear pH gradient can be obtained by using equimolar concentrations of piperazine, imidazole and Tris (FIG. 2C). The established linear gradient over a broad range of pH would not sacrifice the separation for a given pH region Tsonev, L I and Hirsh, A G (2008) *J. Chromatogr. A* 1200:166). Second, it provides for optimization of the gradient slope.

Figure 3:
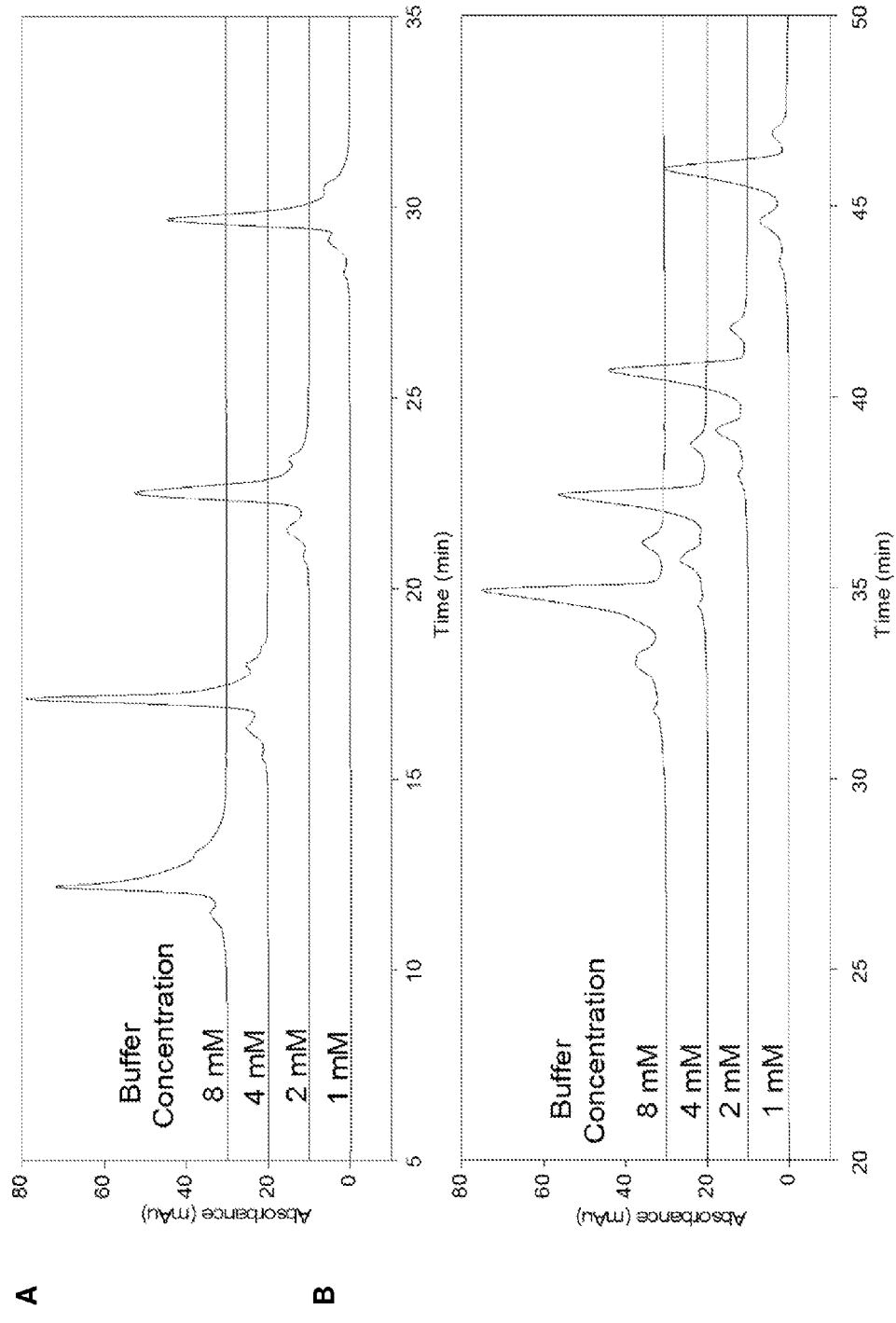
FIG. 3 shows the ionic strength mediated pH IEC chromatograms of mAb1 (panel A) and mAb2 (panel B) obtained with four different buffer concentrations. The full-width at half-maxima (FWHM) of the main peak in the chromatograms are plotted against buffer concentration (panel C) and salt concentration (panel D).
Figure 3:
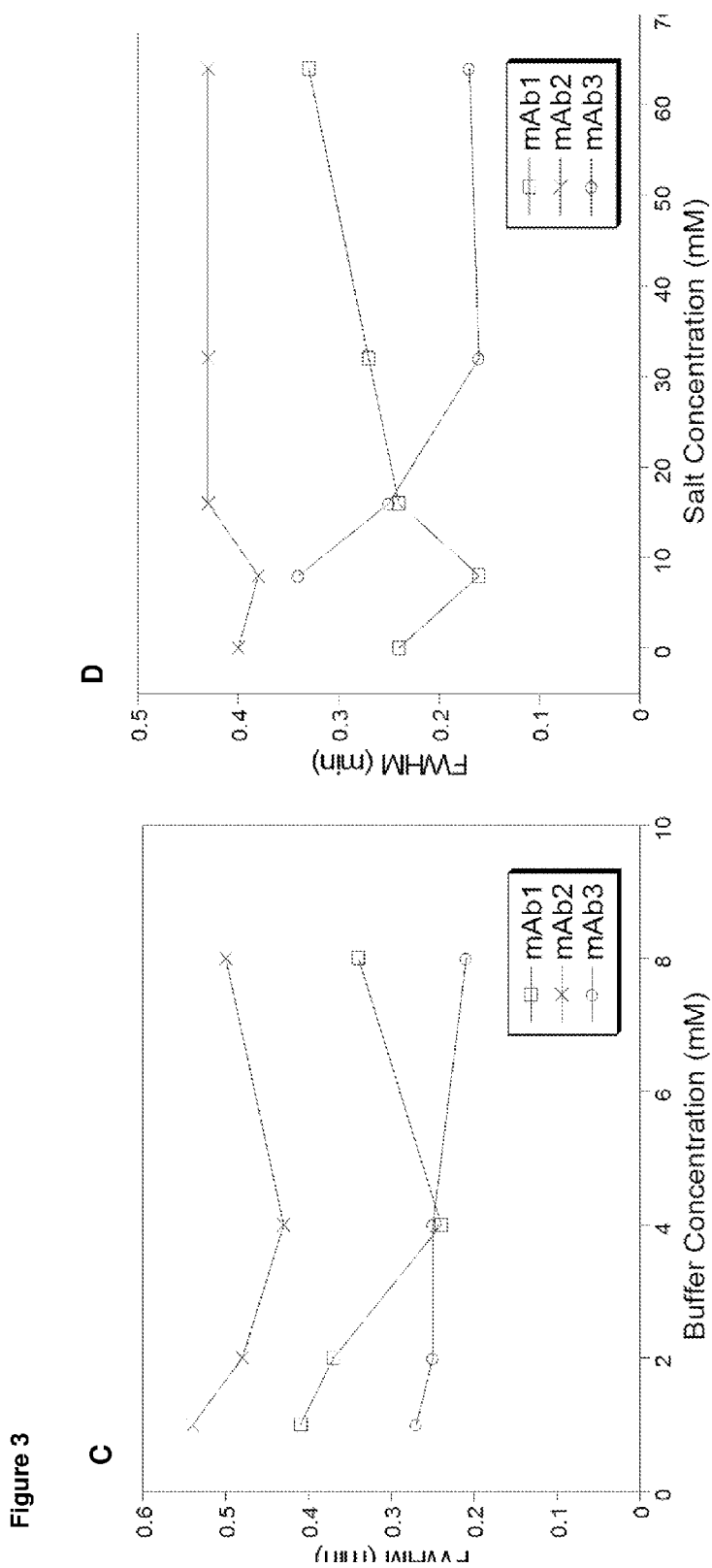

Four buffers consisting of equimolar concentrations of piperazine, imidazole and tris at 1, 2, 4 and 8 mM were investigated. These buffers were referred to as 1, 2, 4 and 8 mM buffers and each was mediated with a pH gradient from pH 5.0 to 10.8 and a linear salt gradient from 0 to 16 mM NaCl. The chromatograms of mAb1 (pI=6.2) with the four buffers are displayed in FIG. 3A. The resolution between the charge variants evidently depended on the buffer concentration. With the 1 mM buffer, the charge variants were poorly separated. The resolution improved with the 2 mM buffer and peaked with the 4 mM buffer. However, the resolution significantly decreased with the 8 mM buffer. On the contrary, the resolutions for mAb2 (pI=8.2) were less sensitive to the buffer concentration than mAb1 (FIG. 3B). Good resolution for mAb2 (pI=8.2) was achieved with all four buffers even though the 4 mM buffer offered slightly better resolution than the other three buffers. Based on above visual inspection, the 4 mM buffer appeared to provide the best resolution for mAb1 and mAb2.

To better visualize the effect of buffer concentration on pH-IEC, the full width at half maximum (FWHM) of the main peak of mAbs plotted as a function of buffer concentration is shown in FIG. 3C. The FWHM of the main peak generally correlates with the resolution of pH-IEC in that the lower the FWHM represents the higher resolution. For both mAb1 and mAb2, the FWHM of the main peak with the 4 mM buffer was lowest among the four buffers, suggesting that the 4 mM buffer provided the narrowest peak width, thus good resolution. On the contrary for mAb3 (pI=9.4), the FWHM of the main peak slightly decreased when the buffer concentration increased from 1 to 8 mM. Thus the 8 mM buffer likely provided the best resolution for mAb3.

The effect of buffer concentration on pH-IEC of mAbs depended on the pI value of a mAb. The mAbs with low (6.2) and mid pI (8.2) values showed optimal separation with the 4 mM buffer, while the mAbs with high pI value (9.4) appeared to prefer higher concentration buffers. This is reasonable since the high pI mAbs strongly bind to column and thus may require more ionic strength-based elution than low and mid-pI mAbs to achieve optimal resolution. Since the buffer concentration and conductivity evidently impact the resolution of mAbs in pH-gradient IEC, these should be optimized for each individual mAb whenever high resolution is desired. An IEC method that can resolve acidic and basic variants from the main peak for mAbs over a wide pI range was developed. The 4 mM buffer appeared to meet this requirement and thus was chosen for the multi-product salt-mediated pH-IEC method.

Salt Concentration: To investigate how the ionic strength affects the pH-IEC separation, five different levels (0, 8, 16, 32 and 64 mM) of sodium chloride were added to the pH gradient (established by the 4 mM buffer) through a linear gradient from pH 5.0 to 10.8. mAb1, mAb2 and mAb3 were analyzed in parallel. The FWHM of the main peak of mAbs were plotted as a function of salt concentration as shown in FIG. 3D. For mAb1, the FWHM of the main peak was highly sensitive to the salt concentration and it reached to the minimum with 8 mM NaCl. This suggests that 8 mM NaCl provided the best resolution for mAb1. For mAb2, the FWHM of the main peak was essentially flat across the entire range of salt concentrations, suggesting that the salt concentration did not evidently impact the resolution of mAb2. On the contrary for mAb3, the FWHM of the main peak decreased with the salt concentration increasing from 8 to 32 mM and remained unchanged between 32 mM and 64 mM of salt. This suggests that mAb3 required 32 mM of salt to achieve optimal resolution.

The effect of the ionic strength on pH-gradient IEC of mAbs also correlated with the mAb's pI. The low pI mAbs showed separation with 8 mM of salt; the high pI mAbs showed separation higher concentration of salt, while the resolution of mid-pI mAbs was independent of salt concentration. Because of the evident impact on resolution, the salt concentration may be optimized for each individual mAb whenever high resolution is desired. Among the five salt concentrations, the pH-IEC method with a salt gradient of 16 mM NaCl provided acceptable resolution for mAbs with pI values over a broad range from 6.2 to 9.2 and thus it was chosen as the multi-product salt-mediated pH-IEC method in this work.

The Optimized ionic strength-mediated pH-IEC Method: The optimized salt-mediated pH-IEC method employed 4 mM piperazine, 4 mM imidazole, and 4 mM Tris to establish the pH gradient and was mediated with a linear salt gradient from 0 to 16 mM of NaCl. The pH and conductivity profiles of the method are shown as sold lines in FIG. 2C. For comparison, the modeled pH and ionic strength are shown as dashed lines. The experimental pH at the column exit increased with the retention time in a roughly linear fashion, except for a small concave at pH from 8.5 to 9.0 and it is consistent with the modeled pH except for a delay time of 5 minutes due to the system void volume. With the salt mediation, the experimental conductivity of the mobile phase showed a slight increase during the pH gradient (from 1570 to 1800 μS). Likewise, the modeled ionic strength was essentially consistent during the pH gradient. The ionic strength of the amine-based pH gradient was successfully controlled by reducing the buffer concentration and adding a linear salt gradient. With the controlled ionic strength, the column back pressure was maintained below 95 bar at the high pH region (FIG. 2D). The resulting chromatograms of mAb1-3 (not shown) were reproducible, indicating that the cation-exchange column was stable in this pressure range.

Example 4

Profiling the Charge Heterogeneity of 16 mAbs

Figure 4:
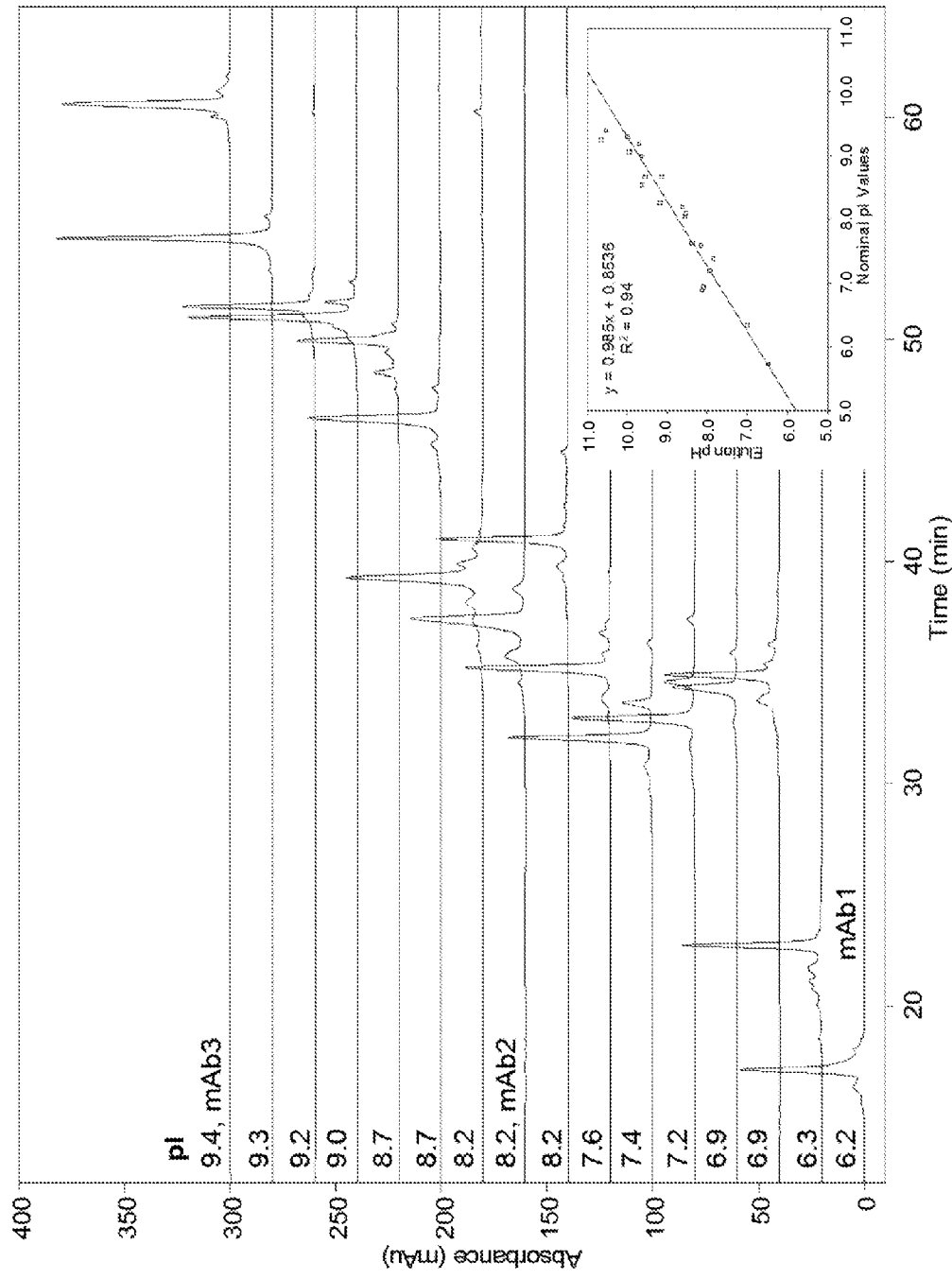
FIG. 4 shows the charge heterogeneity profiles obtained with ionic strength-mediated pH gradient IEC of sixteen monoclonal antibodies with pI's ranging from 6.2 to 9.4. Insert shows a graph of nominal pI values plotted against elution pH.

To further demonstrate the multi-product capability of the new salt-mediated pH-IEC method, 16 mAbs with pI values from 6.2 to 9.4 were analyzed and their chromatograms are shown in FIG. 4. Antibodies were eluted from the column with a pH gradient from pH 5 to pH 10.8 and a salt gradient from 0 mM NaCl to 16 mM NaCl. For both low pI mAb1 (6.2) and high pI mAb3 (9.4), the charge variants were well separated to yield acceptable charge heterogeneity profiles. This is a substantial improvement compared to the reported pH-IEC method (FIG. 1). The charge variants of all 16 mAbs were well separated, indicating that the developed salt-mediated pH-IEC method was capable of profiling the charge heterogeneity of multiple mAb products without any additional method development effort.

In addition to broader applicability, the salt-mediated pH gradient offered better resolution than the reported pH-IEC method. For mAb2 (pI=8.2), the salt-mediated pH-IEC method provided a baseline resolution between the charge variants (FIG. 4). However, the resolution by previous pH-IEC method was much lower (FIG. 1). Although the salt-mediated pH-gradient was longer (58 minutes) than the previous pH-gradient (45 minutes), the gradient slopes in the two methods were identical (0.1 pH unit/min). The improved resolution by the salt-mediated pH-IEC method was thus not a result of a change in gradient length, but rather from the effect of controlling the ionic strength.

Example 5

Monitoring the Thermal Stability of mAbs

Cation-exchange chromatography is commonly used to assess the degradation and lot-to-lot variation of biopharmaceutical proteins during manufacturing (Vlasak, J and Ionescu, R (2008) Curr. Pharm. Biotechnol. 9:468). To demonstrate the ability to monitor protein degradation, the developed ionic strength-mediated pH-IEC method was used to profile the charge heterogeneity of mAb1 after thermal stresses. mAb1 was chosen in this study because it has the lowest retention among the mAbs and its pH-IEC profile was most susceptible to changes in chromatography parameters. Antibody was eluted from the column with a pH gradient from pH 5 to pH 10.8 and a salt gradient from 0 mM NaCl to 16 mM NaCl.

Figure 5:
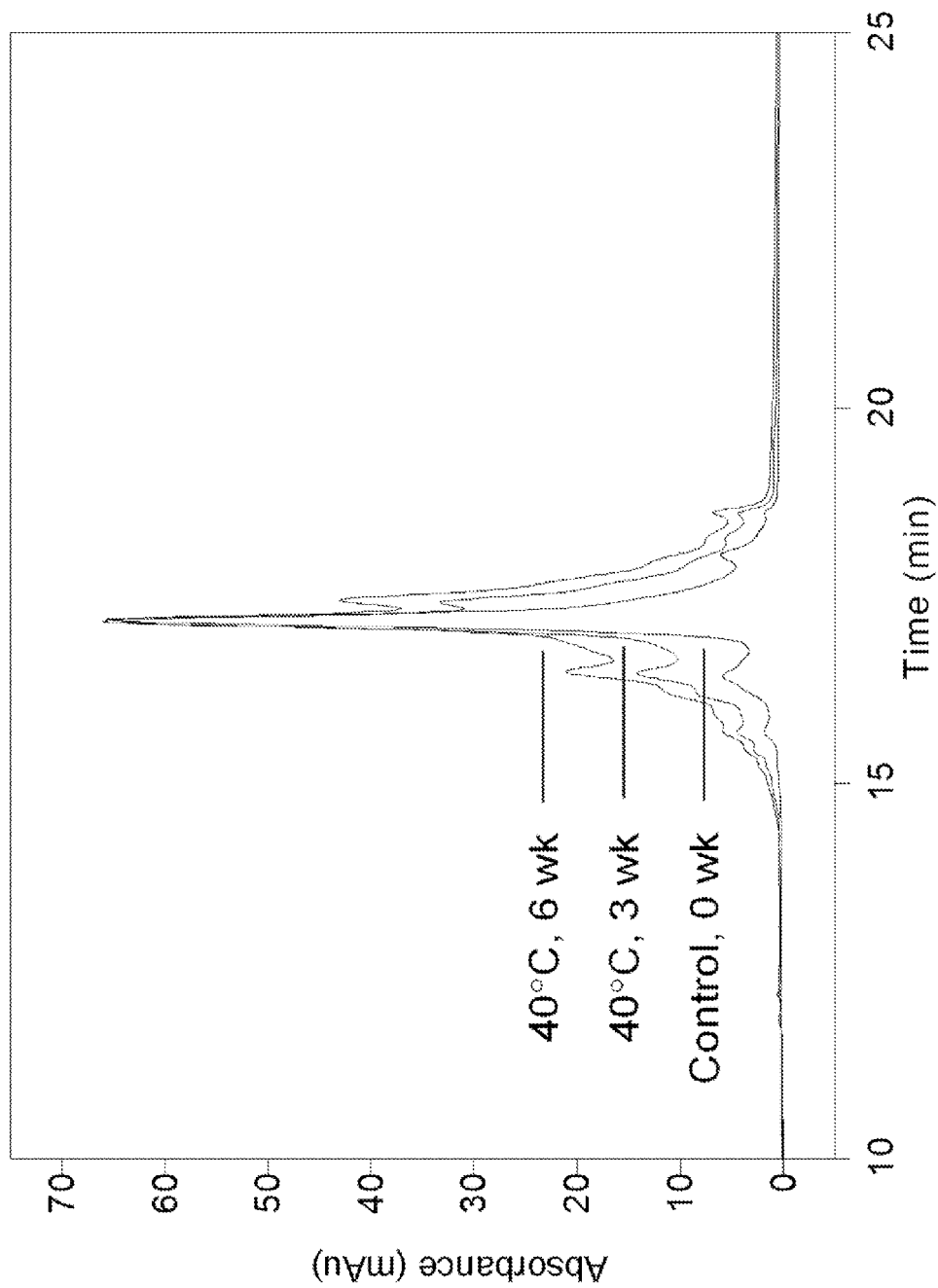
FIG. 5 shows the chromatograms obtained with ionic strength-mediated pH gradient IEC of native mAb1 (0 wk) and thermally stressed mAb1 (3 wk and 6 wk at 40° C.).

The chromatograms of control and stressed materials of mAb1 are normalized with the main peak (FIG. 5). After the thermal stresses, both acidic and basic variants increased. A shoulder also appeared to the right of the main peak for the stressed samples. These profile changes evidently indicate that mAb1 degraded after incubation at 40° C. for 3 and 6 weeks. Likewise, the degradation of mAb2 and mAb3 under thermal stresses was also detected by the salt-mediated pH-IEC method (data not shown).

Example 6

Robustness Testing of the Ionic Strength-Mediated pH-IEC

Because of the complex elution process of the salt-mediated pH-IEC method, it is necessary to ensure its robustness for routine sample testing. As discussed above, we know that the pH buffer composition and the salt concentration affected the retention and resolution of mAbs. The purpose of further studies here was to investigate the variability originated from column, buffer lot, and instrument when the optimized pH buffer composition and salt concentration were used. Three columns, three buffer lots, two instruments were tested in four different days. The experimental design is shown Table 3. mAb1 was again chosen in the studies because its pH-IEC profile was most susceptible to changes in chromatography parameters.

The chromatograms of mAb1 obtained with different columns and buffer lots were comparable, but those obtained with different instruments showed slightly different retention time. The difference in the delay volumes expected between instruments accounted for the variation in the retention time, but it doesn't impact the performance of the method. The quantitation of the charge variants of mAb1 is summarized in Table 4. For the 16 chromatograms obtained with two different instruments, three columns and three buffers preparations, the quantitation of the charge variants was consistent, indicating that the salt-mediated pH-IEC was robust at these chromatography conditions.

TABLE 3

The experimental design for the robustness test of the salt-mediated pH-IEC using mAb1

|  | Day 1 | Day 2 | Day 3 | Day 4 |
|---|---|---|---|---|
| Waters 2796 | X | X | X |  |
| Dionex U3000 |  |  |  | X |
| Column 1 | X |  |  |  |
| Column 2 |  | X | X |  |
| Column 3 |  |  |  | X |
| Buffer 1 | X | X |  |  |
| Buffer 2 |  |  | X |  |
| Buffer 3 |  |  |  | X |

TABLE 4

Summary of the robustness data (n = 16) of the salt-mediated pH gradient obtained for mAb1

|  | Acidic Variants | Main Peak | Basic Variants |
|---|---|---|---|
| Average | 12.32 | 78.99 | 8.69 |
| Highest | 13.20 | 79.92 | 9.54 |
| Lowest | 10.54 | 77.91 | 8.14 |
| STD deviation | 0.78 | 0.56 | 0.55 |
| % RSD | 6.3 | 0.7 | 6.4 |

Figure 6:
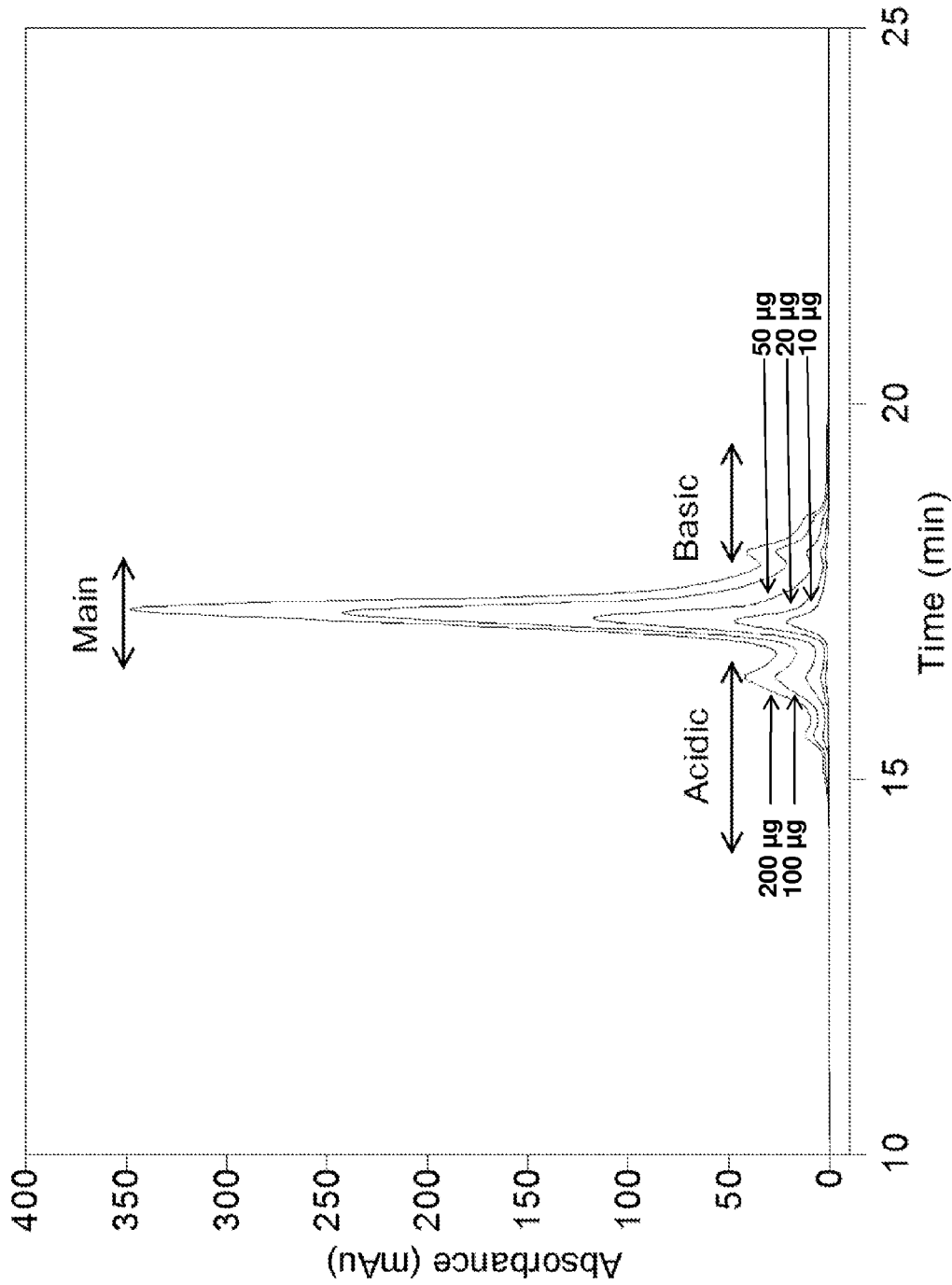
FIG. 6 shows chromatograms of mAb1 with 10, 20, 50, 100 and 200 μg of column load obtained with the ionic strength-mediated pH gradient IEC.

The salt-mediated pH gradient IEC was also robust across a wide range of sample mass loadings on column. As shown in FIG. 6, consistent elution profiles were observed when 5-200 μg of mAb1 was loaded on the column. Although the main peak slightly broadened when the column load was over 50 μg, the quantitation of the charge variants was consistent among all the tested column loads (Table 5).

During the course of the robustness studies, sufficient data was obtained to cover most variables that are experienced in a typical HPLC experiment. The salt-mediated pH-IEC method provides comparable chromatograms and consistent quantitation results of charge variants for a typical mAb, demonstrating that the method is robust at all chromatography conditions studied here.

TABLE 5

The robustness of the charge heterogeneity of mAb1 at different column loads

| Column Load (μg) | Acidic Variants | Main Peak | Basic Variants |
|---|---|---|---|
| 5 | 12.66 | 79.04 | 8.30 |
| 10 | 13.04 | 78.84 | 8.12 |
| 50 | 13.27 | 78.14 | 8.59 |
| 100 | 13.58 | 77.80 | 8.62 |
| 200 | 13.55 | 77.86 | 8.59 |
| Average | 13.22 | 78.34 | 8.44 |
| STD deviation | 0.38 | 0.57 | 0.22 |
| % RSD | 2.9 | 0.7 | 2.6 |

Example 7

Reducing Run Time for Ionic Strength-Mediated pH-IEC

Figure 7:
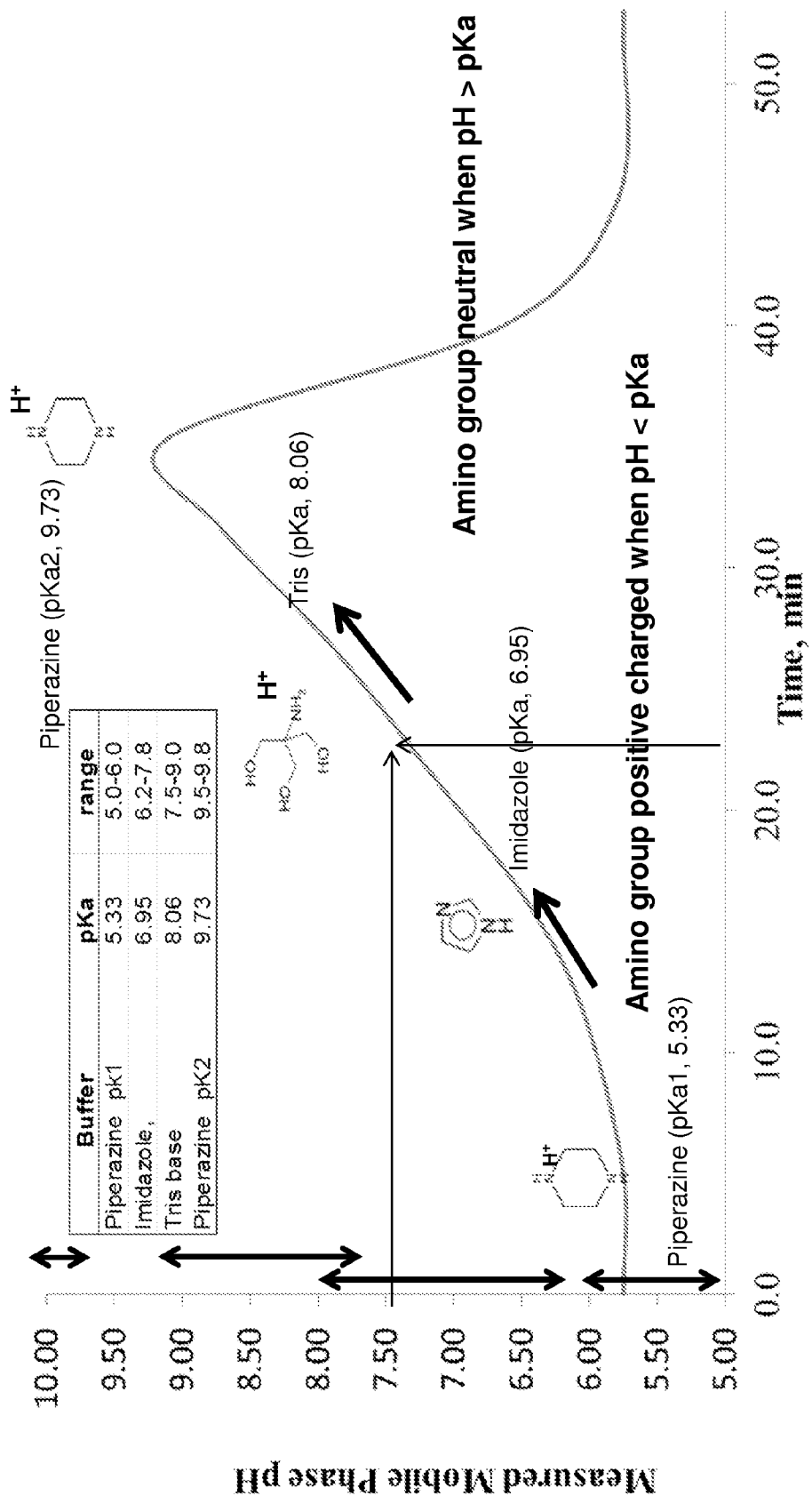
FIG. 7 shows the buffering through amino functional groups of a piperazine, imidazole, Tris (PIT) buffer solution in a semi-linear pH gradient from pH 6 to pH 9.5.
Figure 8:
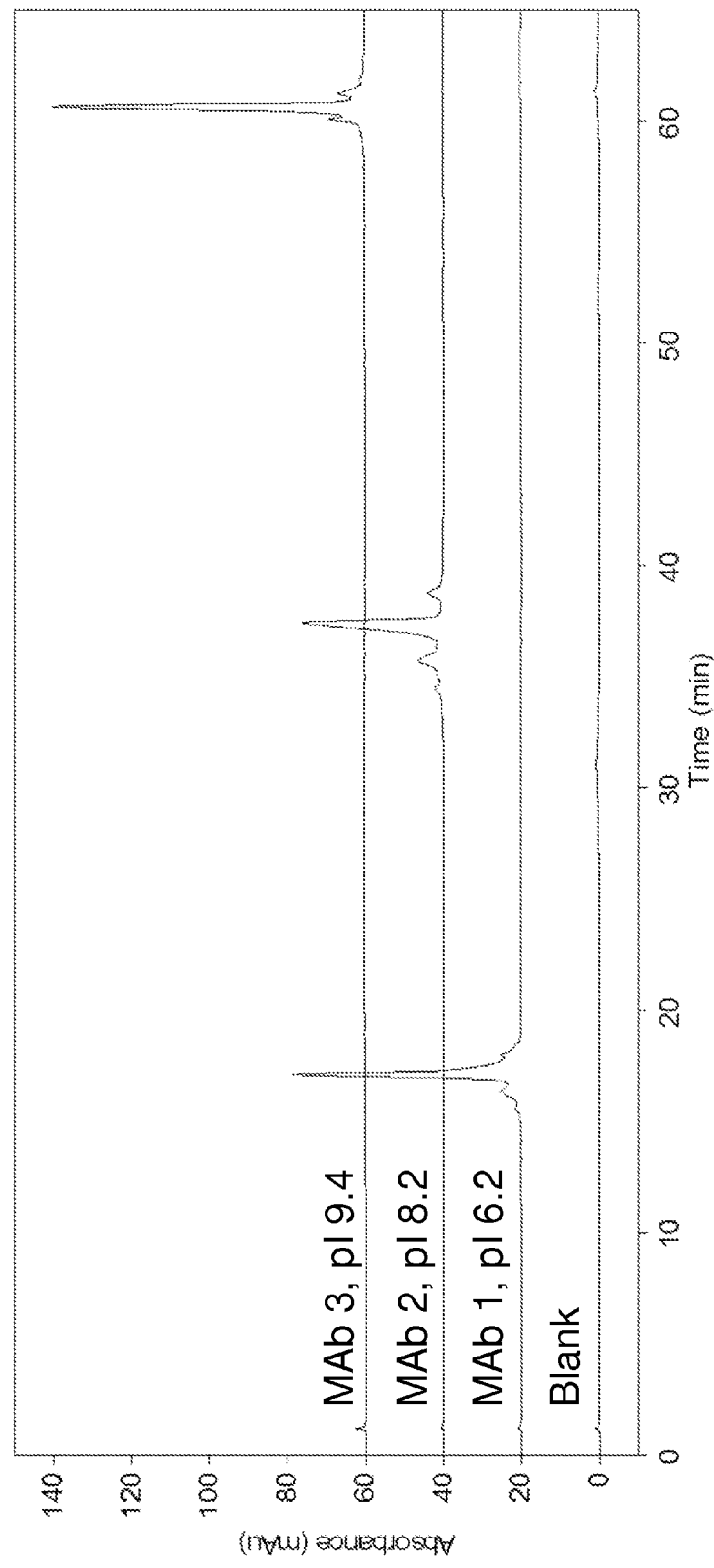
FIG. 8 shows chromatograms of mAbs with pI's ranging from pI 6.2 to pI 9.4 using ionic strength mediated IEC. The column was a Propac WCX-10, 4×250 mm.

Previously, pH-mediated IEC methods used piperazine, imidazole, tris (PIT) as buffering reagents (Farnan, D and Moreno), GT 2009 Anal. Chem. 81:884-8857). To generate a pH gradient, a semi linear pH curve was generated from pH 6 to 9.5 The amino functional group of each buffering agent maintains a positive charge when the mobile phase pH is less than the reagent's pKa and neutral when the mobile phase pH is greater, as shown in FIG. 7. The pH gradient was generated using Buffer A (pH 5.0) and Buffer B (pH 9.5) in a gradient from pH 5 to pH 9.5 in 35 minutes. The column was a Propac WCX-10, 4×250 mM. This buffer reagent system pH gradient works well for large range of molecules with pI values between 7 and 8.5. However, the charge variants for molecules outside this working range are not resolved as well. Preliminary work revealed that the concentration and ionic strength of the buffering reagents influenced the linearity of the pH curve and the retention times of sample. As shown in Example 2, ionic strength dramatically decreases as pH increased over time. Adjustments to buffer concentrations and the introduction of a simultaneous salt gradient provided a rather stable ionic strength throughout the pH gradient. With a simultaneous salt gradient, pH-gradient separation can now resolve molecular variants with pI values from 6.2-9.4. As shown in FIG. 8 using a long gradient of 58 min, where the pH increased from pH 5 to pH 10.8 at a slope of 0.1 pH unit/min and the salt concentration increased from 0 mM NaCl to 16 mM NaCl in a PIT buffer (4 mM piperazine, 4 mN imidazole, and 4 mM Tris) monoclonal antibodies with pI values of 6.2 (Mab1), 8.2 (Mab 2) and 9.4 (Mab3) are resolved. The improved method is referred to as an "ionic strength-mediated pH gradient" or a "salt-mediated pH gradient".

Figure 9:
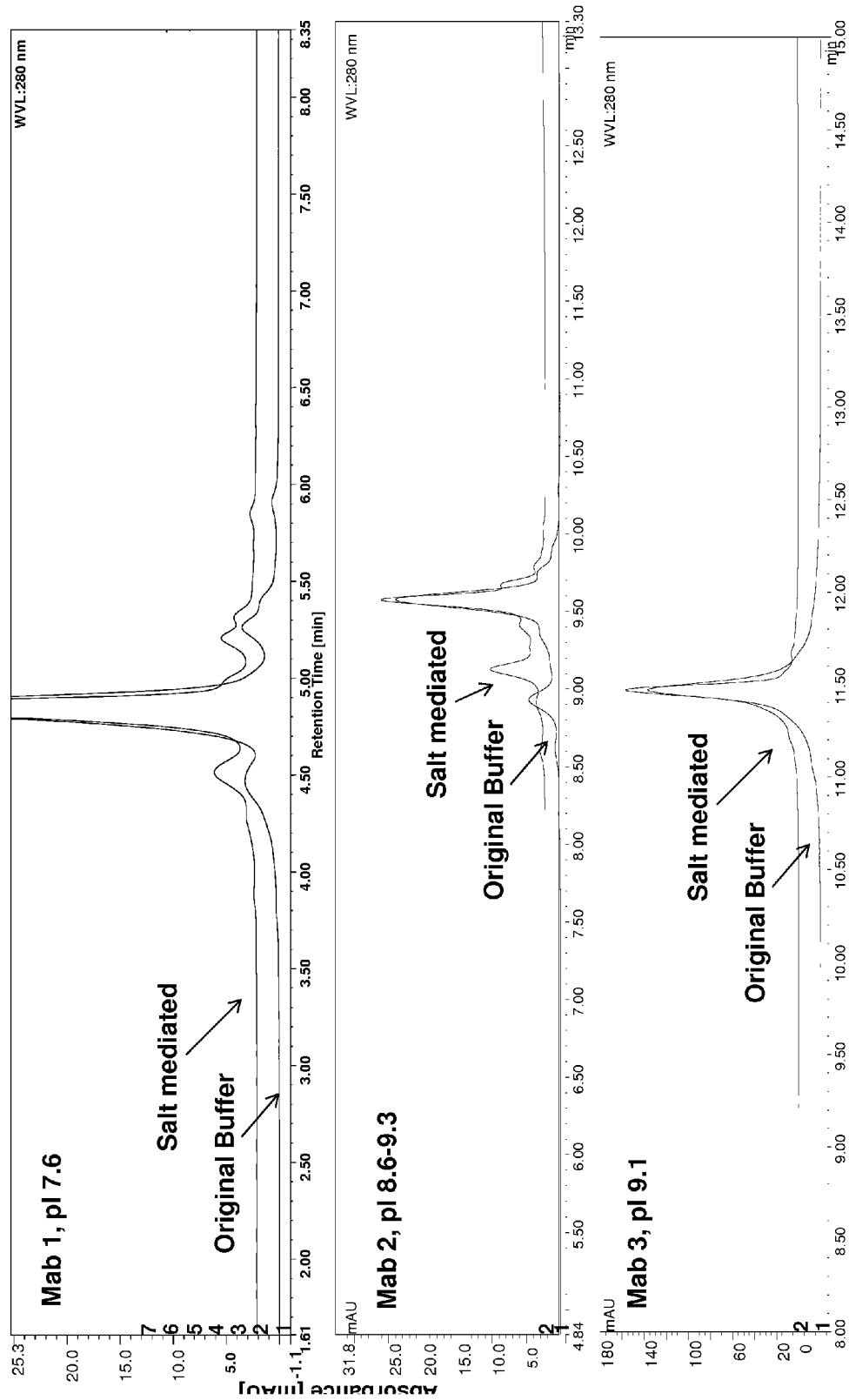
FIG. 9 shows that similar profiles are observed between original pH-IEC and ionic strength-mediated pH-IEC when using a 4×250 mm column.

To reduce run time and increase throughput, the salt-mediated pH gradient on a shorter column (4×50 mm) was evaluated. Farnan, D and Moreno, G T (2009) Anal. Chem. 81:8846-8857 indicated that similar elution profiles were obtained using pH-IEC regardless column length, provided it was the same pH-IEC separation mode (WCX or SCX). To determine if shorter columns could reduce elution times, the separation of three Mabs with different pI values using both the original pH-IEC and salt-mediated pH-IEC mobile phases using a WCX-10, 4×50 mm column were compared. The mAbs were Mab 1, pI 7.6; Mab 2, pI 8.6-9.3; and Mab 3, pI 9.1. The pH gradient was pH 6-11 in 0-16 min, held at pH 11 for 2 min, and followed by a 4 min re-equilibration at pH 6 for a total run time of 22 minutes. The buffer for the original pH-IEC was 2.4 mM Tris, 1.5 mM imidazole, and 11.6 mM piperazine. The buffer for the ionic strength-mediated pH-IEC was 4 mM Tris, 4 mM imidazole, and 4 mM piperazine with 16 mM NaCl. As seen in FIG. 9, although similar peak profiles were obtained for these three Mabs, the resolution of charge variants decreased as molecule's pI increased. In order to achieve adequate separation for molecules with a wide pI range in less run time, an investigation into variant separation mechanism and different buffer system was initiated.

Figure 10:
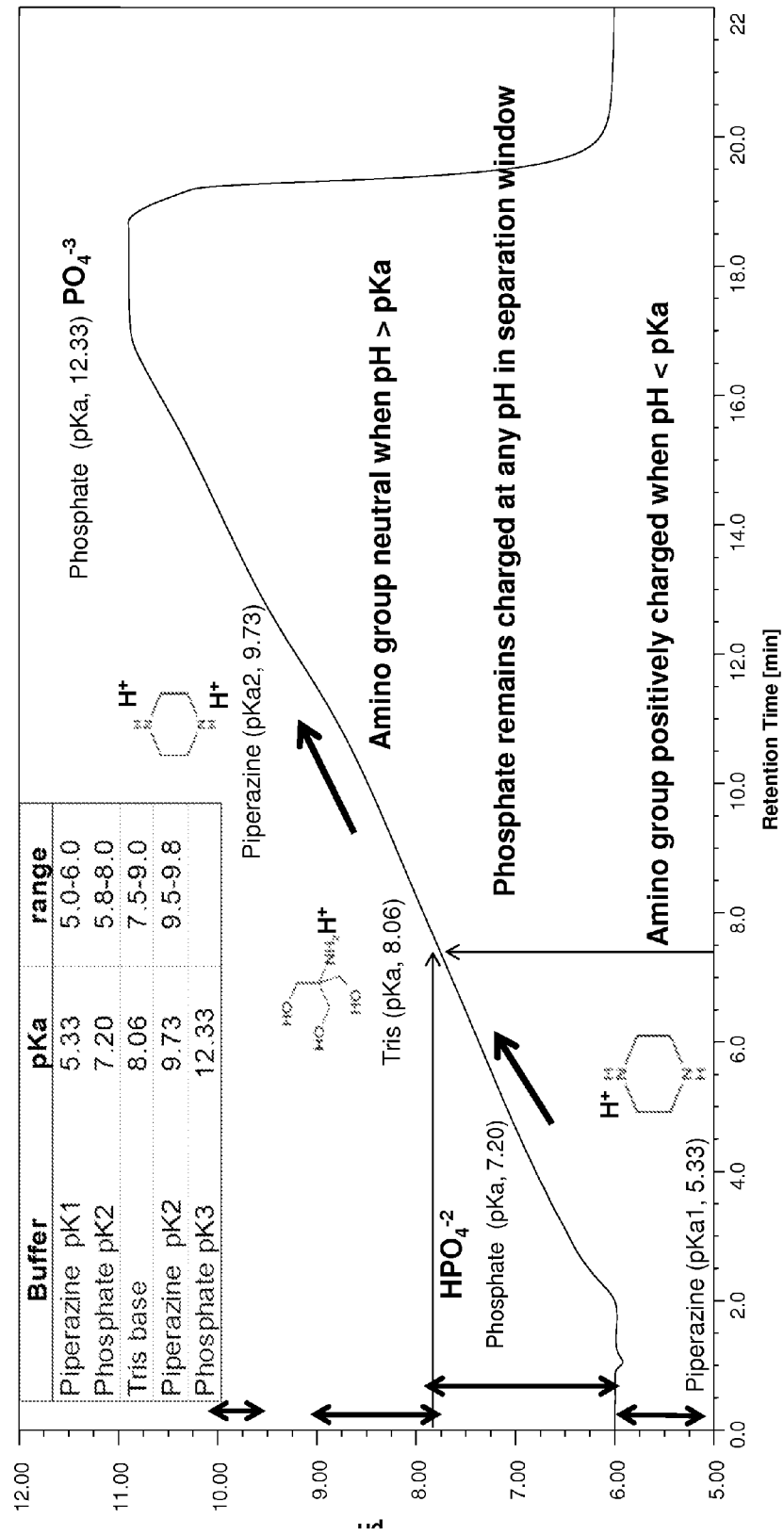
FIG. 10 shows a model linear pH gradient from pH 6 to pH 11 using phosphate to maintain conductivity as pH increases.
Figure 11:
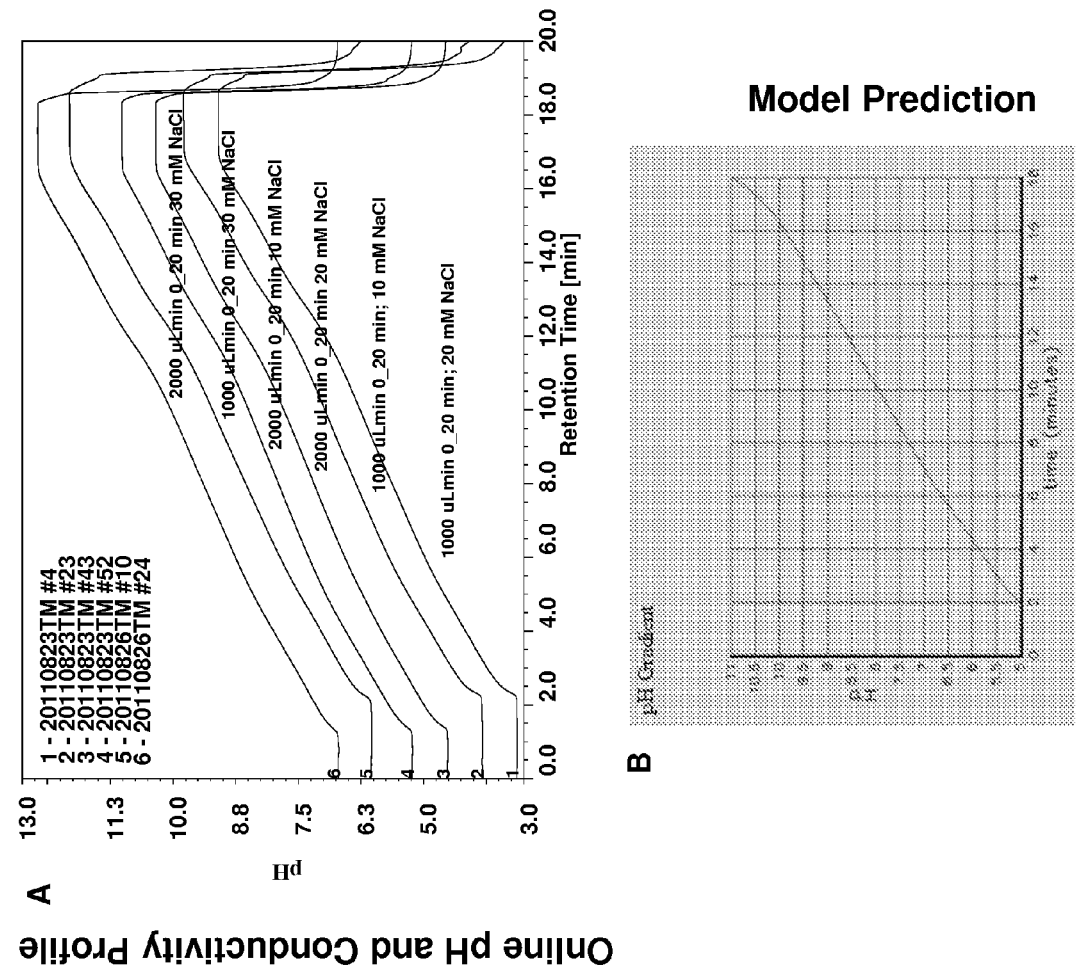
FIG. 11 are graphs showing that observed pH (Panel A) and conductivity (Panel C) profiles are consistent with model predictions (Panels B and D).
Figure 11:
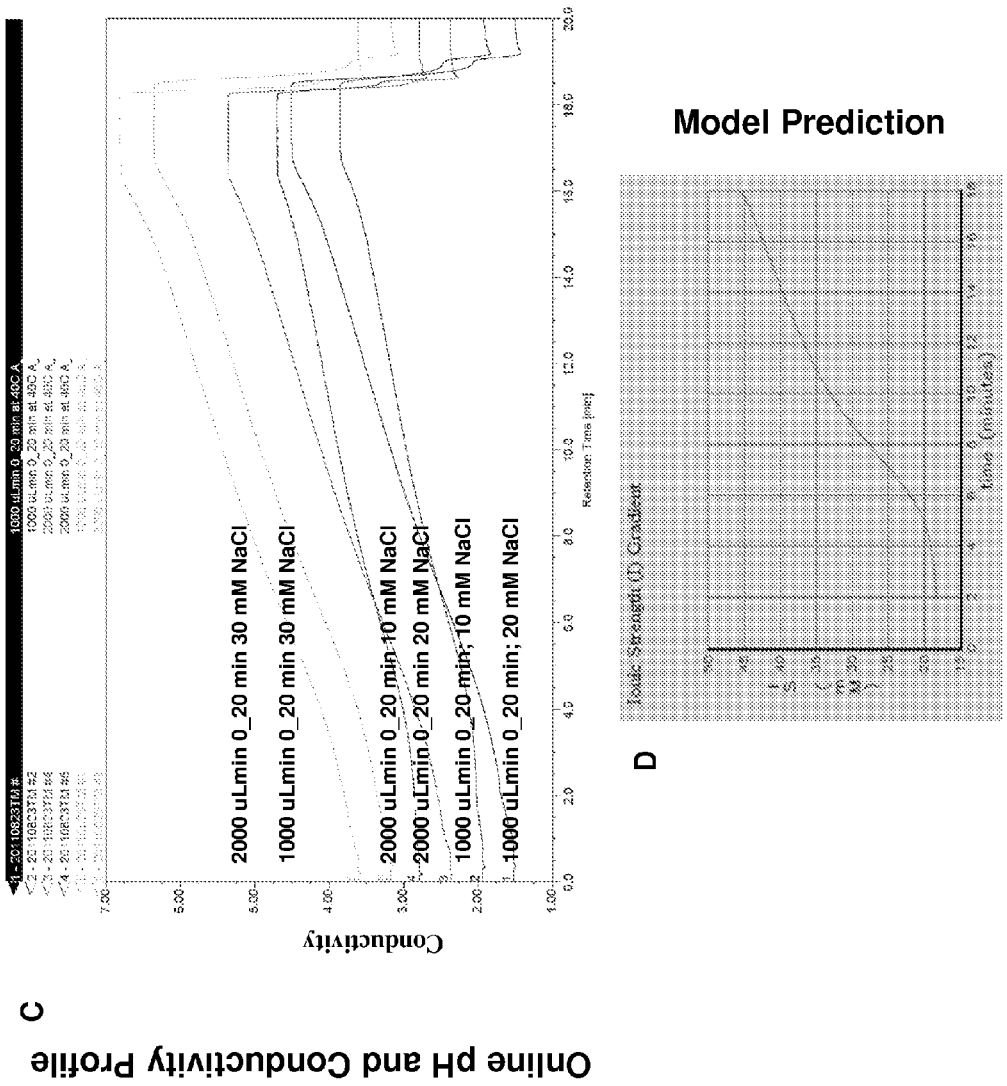

To assist in buffer screening, a pH and conductivity prediction tool may be used. The pH and conductivity curves of commonly used buffers and NaCl salt at different combinations, pH range and gradient times can be calculated and plotted based on buffer's pKa. The visualization prediction tool allows quick optimization of the buffer system which has desired properties, such as a linear pH curve, stable or increasing ionic strength over time, and lower buffer toxicity. Using this model, various buffer combinations were screened. The combination of Tris, piperazine and phosphate (TPP) buffers was found to form a linear pH gradient over 16 minute gradient (FIG. 10). Buffers included piperazine pK1 with a pKa of 5.33 (range 5.0-6.0), phosphate pK2 with a pKa of 7.20 (range 5.8-8.0), Tris base with a pKa of 8.06 (range 7.5-9.0), piperazine pK2 with a pKa of 9.73 (range 9.5 to 9.8) and phosphate pK3 with a pKa of 12.33. The plot in FIG. 10 elucidates that the phosphate molecule remains charged throughout the pH range, and compensates, to a certain extent, the ionic strength loss due to the deprotonation of amino functional groups in Tris and piperazine as the pH increases. The chromatography conditions were as follows:

Column: Propac WCX-10HT, 4×50 mm
pH gradient: 5.0 mM Tris, piperazine, phosphate (TPP)
Buffer A=pH 6.0
Buffer B=pH 11.0 Gradient: 6-11 in 16 min
Buffer C=60 mM NaCl
Buffer D=MilliQ water The predicted pH and conductivity curves (FIG. 11 right panel) were consistent with those obtained experimentally (left panel). The buffer system contained 5 mM of Tris, piperazine, and phosphate, and a constant NaCl concentration at either 10 mM, 20 mM or 30 mM (used in model). The experimental flow rate was 1 mL/min or 2 mL/min.

Example 8

Determining Optimal Ionic Strength Ranges

Figure 12:
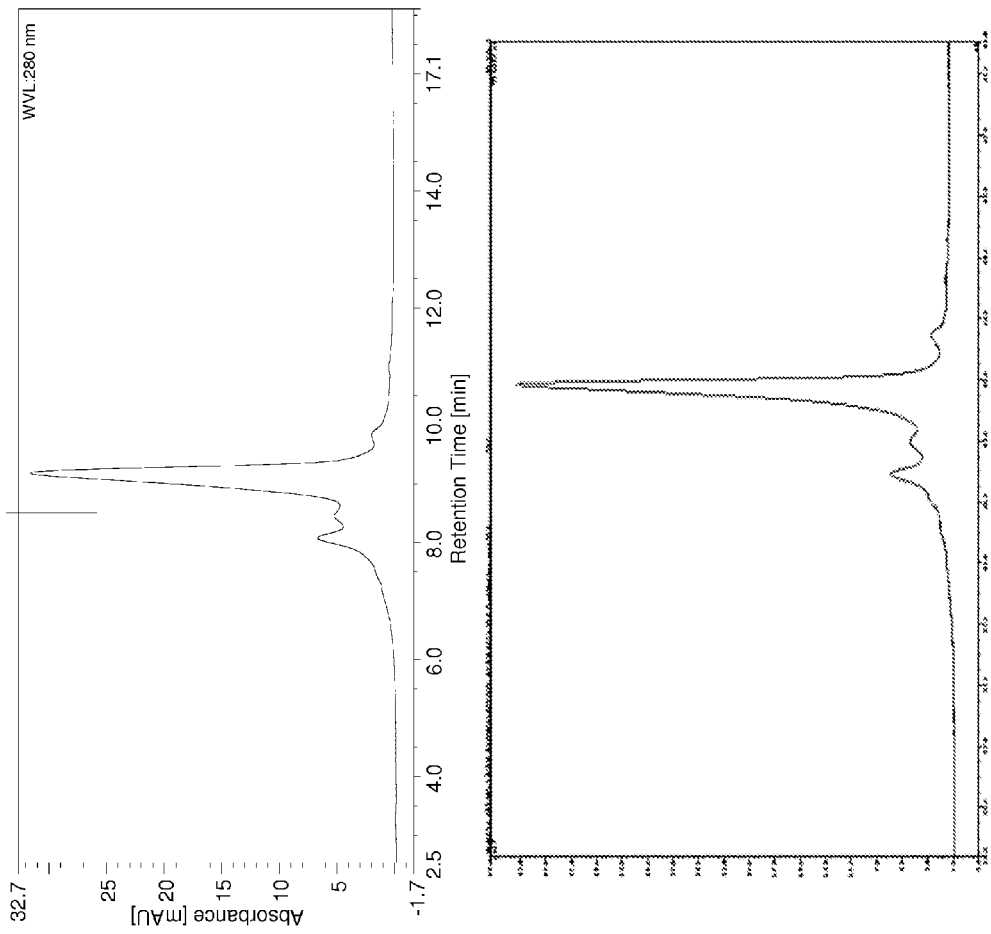
FIG. 12 shows that shorter runs are possible using TPP buffers. Top chromatogram shows results with a 4×50 mm Propac WCX-10HT column with a 16 minute gradient and bottom chromatogram shows results with a 4×250 mm column with a 58 minute gradient.

Various samples were analyzed using the 16 minute gradient salt-mediated TPP method. An example of consistent profiles between 22 and 58 minute methods from 4×50 and 4×250 Propac WCX-10 columns, respectively is shown in FIG. 12. The elution with the 4×50 column was with salt-mediated Tris/Piperazine/Phosphate (TPP), pH 6-11 and 0-30 mM NaCl over 16 min. The elution with the 4×250 column was with salt-mediated Piperazine/Imidazole/Tris (PIT) pH 5-10.8 and 0-16 mM NaCl over 58 min. It was determined that the salt-mediated TPP method was sufficient for molecules mainly in the pI range of 7-8.5, which was the similar range obtained with the original PIT method. It was concluded that the buffer reagents and ionic strength plays a part in separation but that other factors may be involved.

Figure 13:
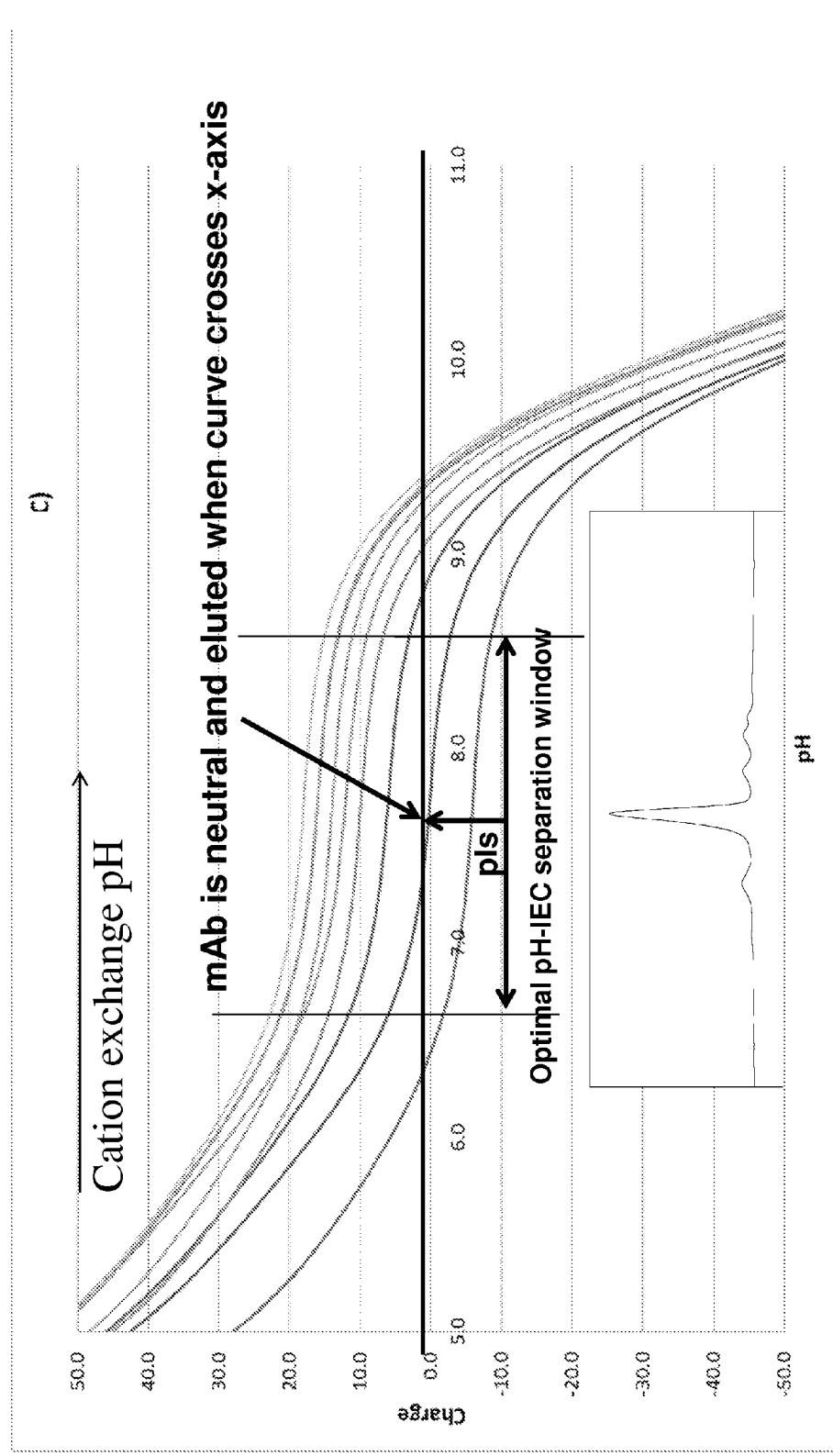
FIG. 13 is a graph demonstrating the charge state of different molecules at different pH using a modeling tool that calculates the charge of monoclonal antibodies with different pI's. The charge on a monoclonal antibody is neutral when it crosses the X-axis. The suitable pH-IEC separation window corresponds to the pH range where the curve is relatively flat.

The net charge state of MAbs over a pH range was modeled. FIG. 13 shows an overlay of net charges over pH for mAbs with different pI's. In the cation exchange mode, a mAb carries a positive charge until the pH decreases to reach its pI (x-intersect), and then is eluted from the column. As the pH increases, the mAb becomes negatively charged. The charge variant profile for a given protein molecule consists of a main peak, an acidic, and a basic region (as shown on the bottom panel). Usually, a charge variant is one or few charges apart from the main peak, with the entire charge envelop from the most acidic to the most basic variant spanning across 5-7 charges. The optimal pH-gradient separation window may lie across curve's flat region between pH 6.5 to pH 8.5 (FIG. 13); e.g. for molecules with pI values less than about 8.5, the net charge immediately below its theoretical pI changes very little and the curve is relatively flat between pH 6.5 and 8.5. In a pH gradient run, there is sufficient time for charge variants to be eluted off the column separately at different retention times as the pH increases over time.

Figure 14:
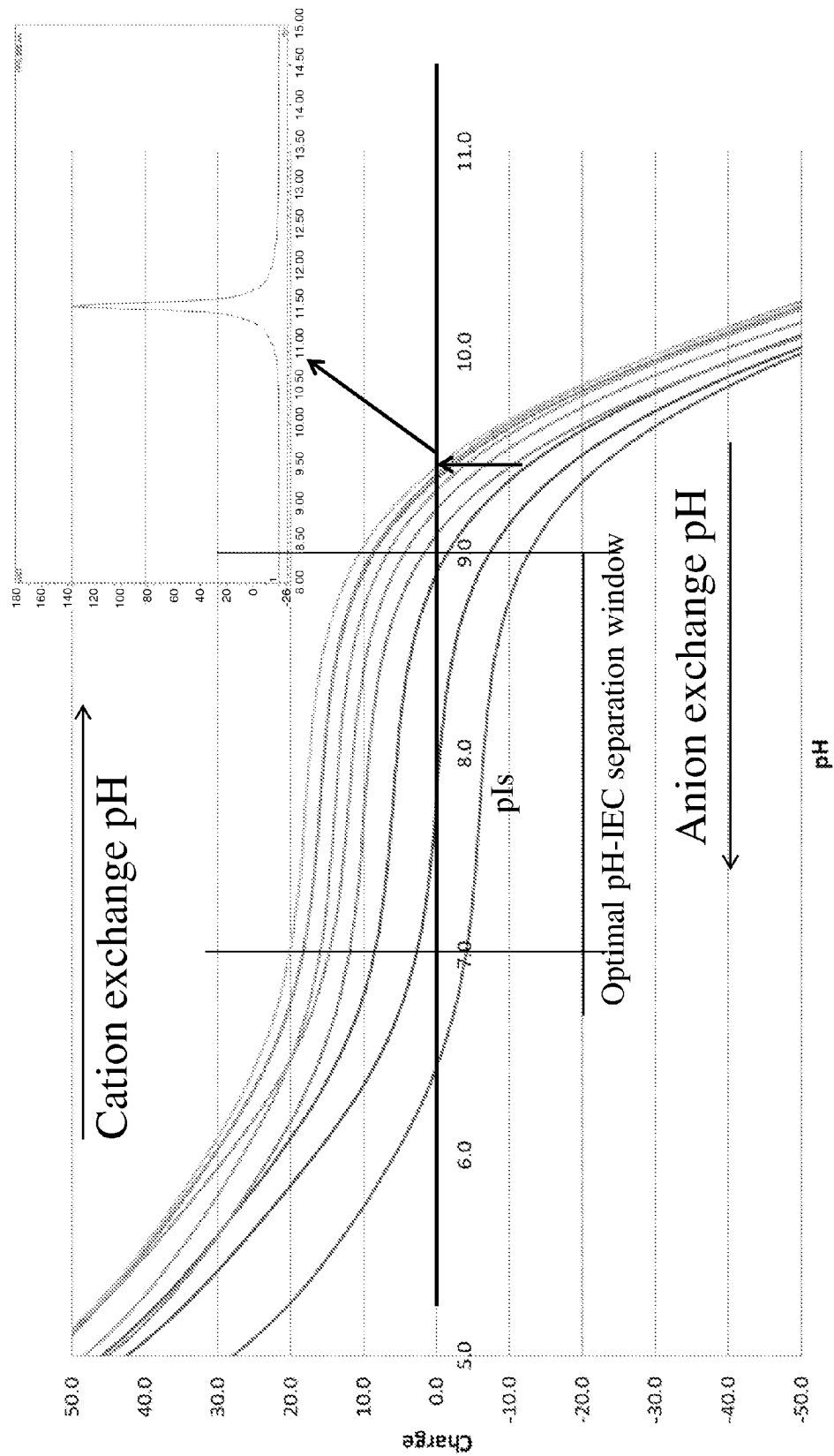
FIG. 14 is a graph showing that at high pI, molecules have less time to resolve as pH increases.

Conversely, for molecules with pI values greater than 8.5 and less than 6.5, the net charge changes dramatically at its theoretical pI's (FIG. 14). During a platform linear pH-gradient run, the charge per min slope is too steep at these pHs to allow adequate separation and one peak is observed (inset).

Since better peak separation and robustness was achieved in the relatively flat portion of the charge vs. pH curve, the question is how to elute protein charge variants in this region regardless their pI. This requires a pre-modification of charge state for higher pI molecules using factor other than pH. This factor is buffer ionic strength. With higher ionic strength in the mobile phase, more charges on the molecule surface are shielded from the stationary phase. Therefore, the apparent net charge decreases to allow the variants being eluted at pH below its pI.

In the work presented in Examples 1-6, charge variants of molecules with pI values greater than 9 (cation exchange mode) and less than 7 (anion exchange mode) were separated well by correcting the ionic strength deficiencies in the PIT mobile phases combined with a salt gradient (salt mediated pH-gradient). The combined driving force of pH and salt gradient allows for molecule's apparent charge state decreases faster over time as compares to the pH-gradient alone. This can be illustrated as the apparent charge vs. pH curve get stretched vertically, with a narrower flat region between pH 7-8, and a shallower slope at pH greater than 9. Therefore, for molecules with higher pIs, the separation took place at pH slightly below their pIs. Using a longer column (250 mm) and long run time (60 min), there was sufficient time for charge variants to elute. However, the salt mediated pH-gradient method failed to resolve charge variants for high pI molecules on a shorter column (50 mm) in a short run time (20 min).

Since short run time is critical, instead of gradually decreasing the apparent charge with a salt gradient over 60 min, the desired charge state can be reached at the beginning of the run by introducing salt early and kept constant throughout.

Figure 15:
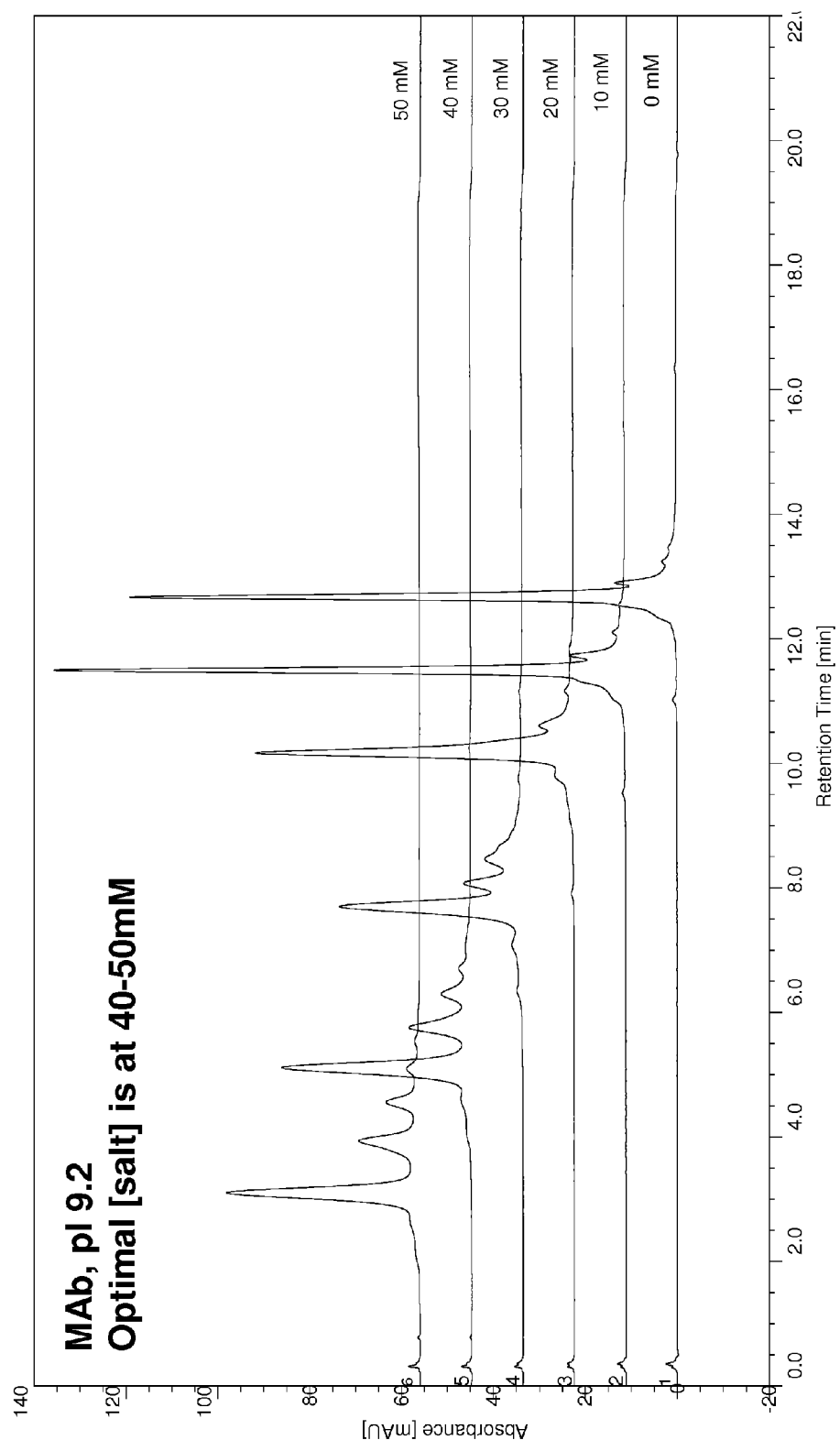
FIG. 15 shows the results of a study to determine the optimal salt concentration for the best charge shielding effect of an antibody with a pI>9.0. Salt concentrations of 0 mM, 10 mM, 20 mM, 30 mM, 40 mM and 50 mM were tested.

FIG. 15 is an overlay of pH-gradient separations of a high pI mAb (pI 9.2) in the presence of NaCl salt at different concentrations. Using a quaternary system, a pH gradient from pH 6-11 was created using the A and B lines and NaCl salt concentrations of 0, 10, 20, 30, 40 or 50 mM was maintained using the C and D lines. Gradient conditions and run times were as follows: Instrument: U3000 2DLC; Mobile phases: 10 mM Tris, piperazine, phosphate, A) pH 6.0, B) pH 11.0; C) 100 mM NaCl, D) milliQ water; Column: Propac WCX-10, 4×50 mm, 10 µm; Column temp: 40° C.; Flow rate: 1 mL/min; pH Gradient: 10-50% B; salt constant: 0 mM=0% C, 50% D; 10 mM=10% C, 40% D; 20 mM=20% C, 30% D, 30 mM=30% C, 20% D, 40 mM=40% C, 10% D, 50 mM=50% C, 0% D; Sample conc.: 1 µg/µL; Loaded volume: 20 µL.

At lower salt concentration, very little separation was observed. At subsequently higher salt concentrations, the separations improved while the elution time decreased. The decreasing elution time with increasing salt concentration supports that extra charges on the molecule surface are shielded from the stationary phase so that the apparent charge decreases to allow for variant separation at pH below its pI. In this case, an optimal separation was achieved at 40-50 mM NaCl, at which the apparent charge of this mAb presumably resided in the relatively flat portion of the charge vs. pH curve.

Figure 16:
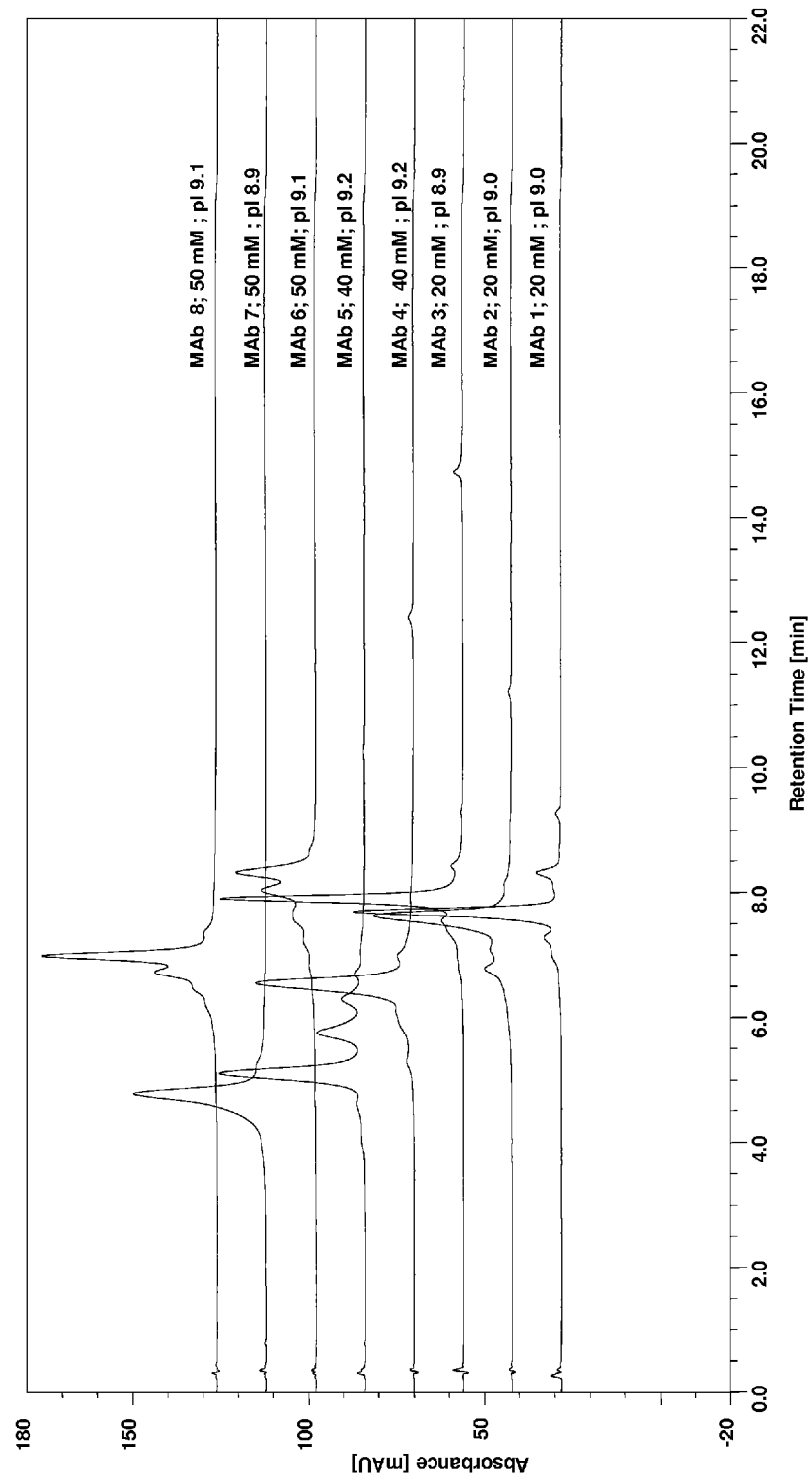
FIG. 16 shows the results of a study to determine the optimal salt concentrations for the best charge shielding effects for antibodies with pI's ranging from 8.9 to 9.1.
Figure 17:
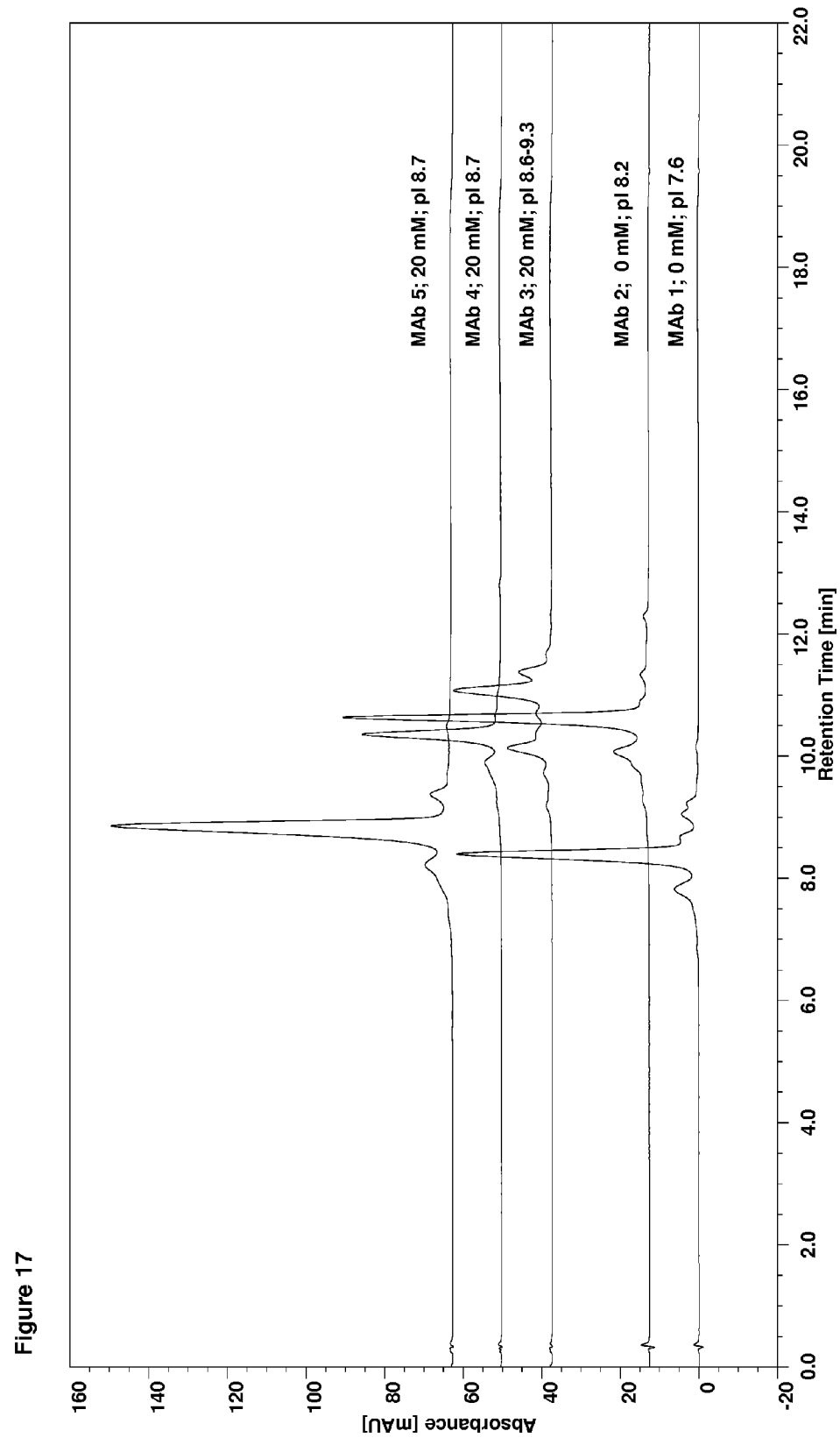
FIG. 17 shows the results of a study to determine the optimal salt concentrations for the best charge shielding effects for antibodies with pI's ranging from 7.6 to 8.7.
Figure 18:
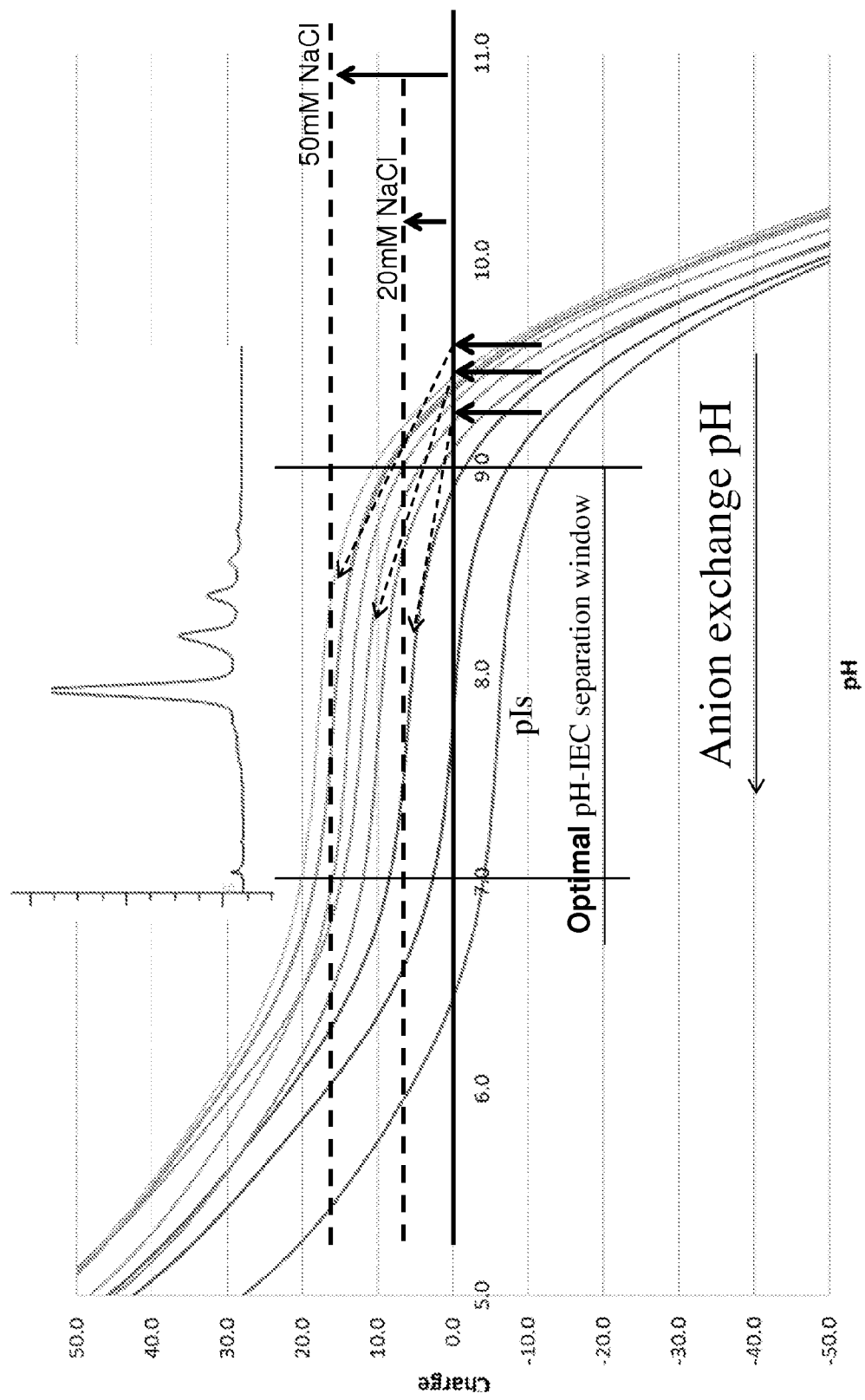
FIG. 18 is a graph showing that adding salt to shield extra charges moves the charge state into a suitable separation window.

Analysis of various mAbs with different pIs were performed at different constant salt concentrations while applying the same pH gradient. Generally, the optimal separation was achieved at a constant salt concentration at such that the apparent charge state falls in the flat portion of the charge vs. pH curve. For example, mAbs in the pI range of 7-8.3 needed no salt, those in the pI range of 8.3-8.8 needed 20 mM salt and those in the pI range of 8.8-9.0 needed 50 mM salt (FIGS. 16 and 17). On the charge vs. pH curve, the addition of salt essentially moves the x-axis up to the desired charge state of the molecule to allows for optimal separation in the flat region of the curve. This type of separation is referred to as a "hybrid" pH-gradient (FIG. 18).

Figure 19:
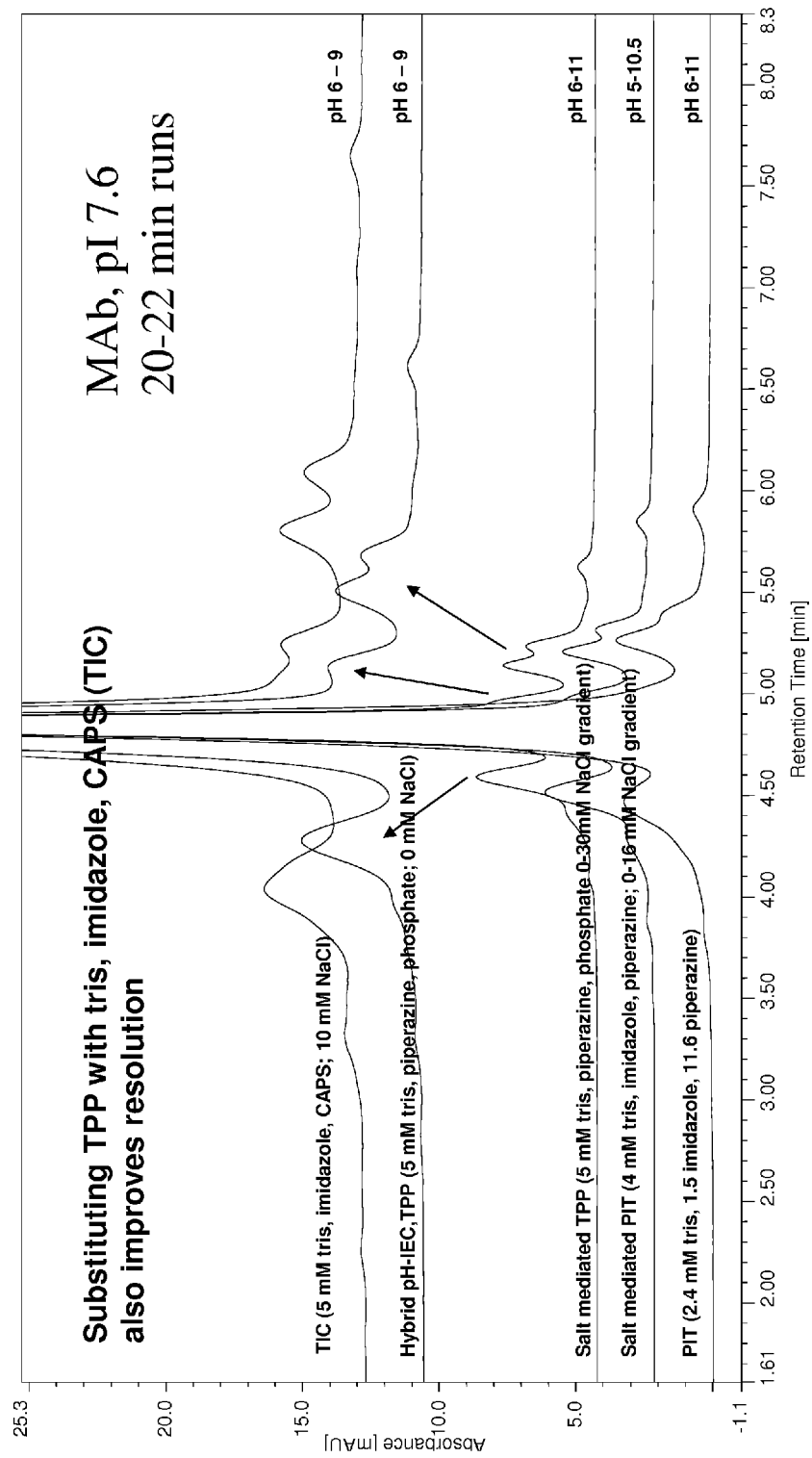
FIG. 19 is a graph showing that using a shallow pH gradient may improve peak resolution using a MAb with a pI of 7.6. Gradients tested were as follows: PIT (2.4 mM Tris, 1.5 mM imidazole, 11.6 mM piperazine, pH 6-11); salt mediated PIT (4 mM Tris, 4 mM imidazole, 4 mM piperazine, pH 6-11, 0-16 mM NaCl gradient); salt mediated TPP (5 mM Tris, 5 mM piperazine, 5 mM phosphate, pH 6-11, 0-30 mM NaCl gradient); hybrid pH-IEC, TPP (5 mM Tris, 5 mM piperazine, 5 mM phosphate, pH 6-9, 0 mM NaCl); TIC (5 mM Tris, 5 mM piperazine, 5 mM CAPS, pH 6-9, 10 mM NaCl). Runs were 20-22 minutes.
Figure 20:
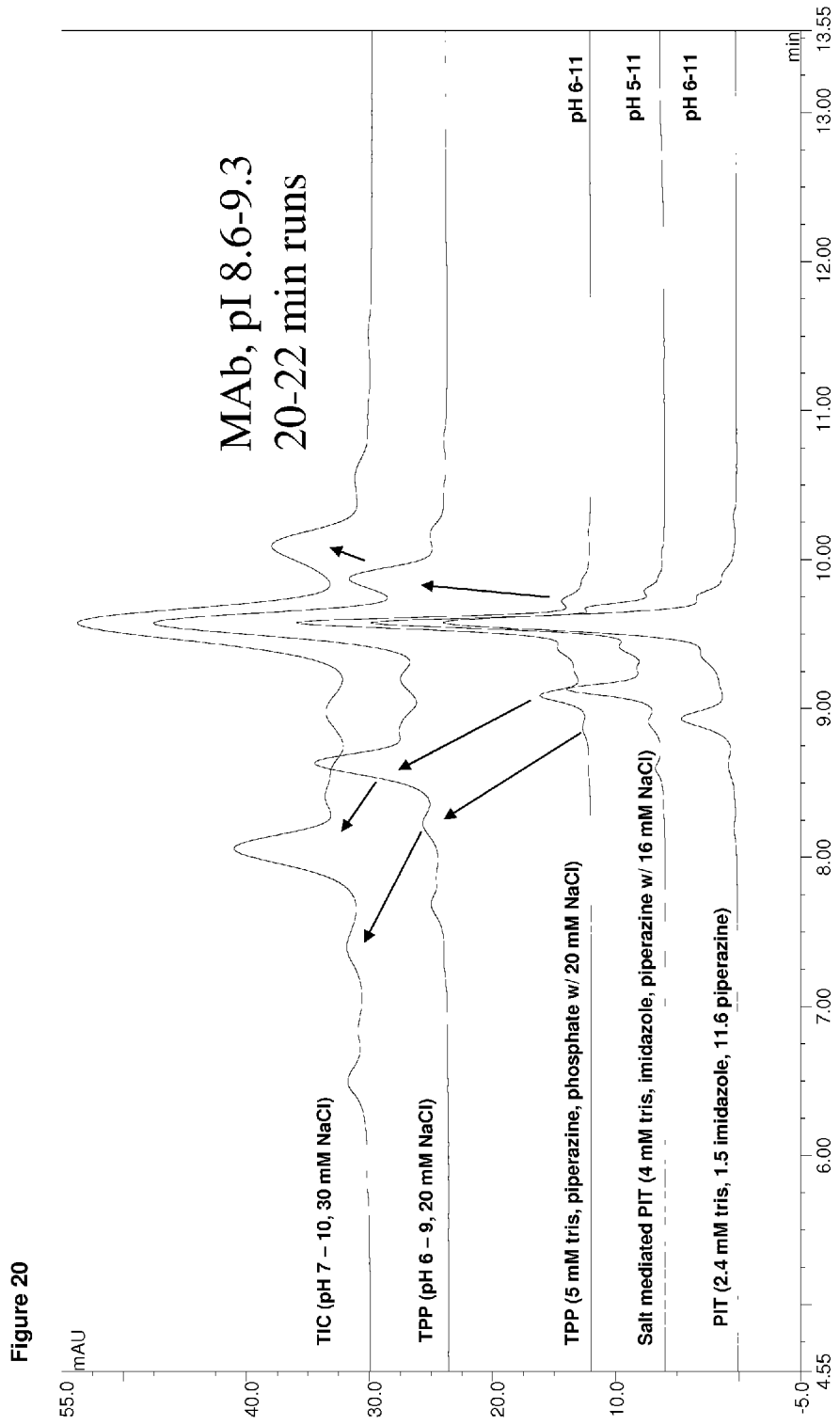
FIG. 20 is a graph showing that using a shallow pH gradient may improve peak resolution using a MAb with a pI of 8.6-9.3. Gradients tested were as follows: PIT (2.4 mM Tris, 1.5 mM imidazole, 11.6 mM piperazine, pH 6-11); salt mediated PIT (4 mM Tris, 4 mM imidazole, 4 mM piperazine, pH 5-11, 16 mM NaCl); salt mediated TPP (5 mM Tris, 5 mM piperazine, 5 mM phosphate, pH 6-11, 20 mM NaCl gradient); TPP (5 mM Tris, 5 mM piperazine, 5 mM phosphate, pH 6-9, 20 mM NaCl); TIC (5 mM Tris, 5 mM piperazine, 5 mM CAPS, pH 7-10, 30 mM NaCl). Runs were 20-22 minutes.
Figure 21:
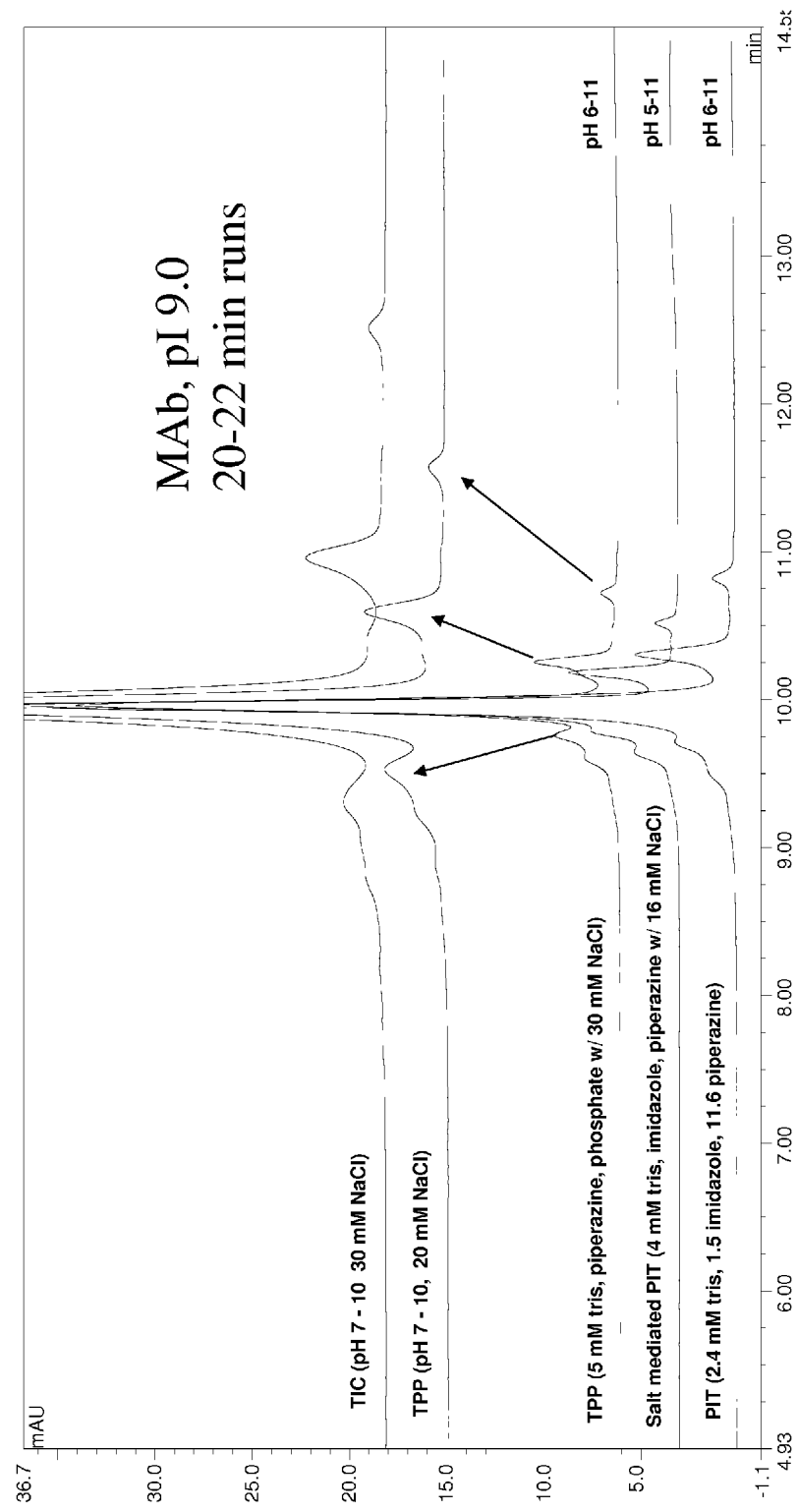
FIG. 21 is a graph showing that using a shallow pH gradient may improve peak resolution using a MAb with a pI of 9.0. Gradients tested were as follows: PIT (2.4 mM Tris, 1.5 mM imidazole, 11.6 mM piperazine, pH 6-11); salt mediated PIT (4 mM Tris, 4 mM imidazole, 4 mM piperazine, pH 5-11, 16 mM NaCl); TPP (5 mM Tris, 5 mM piperazine, 5 mM phosphate, pH 6-11, 30 mM NaCl gradient); TPP (5 mM Tris, 5 mM piperazine, 5 mM phosphate, pH 7-10, 20 mM NaCl); TIC (5 mM Tris, 5 mM piperazine, 5 mM CAPS, pH 7-10, 30 mM NaCl). Runs were 20-22 minutes.

Improved separations were achieved by altering gradient conditions. A shallow hybrid pH-IEC gradient (using TPP mobile phases) resulted in improved peak separation compared to either the original and salt mediated pH-IEC methods (FIGS. 19 and 20). Similar separation was achieved by using TIC buffer (Tris, Imidazole, CAPS) with 10 mM NaCl to replace piperazine, a hazardous disposal concern, and phosphate, a versatile biological buffer that may adversely induce assay artifact due to buffer-catalyzed post translational modification (FIG. 21).

The short hybrid pH-IEC method was further challenged to determine if faster analysis times would be possible. The pH gradient was set from pH 7-10 in 10 minutes, with a 2 minute hold at pH 10 and a 3 min equilibration time for a total run time of 15 minutes.

Chromatography conditions were as follows: Instrument: U3000 2DLC; Mobile phases: 10 mM Tris, piperazine, phosphate, A) pH 6.0, B) pH 11.0; C) 100 mM NaCl, D) milliQ water; Column: Propac WCX-10HT, 4×50 mm, 10 μm; Column temp: 40° C.; Flow rate: 1 mL/min; pH Gradient: 0-30% B; salt constant: 0 mM=0% C, 50% D; 10 mM=10% C, 40% D; 20 mM=20% C, 30% D, 30 mM=30% C, 20% D, 40 mM=40% C, 10% D, 50 mM=50% C, 0% D; Sample conc.: 1 μg/μL; Loaded volume: 20 μL.

Figure 22:
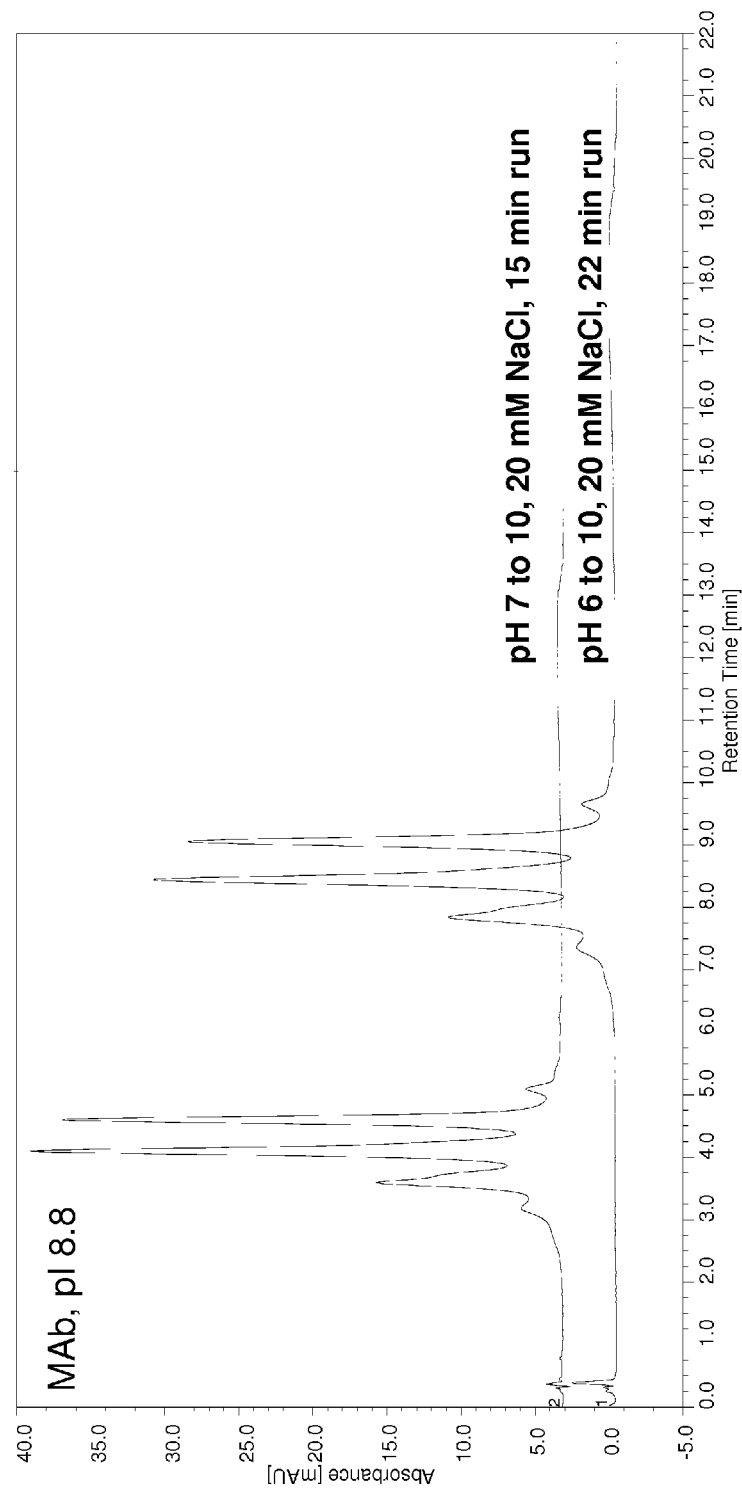
FIG. 22 is a graph showing that run times of fifteen minutes are possible. The Mab has a pI of 8.8. Two chromatograms are shown, one with a pH gradient from 6 to 10 in 20 mM NaCl in 22 minutes, and one with a pH gradient from 7 to 10 in 20 mM NaCl in 15 minutes.
Figure 23:
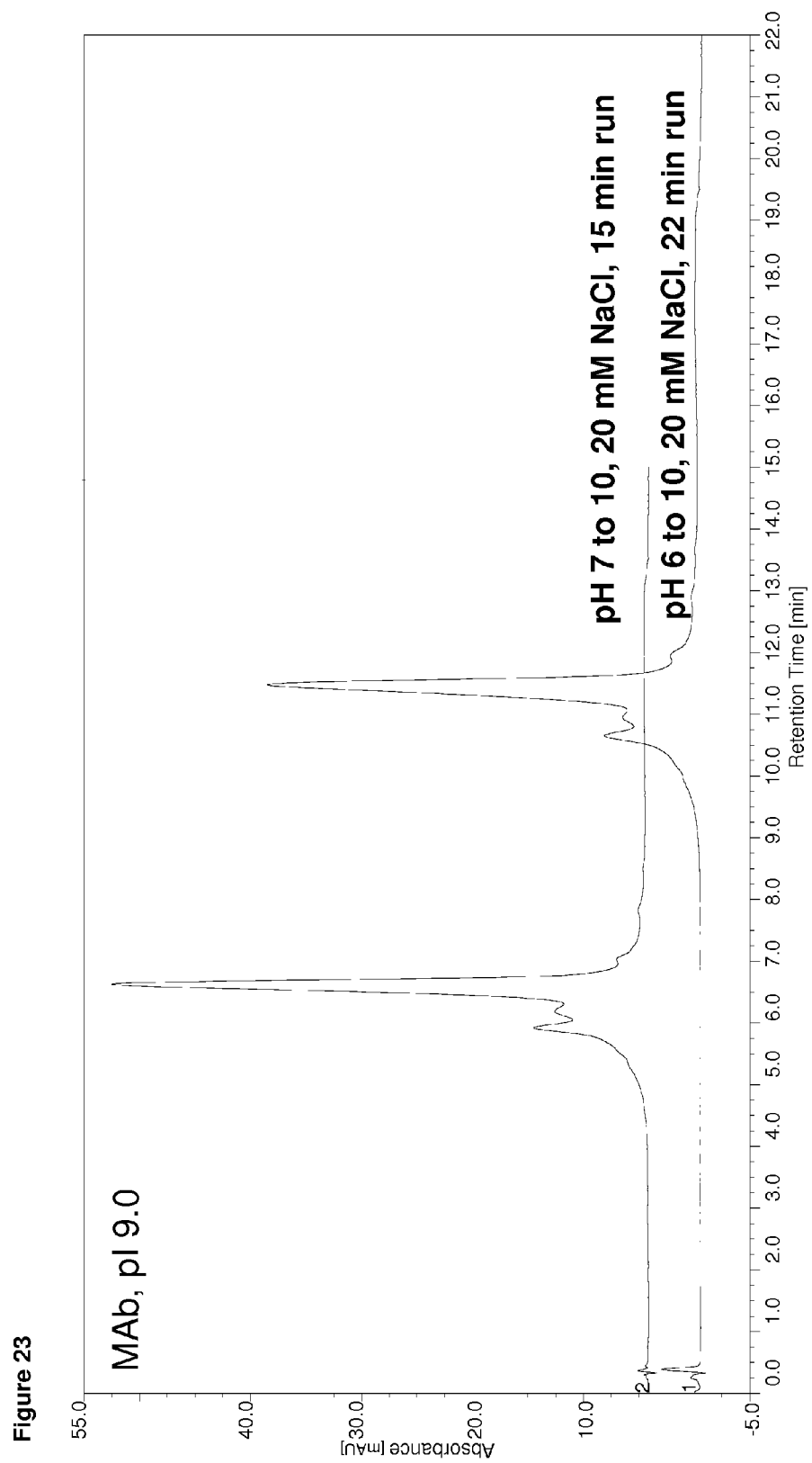
FIG. 23 is a graph showing that run times of fifteen minutes are possible. The Mab has a pI of 9.0. Two chromatograms are shown, one with a pH gradient from 6 to 10 in 20 mM NaCl in 22 minutes, and one with a pH gradient from 7 to 10 in 20 mM NaCl in 15 minutes.

As shown in FIGS. 22 and 23, profiles were similar between 15 and 22 min runs for two different MAbs with pI values of 8.8 and 9.0, respectively. However, as the run times became shorter, more product specific starting/ending pH values and salt concentrations were necessary.

When developing product specific method, optimal resolution can be achieved by carefully selecting the appropriate pH-gradient slope and salt concentration based on molecule's pI. Product specific methods would be beneficial if only one product is exclusively analyzed in a sequence. For laboratories that analyze a variety of mAbs, each with a different pI, using a quaternary system that can deliver a pH-gradient while maintaining a certain salt concentration is desirable. Otherwise, a longer run time of 22 min may be required as a platform method using a binary system that delivers the pH-gradient at a fixed salt concentration.

Example 9

Robustness of Ionic Strength-mediated pH Gradient Ion Exchange Chromatography

To demonstrate the robustness window and the target running conditions of an ionic strength-mediated pH gradient ion exchange chromatography suitable for analysis of multiple monoclonal antibody products with pI's across a wide range using a design of experiment (DOE) approach. The method is suitably robust if there is no significant change for the reportable values including the relative peak areas of the main (Main %), acidic variant (AV %) and basic variant (BV %) peaks. In addition, the general peak profile as measured by peak resolutions (Rs1 and Rs2). To test robustness, running parameters such as salt concentration, buffer concentrations, pH, column temperature, and flow rate are intentionally perturbed.

Materials and Methods

The following three antibodies were tested:
mAb1, pI=8.2
mAb2, pI=8.5
mAb3, pI=9.0

A Waters 2796 Bioseparations Module equipped with an 8-port, 3-way switch valve to the column, 6-port solvent selector valves for lines C and D and Waters 2487 Dual λ UV detector was used for the chromatography.

The chromatography column was a Dionex ProPac WCX-10 HT, 4×50 mm column.

The buffer system was as follows: equal molar of imidazole, Tris, and CAPS for buffers A & B. Buffer C was 100 mM NaCl and buffer D was water.

For Buffer A the pH was as specified in the experiment design table (Table 6), the pH for buffer B was 10.0. The Total buffer strength and salt concentration that were used are shown in the experiment design table.

The gradient was as follows: 0-2 min, at starting pH; 2-16 min from starting pH to pH 10; 16-18 min, at pH 10; 18-22 min, at starting pH. Selected salt concentrations remained constant through gradient.

Column Temperature and flow rate were used as indicated in Table 6.

3 mAbs:
mAb1, pI=8.2
mAb2, pI=8.5
mAb3, pI=9.0

Waters 2796 Bioseparations Module equipped with an 8-port, 3-way switch valve to the column, 6-port solvent selector valves for lines C and D and Waters 2487 Dual λ UV detector.

Dionex ProPac WCX-10 HT, 4×50 mm column

Buffer system: equal molar of imidazole, Tris, and CAPS for buffers A & B. Buffer C is 100 mM NaCl and buffer D is water.

Buffer A pH is specified in the experiment design table, pH for buffer B is 10.0. Total buffer strength and salt concentration are shown in the experiment design table.

Gradient: 0-2 min, at starting pH; 2-16 min from starting pH to 10; 16-18 min, at pH10, 18-22 min, at starting pH. Selected salt conc. remains constant through gradient.

Column Temperature and flow rate: see experiment design table

TABLE 6

Experimental Design (Running Parameters)

| Pattern | Salt (mM) | Buffer (mM) | Start pH | Column Temp. (° C.) | Flow (ml/min) |
|---|---|---|---|---|---|
| +++-- | 25 | 20 | 6.3 | 36 | 0.8 |
| --+-- | 15 | 10 | 6.3 | 36 | 0.8 |
| -+--- | 15 | 20 | 5.7 | 36 | 0.8 |
| +-+-+ | 25 | 10 | 6.3 | 36 | 1.2 |
| -++-+ | 15 | 20 | 6.3 | 36 | 1.2 |
| +--++ | 25 | 10 | 5.7 | 44 | 1.2 |
| ----+ | 15 | 10 | 5.7 | 36 | 1.2 |
| 0 | 20 | 15 | 6.0 | 40 | 1 |
| +++++ | 25 | 20 | 6.3 | 44 | 1.2 |
| ++-+- | 25 | 20 | 5.7 | 44 | 0.8 |
| --+++ | 15 | 10 | 6.3 | 44 | 1.2 |
| ---+- | 15 | 10 | 5.7 | 44 | 0.8 |
| -+-++ | 15 | 20 | 5.7 | 44 | 1.2 |
| +-++- | 25 | 10 | 6.3 | 44 | 0.8 |
| -+++- | 15 | 20 | 6.3 | 44 | 0.8 |
| ++--+ | 25 | 20 | 5.7 | 36 | 1.2 |
| +---- | 25 | 10 | 5.7 | 36 | 0.8 |
| 0 | 20 | 15 | 6.0 | 40 | 1 |

Figure 24:
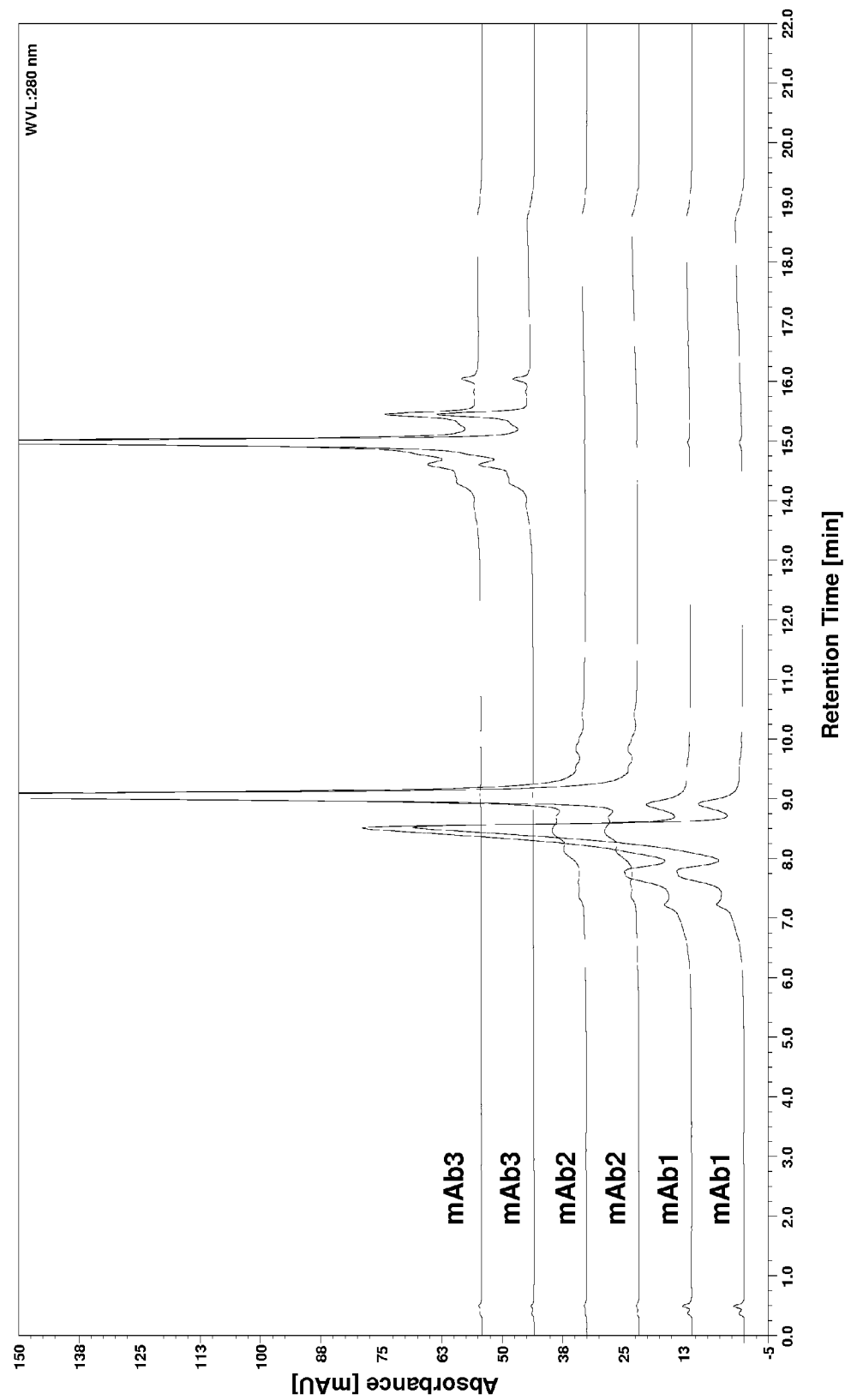
FIG. 24 is a graph showing overlaid chromatograms of duplicate analysis of three monoclonal antibodies at the target condition.
Figure 25:
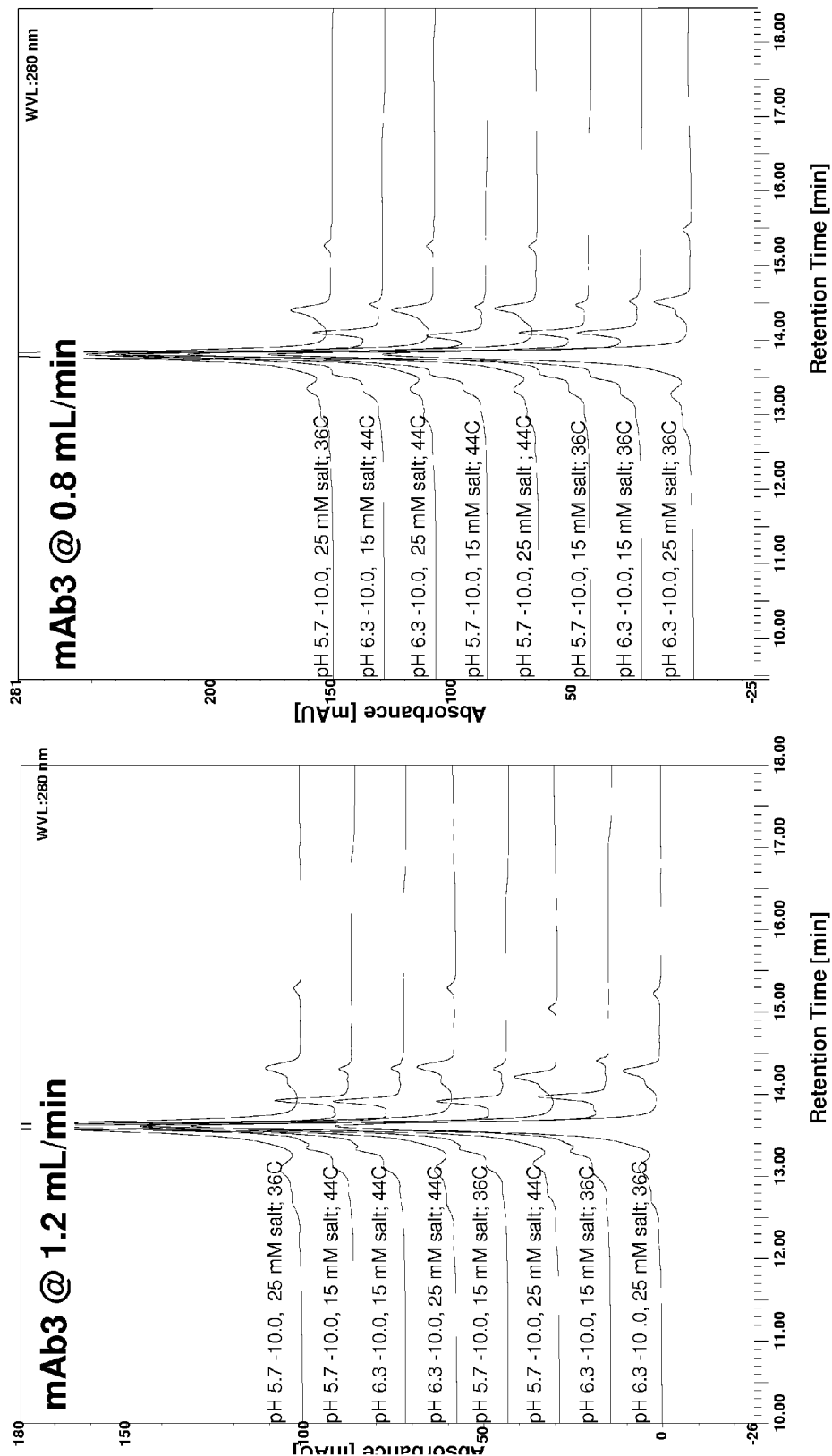
FIG. 25 is a graph showing overlaid chromatograms of MAb3 at different chromatography conditions. Main peaks are aligned.

The robustness of the chromatography procedure for the analysis of multiple monoclonal antibody products was tested by systematically perturbing the parameters from the target running conditions of 20 mM salt, 15 mM buffer, starting pH 6.0, column temperature 40° C., and a flow rate of 1.0 ml/min (designated as 0 in Table 6). Three different MAbs, with pI's of 8.2, 8.5 and 9.0 were tested. The resulting chromatograms of duplicate chromatographies at the target running condition are presented in FIG. 24. An example of a test for the robustness of the target running condition for MAb3 by perturbing the running conditions according to Table 6 is presented in FIG. 25. Although there are some minor differences in resolution, the general peak profiles, especially for the three regions (acidic, main, and basic) are maintained and allow quantitation.

Figure 26:
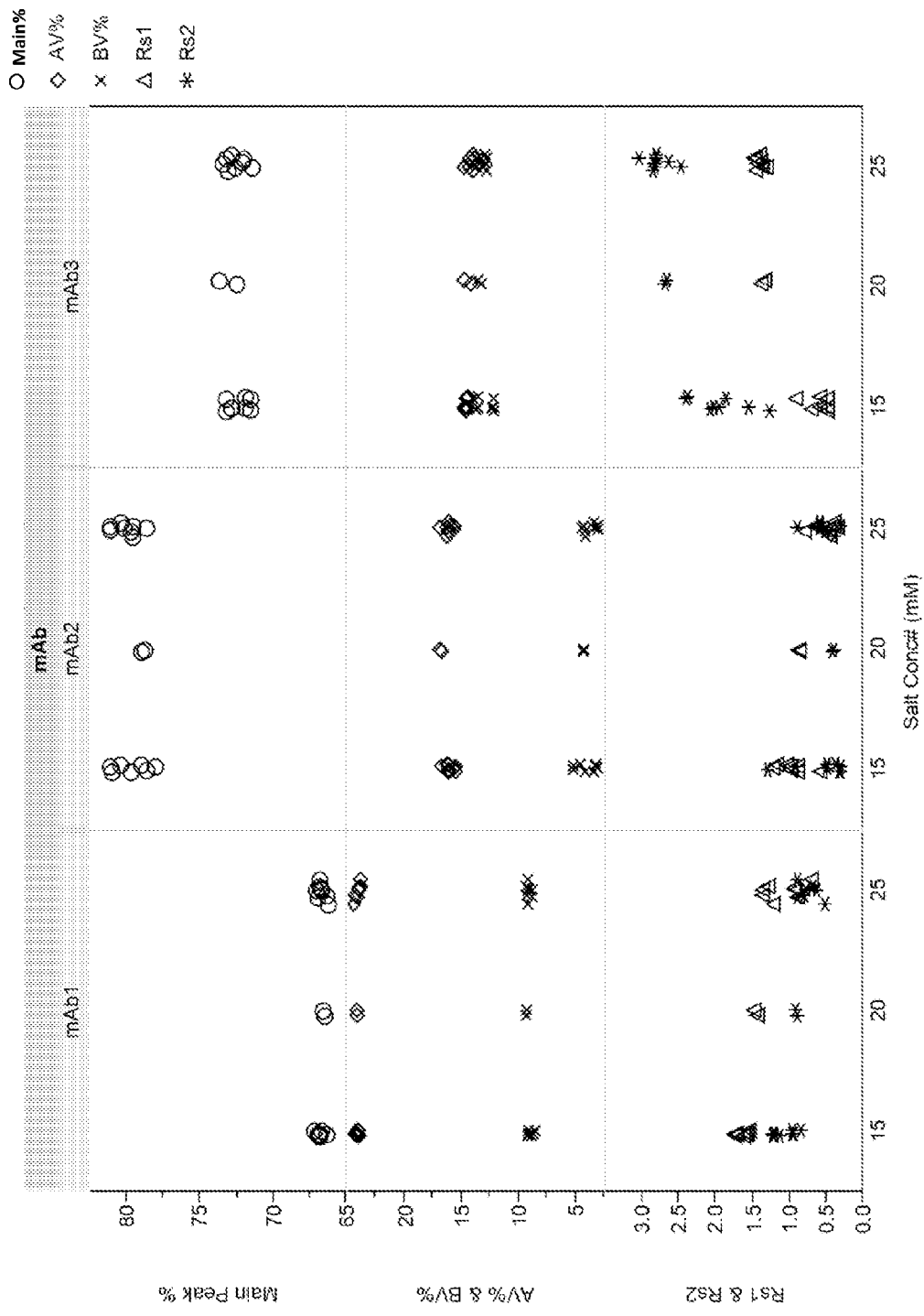
FIG. 26 is a distribution plot showing the effect of salt concentration on chromatography performance. Circles represent main peak percentage, diamonds represent acidic variants percentage, × represents basic variant percentage, triangles represent resolution 1, and * represents resolution 2.

The effects of running parameters on method performance can be visualized using a distribution plot (FIG. 26). In this plot, the reportable values (Main %, AV % and BV %) for analyses at different conditions were distributed closely around those at the target condition (at the center of each panel, i.e. 20 mM salt). The results show that there was no significant effect on the reportable values due to salt concentration. However, there was a trend in resolutions with the increase of salt concentration: a slight downward trend for MAb1 (pI=8.2) and MAb2 (pI=8.5), and an upward trend for MAb3 (pI=9). It suggested that with the increase in molecules' pI, the resolution can be further improved by increasing salt concentration, for a product specific method. As a multi-product method, the salt concentration was optimized for mAbs with pI across a wide range. The results of these studies demonstrated that 20 mM is the useful salt concentration for analysis of antibodies with a pI ranging from 7.0 to 9.5.

Figure 27:
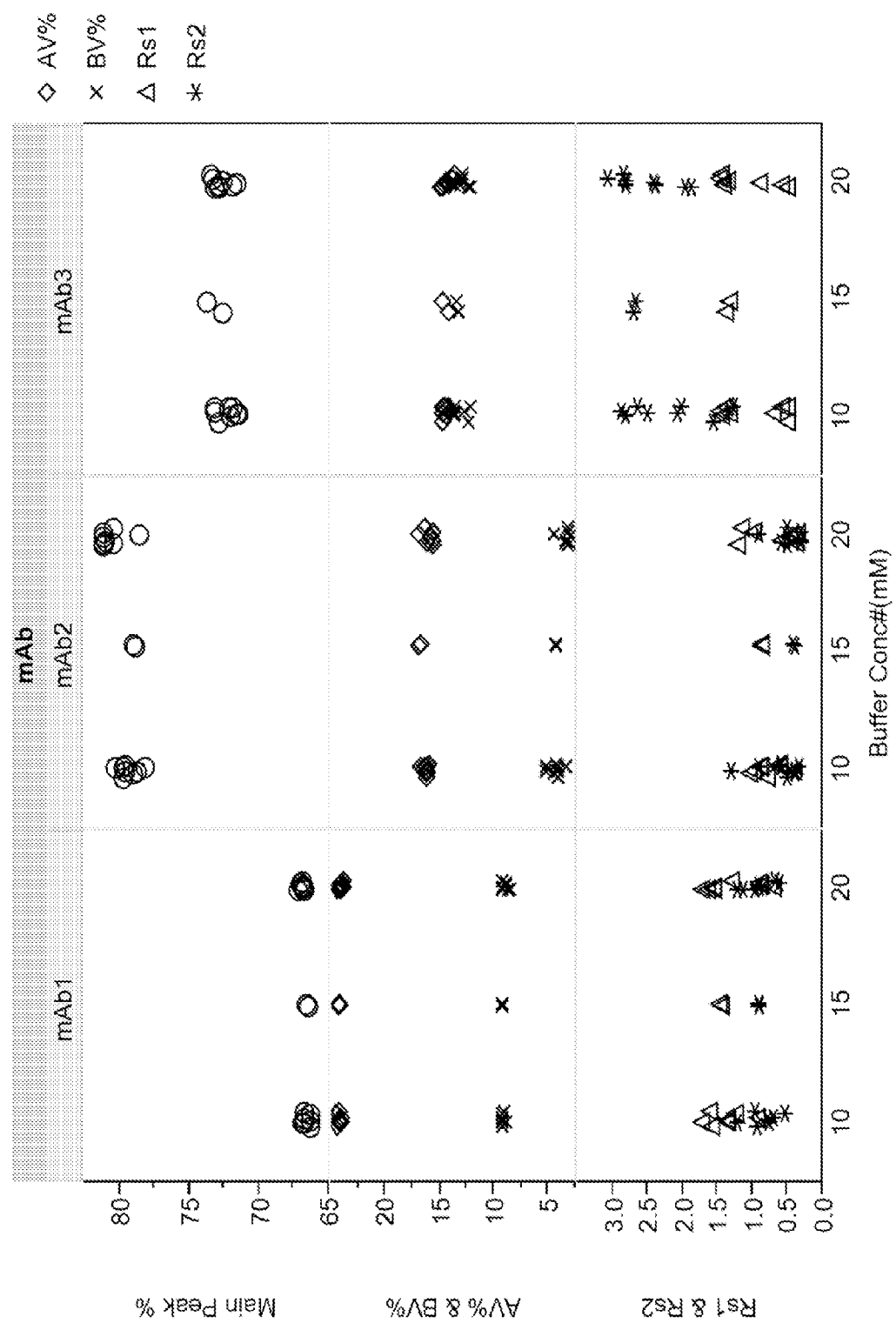
FIG. 27 shows distribution plots showing the effects of other parameters on chromatography performance. Top left shows the effect of buffer concentration (mM). Top right shows the effect of starting pH. Bottom left shows the effect of column temperature in ° C. Bottom right shows the effect of flow rate (ml/min).
Figure 27:
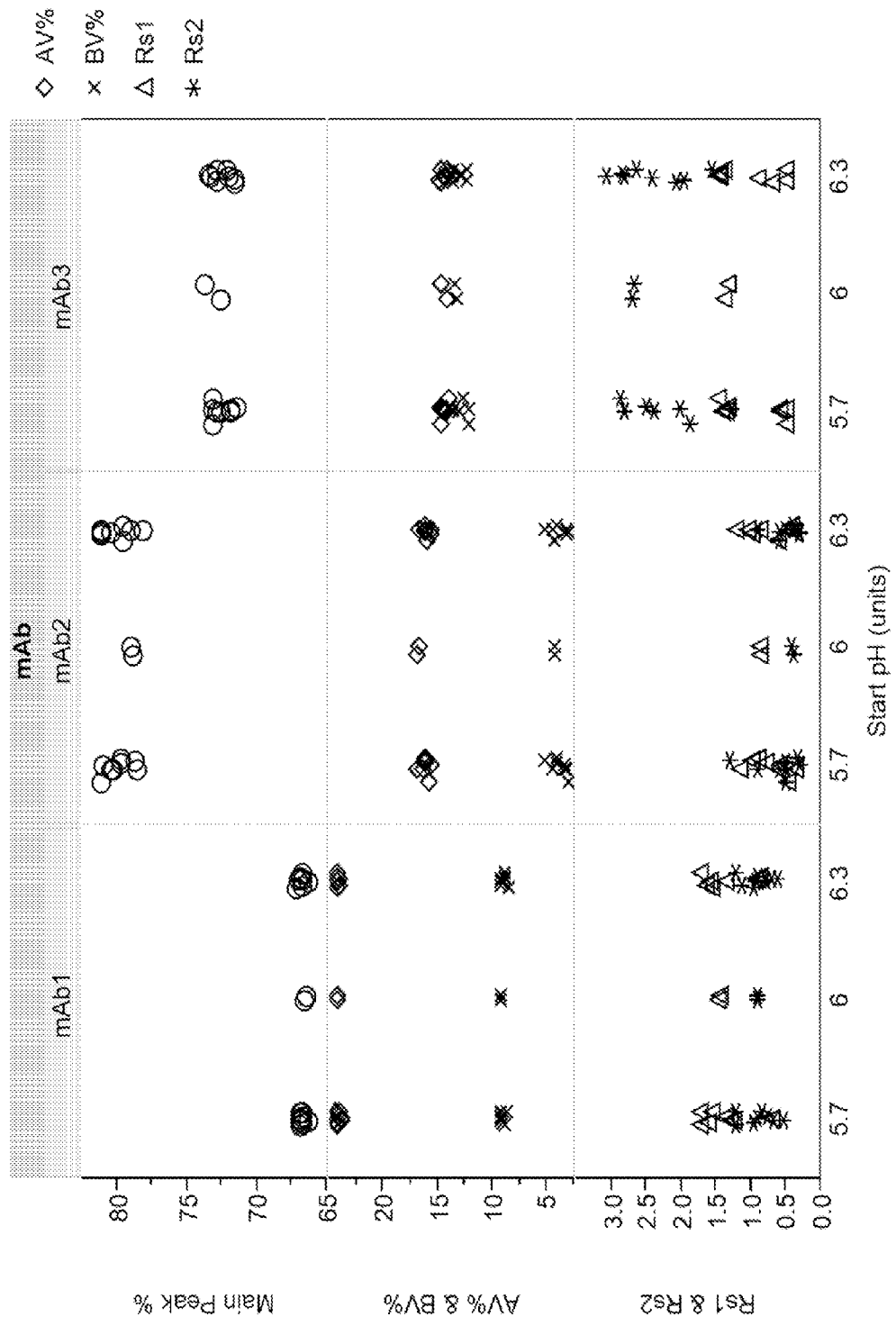
Figure 27:
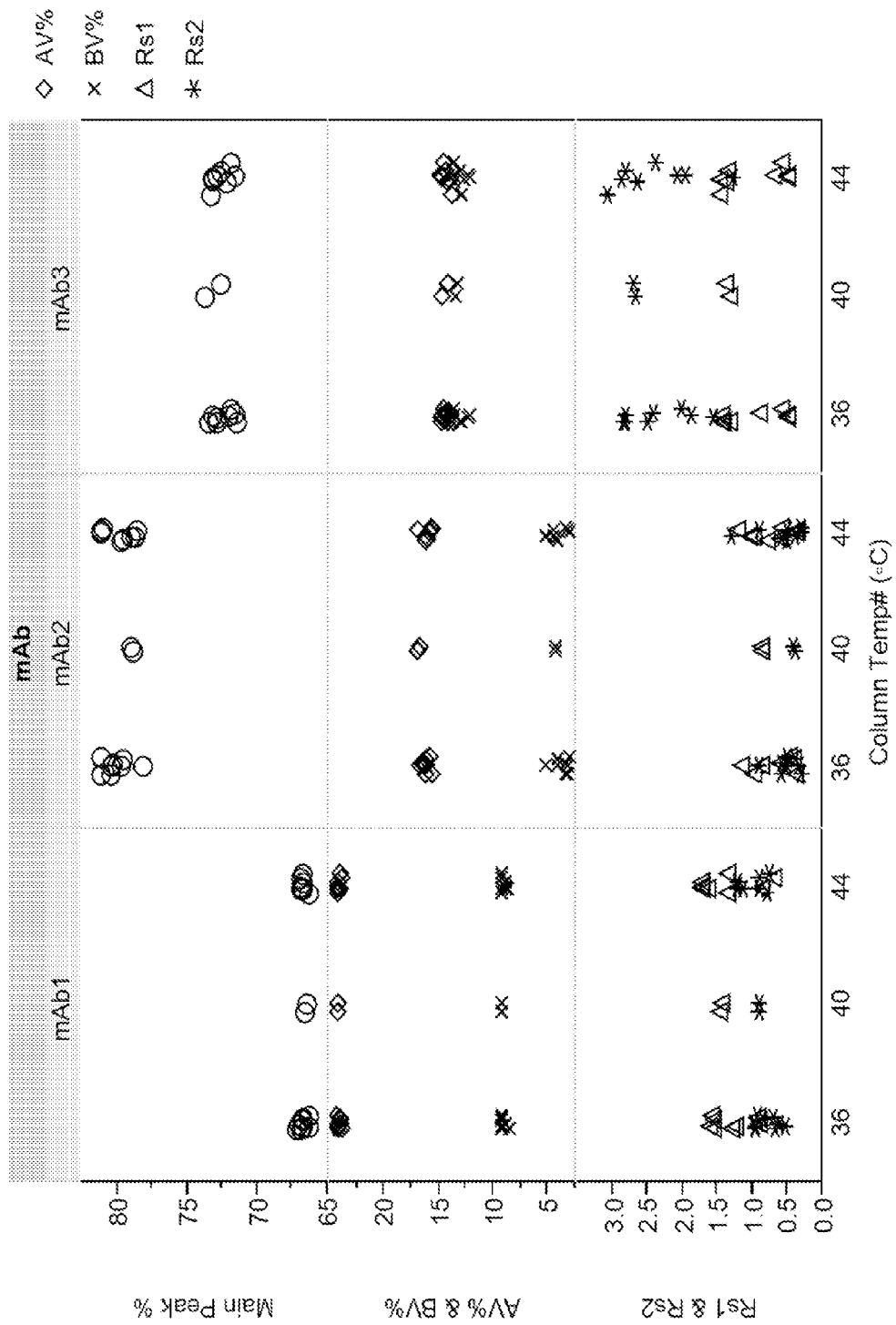
Figure 27:
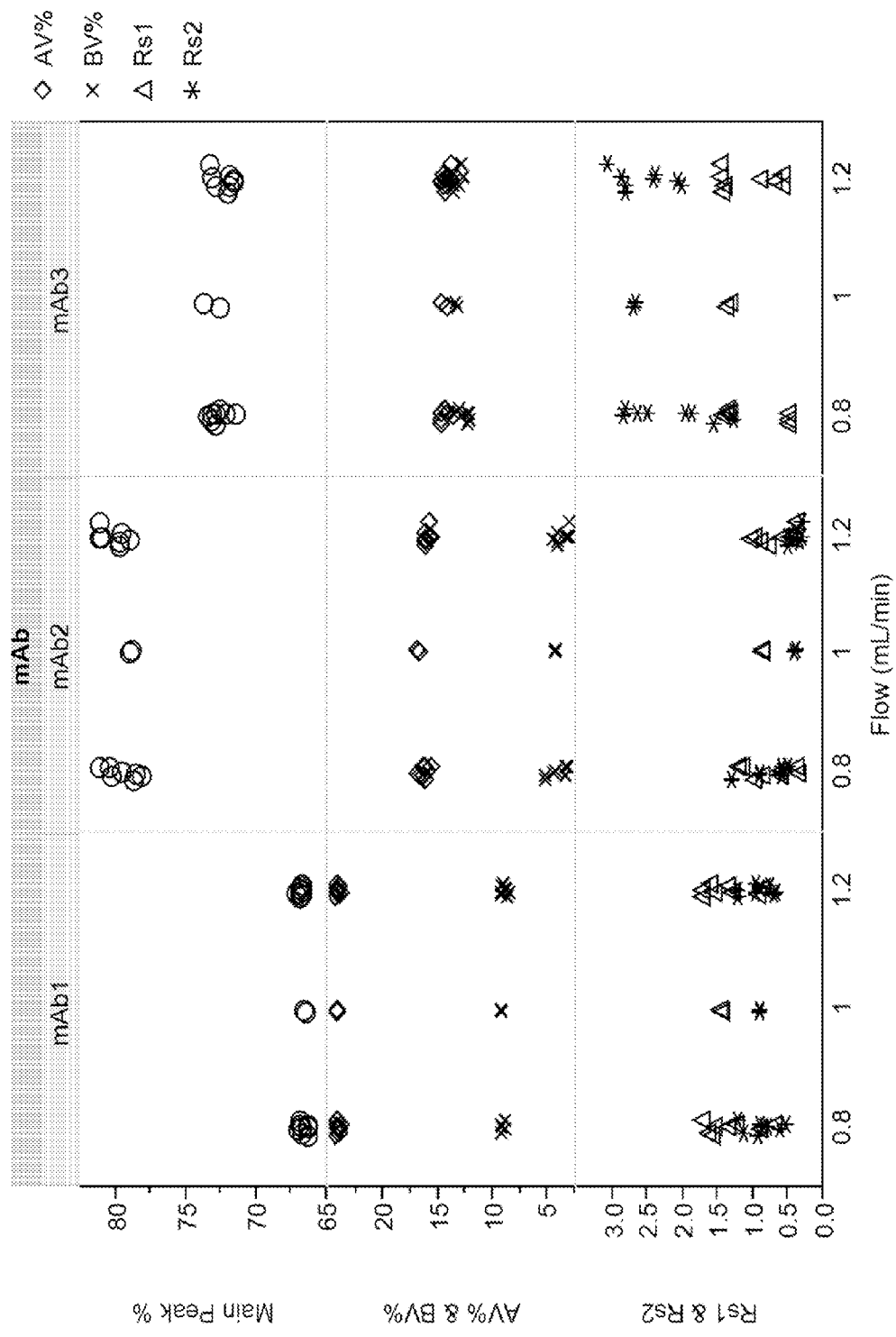

The effects of the other running parameters were also plotted and are presented in FIG. 27. In these plots, the reportable values (Main %, AV % and BV %) for analyses at different condition were also centered around those at the target conditions. The results demonstrated that there was no significant effect on the reportable values due to the intentional perturbation of running conditions. Thus, the multi-product method is suitably robust at the target running condition.

What is claimed is:

1. A method for analyzing a composition comprising a polypeptide and one or more contaminants, the method comprising
   a) binding the polypeptide and one of more contaminants to an ion-exchange chromatography material using a loading buffer, wherein the loading buffer is at an initial pH and comprises an initial ionic strength;
   b) eluting the polypeptide and one or more contaminants from the ion-exchange chromatography material using an elution buffer wherein the pH of the elution buffer is altered in a pH gradient and wherein the ionic strength of the elution buffer is essentially the same as the initial ionic strength of the loading buffer, wherein the polypeptide and the one or more contaminants are separated by pH gradient at about the initial ionic strength; and
   c) detecting the polypeptide and the one or more contaminants.

2. A method for analyzing a polypeptide in a composition comprising a polypeptide and one or more contaminants, the method comprising
   a) binding the polypeptide and one of more contaminants to an ion-exchange chromatography material using a loading buffer, wherein the loading buffer is at an initial pH and comprises an initial ionic strength;
   b) eluting the polypeptide and one or more contaminants from the ion-exchange chromatography material using an elution buffer wherein the pH of the elution buffer is altered in a pH gradient and wherein the ionic strength of the elution buffer is essentially the same as the initial ionic strength of the loading buffer, wherein the polypeptide and the one or more contaminants are separated by pH gradient at about the initial ionic strength; and
   c) detecting the polypeptide and the one or more contaminants, wherein the method is used to analyze polypeptides having a pI ranging from about 7.0 to about 9.5.

3. The method of claim 1, wherein the polypeptide is an antibody or immunoadhesin or fragment thereof.

4. The method of claim 1, wherein the polypeptide is a monoclonal antibody or fragment thereof.

5. The method of claim 3, wherein the antibody is a human antibody.

6. The method of claim 3, wherein the antibody is a humanized antibody.

7. The method of claim 3, wherein the antibody is a chimeric antibody.

8. The method of claim 3, wherein the antibody is an antibody fragment.

9. The method of claim 1, wherein the contaminant is a variant of the polypeptide.

10. The method of claim 1, wherein the contaminant is a degradation product of the polypeptide.

11. The method of claim 1, wherein the polypeptide has a pI greater than about 9.0.

12. The method of claim 1, wherein the chromatography material is a cation exchange chromatography material.

13. The method of claim 12, wherein the cation exchange chromatography material is a sulfonated chromatography material or a carboxylated chromatography material.

14. The method of claim 1, wherein the pH gradient is a linear gradient or a step gradient.

15. The method of claim 14, wherein the pH gradient comprises an increase from about pH 5 to about pH 11.

16. The method of claim 1, wherein the pH gradient is generated using one or more buffers.

17. The method of claim 16, wherein the one or more buffers selected from piperazine, imidazole, tris, phosphate, or CAPS.

18. The method of claim 1, wherein the ionic strength of the elution buffer is from about 10 mM to about 100 mM.

19. The method of claim 18, wherein the elution buffer comprises about 10 mM NaCl to about 100 mM NaCl, about 10 mM KCl to about 100 mM KCl, or about 10 mM $Na_2SO_4$ to about 100 mM $Na_2SO_4$.

20. The method of claim 1, wherein the polypeptide has a pI less than about 7.0.

21. The method of claim 20, wherein the chromatography material is an anion exchange chromatography material.

22. The method of claim 21, wherein the anion exchange chromatography material is a quarternary amine chromatography material or a tertiary amine chromatography material.

23. The method of claim 20, wherein the pH gradient is a linear gradient or a step gradient.

24. The method of claim 23, wherein the pH gradient comprises a decrease from about pH 8 to about pH 5.

25. The method of claim 20, wherein the ionic strength of the elution buffer is from about 10 mM to about 100 mM.

26. The method of claim 25, wherein the elution buffer comprises about 10 mM NaCl to about 100 mM NaCl.

27. The method of claim 1, wherein the analysis is by high performance liquid chromatography.

28. The method of claim 2, wherein the polypeptide is an antibody or immunoadhesin or fragment thereof.

29. The method of any one of claims 2, wherein the polypeptide is a monoclonal antibody or fragment thereof.

30. The method of claim 29, wherein the antibody is a human antibody.

31. The method of claim 29, wherein the antibody is a humanized antibody.

32. The method of claim 29, wherein the antibody is a chimeric antibody.

33. The method of claim 2, wherein the antibody is an antibody fragment.

34. The method of claim 2, wherein the contaminant is a variant of the polypeptide.

35. The method of claim 2, wherein the contaminant is a degradation product of the polypeptide.

36. The method of claim 2, wherein the contaminant is a charge variant of the polypeptide.

37. The method of claim 1, wherein the concentration of the buffer in the loading buffer and/or the elution buffer varies from about 10 mM to about 50 mM.

38. The method of claim 1, wherein the first pH varies from about pH 5.0 to about pH 7.0.

39. The method of claim 1, wherein the temperature of the chromatography material varies from about 20° C. to about 50° C.

40. The method of claim 1, wherein the loading and elution are conducted at a flow rate varying from about 0.5 ml/min to about 2.0 ml/min.

41. The method of claim 2, wherein the concentration of the buffer in the loading buffer and/or the elution buffer varies from about 10 mM to about 50 mM.

42. The method of claim 2, wherein the first pH varies from about pH 5.0 to about pH 7.0.

43. The method of claim 2, wherein the temperature of the chromatography material varies from about 20° C. to about 50° C.

44. The method of claim 2, wherein the loading and elution are conducted at a flow rate varying from about 0.5 ml/min to about 2.0 ml/min.

45. The method of claim 20, wherein the pH gradient is generated using one or more buffers.

46. The method of claim 45, wherein the one or more buffers selected from piperazine, imidazole or Tris.

* * * * *